US008663643B2

(12) United States Patent
Berry et al.

(10) Patent No.: US 8,663,643 B2
(45) Date of Patent: Mar. 4, 2014

(54) COMBINATIONS OF AN ANTI-HER2 ANTIBODY-DRUG CONJUGATE AND CHEMOTHERAPEUTIC AGENTS, AND METHODS OF USE

(75) Inventors: Leanne Berry, South San Francisco, CA (US); Gail Lewis Phillips, San Carlos, CA (US); Mark X. Sliwkowski, San Carlos, CA (US)

(73) Assignee: Genentech, Inc., South San Francisco, CA (US)

( * ) Notice: Subject to any disclaimer, the term of this patent is extended or adjusted under 35 U.S.C. 154(b) by 652 days.

(21) Appl. No.: 12/400,988

(22) Filed: Mar. 10, 2009

(65) Prior Publication Data

US 2012/0107302 A1 May 3, 2012

Related U.S. Application Data

(60) Provisional application No. 61/037,410, filed on Mar. 18, 2008.

(51) Int. Cl.
*A61K 39/00* (2006.01)
*C07K 16/00* (2006.01)
*C07K 14/435* (2006.01)

(52) U.S. Cl.
USPC .................. 424/181.1; 424/178.1; 424/179.1; 530/388.1; 530/350

(58) Field of Classification Search
USPC .................. 424/178.1, 179.1, 181.1
See application file for complete search history.

(56) References Cited

U.S. PATENT DOCUMENTS

| | | | |
|---|---|---|---|
| 3,896,111 A | 7/1975 | Kupchan et al. |
| 4,137,230 A | 1/1979 | Hashimoto et al. |
| 4,151,042 A | 4/1979 | Higashide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,450,254 A | 5/1984 | Isley et al. |
| 4,753,894 A | 6/1988 | Frankel et al. |
| 4,956,453 A | 9/1990 | Bjorn et al. |
| 4,958,009 A | 9/1990 | Bjorn et al. |
| 4,968,603 A | 11/1990 | Slamon et al. |
| 4,981,979 A | 1/1991 | Sivam |
| 5,183,884 A | 2/1993 | Kraus et al. |
| 5,206,018 A | 4/1993 | Sehgal et al. |
| 5,208,020 A | 5/1993 | Chari et al. |
| 5,217,713 A | 6/1993 | Iwasa et al. |
| 5,395,924 A | 3/1995 | Blattler et al. |
| 5,416,064 A | 5/1995 | Chari et al. |
| 5,480,968 A | 1/1996 | Kraus et al. |
| 5,514,554 A | 5/1996 | Bacus |
| 5,629,197 A | 5/1997 | Ring et al. |
| 5,639,641 A | 6/1997 | Pedersen et al. |
| 5,677,171 A | 10/1997 | Hudziak et al. |
| 5,679,648 A | 10/1997 | McCaffrey et al. |
| 5,705,157 A | 1/1998 | Greene |
| 5,725,856 A | 3/1998 | Hudziak et al. |
| 5,747,261 A | 5/1998 | King et al. |
| 5,772,997 A | 6/1998 | Hudziak et al. |
| 5,783,186 A | 7/1998 | Arakawa et al. |
| 5,821,337 A | 10/1998 | Carter |
| 5,824,311 A | 10/1998 | Greene et al. |
| 5,837,234 A | 11/1998 | Gentile et al. |
| 5,840,525 A | 11/1998 | Vandlen et al. |
| 5,877,305 A | 3/1999 | Huston et al. |
| 5,919,815 A | 7/1999 | Bradley et al. |

(Continued)

FOREIGN PATENT DOCUMENTS

| | | |
|---|---|---|
| AU | 03/259913 | 8/2003 |
| AU | 03/247762 | 1/2004 |

(Continued)

OTHER PUBLICATIONS

Xiao et al. (Clinical Chemistry 2009, 55:1307-1315).*
Krontiris and Capizzi (Internal Medicine, 4th Edition, Editor-in-chief Jay Stein, Elsevier Science, 1994 Chapters 71-72, pp. 699-729).*
Carter, S. K. et al. (Chemotherapy of Cancer; Second edition; John Wiley & Sons: New York, 1981; appendix C).*
Gura (Science, 1997, 278:1041-1042).*
Kaiser (Science, 2006, 313: 1370).*
Berenbaum (Clin. Exp Immunol. 28:1-18, 1977).*
Wiesenthal (http://weisenthal.org/feedback. html, Feb. 4, 2002).*
Sutherlin et al., "Discovery of a Potent, Selective, and Orally Available Class I Phosphatidylinositol 3-Kinase (PI3K)/Mammalian Target of Rapamycin (mTOR) Kinase Inhibitor (GDC-0980) for the Treatment of Cancer", Journal of Medicinal Chemistry 54:7579-7587 (2011).

(Continued)

*Primary Examiner* — Misook Yu
*Assistant Examiner* — Yan Xiao
(74) *Attorney, Agent, or Firm* — Danielle Pasqualone; Ginger R. Dreger; Arnold & Porter LLP

(57) ABSTRACT

Combinations of the antibody-drug conjugate trastuzumab-MCC-DM1 and chemotherapeutic agents, including stereoisomers, geometric isomers, tautomers, solvates, metabolites and pharmaceutically acceptable salts thereof, are useful for inhibiting tumor cell growth, and for treating disorders such as cancer mediated by HER2 and KDR (VEGFR receptor 1). Methods of using such combinations for in vitro, in situ, and in vivo diagnosis, prevention or treatment of such disorders in mammalian cells, or associated pathological conditions, are disclosed.

28 Claims, 27 Drawing Sheets

(56) References Cited

U.S. PATENT DOCUMENTS

| | | | |
|---|---|---|---|
| 5,968,517 A | 10/1999 | Duncan et al. |
| 6,022,541 A | 2/2000 | Senger et al. |
| 6,054,297 A | 4/2000 | Carter et al. |
| 6,333,410 B1 | 12/2001 | Chari et al. |
| 6,436,931 B1 | 8/2002 | Chari et al. |
| 6,441,163 B1 | 8/2002 | Chari et al. |
| 6,531,131 B1 | 3/2003 | Gu et al. |
| 6,632,979 B2 | 10/2003 | Erickson et al. |
| 6,716,821 B2 | 4/2004 | Zhao et al. |
| 6,913,748 B2 | 7/2005 | Widdison |
| 7,030,231 B1 | 4/2006 | Craik et al. |
| 7,097,840 B2 | 8/2006 | Erickson et al. |
| 7,276,497 B2 | 10/2007 | Chari et al. |
| 7,303,749 B1 | 12/2007 | Chari et al. |
| 7,375,078 B2 | 5/2008 | Feng |
| 7,521,541 B2 | 4/2009 | Eigenbrot et al. |
| 7,575,748 B1 | 8/2009 | Erickson et al. |
| 7,601,354 B2 | 10/2009 | Chari et al. |
| 7,754,211 B2 | 7/2010 | Rosenblum et al. |
| 7,989,598 B2 | 8/2011 | Steeves et al. |
| 8,088,387 B2 | 1/2012 | Steeves et al. |
| 8,142,784 B2 | 3/2012 | Ebens et al. |
| 8,163,888 B2 | 4/2012 | Steeves et al. |
| 8,198,417 B2 | 6/2012 | Steeves et al. |
| 2002/0001587 A1 | 1/2002 | Erickson et al. |
| 2003/0103985 A1 | 6/2003 | Adolf |
| 2003/0235582 A1 | 12/2003 | Singh |
| 2004/0057952 A1 | 3/2004 | Payne et al. |
| 2004/0120949 A1 | 6/2004 | Adolf et al. |
| 2004/0126379 A1 | 7/2004 | Adolf et al. |
| 2004/0235068 A1 | 11/2004 | Levinson |
| 2004/0235840 A1 | 11/2004 | Chari et al. |
| 2004/0241174 A1 | 12/2004 | Amphlett et al. |
| 2005/0133285 A1 | 6/2005 | Shimizu |
| 2005/0169933 A1 | 8/2005 | Steeves et al. |
| 2005/0238650 A1 | 10/2005 | Ebens et al. |
| 2005/0276812 A1 | 12/2005 | Ebens et al. |
| 2006/0275305 A1 | 12/2006 | Bryant et al. |
| 2007/0020261 A1 | 1/2007 | Sliwkowski et al. |
| 2007/0092940 A1 | 4/2007 | Eigenbrot et al. |
| 2008/0085283 A1 | 4/2008 | Levinson |
| 2008/0114153 A1 | 5/2008 | Steeves et al. |
| 2008/0145374 A1 | 6/2008 | Steeves et al. |
| 2008/0166294 A1 | 7/2008 | de Sauvage et al. |
| 2008/0171040 A1 | 7/2008 | Ebens, et al. |
| 2008/0171865 A1 | 7/2008 | Steeves et al. |
| 2008/0226659 A1 | 9/2008 | Erickson et al. |
| 2009/0041791 A1 | 2/2009 | Feng |
| 2009/0098115 A1 | 4/2009 | Crocker et al. |
| 2009/0098135 A1* | 4/2009 | Belvin et al. ............... 424/141.1 |
| 2009/0202536 A1 | 8/2009 | Ebens, Jr. et al. |
| 2010/0136033 A1 | 6/2010 | Erickson et al. |
| 2010/0233164 A1 | 9/2010 | Ebens et al. |
| 2011/0281856 A1 | 11/2011 | Chari et al. |
| 2012/0003217 A1 | 1/2012 | Bryant |

FOREIGN PATENT DOCUMENTS

| | | |
|---|---|---|
| DE | 40 14 540 A1 | 11/1991 |
| EP | 0 425 235 A2 | 2/1991 |
| EP | 0 563 475 | 10/1993 |
| EP | 1 354 896 | 10/2003 |
| EP | 391 213 A1 | 2/2004 |
| JP | 58-167592 | 10/1983 |
| JP | 62-195387 | 8/1987 |
| JP | 3161490 | 7/1991 |
| JP | 2001-503760 | 3/2001 |
| JP | 2002-541088 | 12/2002 |
| JP | 2002-543093 | 12/2002 |
| JP | 2003-501487 | 1/2003 |
| JP | 2003-503365 | 1/2003 |
| WO | WO 89/06692 | 7/1989 |
| WO | WO 93/21319 | 10/1993 |
| WO | WO 94/00136 | 6/1994 |
| WO | WO 94/22478 | 10/1994 |
| WO | WO 96/16173 | 5/1996 |
| WO | WO 97/00271 | 1/1997 |
| WO | WO 97/04801 | 2/1997 |
| WO | WO 98/02463 | 1/1998 |
| WO | WO 98/08506 | 3/1998 |
| WO | WO 98/17797 | 4/1998 |
| WO | WO 98/20020 | 5/1998 |
| WO | WO 99/31140 | 6/1999 |
| WO | WO 00/20579 | 4/2000 |
| WO | WO 00/69460 | 11/2000 |
| WO | WO 00/71718 | 12/2000 |
| WO | WO 00/76554 | 12/2000 |
| WO | WO 01/00238 A1 | 4/2001 |
| WO | WO 01/00244 A2 | 4/2001 |
| WO | WO 01/24673 | 4/2001 |
| WO | WO 01/38490 | 5/2001 |
| WO | WO 01/15730 A1 | 8/2001 |
| WO | WO 02/016429 | 2/2002 |
| WO | WO 02/057316 | 7/2002 |
| WO | WO 02/098883 | 12/2002 |
| WO | WO 03/000113 | 1/2003 |
| WO | WO 03/022995 | 3/2003 |
| WO | WO 03/024392 | 3/2003 |
| WO | WO 03/027135 | 4/2003 |
| WO | WO 03/057163 | 7/2003 |
| WO | WO 03/068956 | 8/2003 |
| WO | WO 03/070234 * | 8/2003 ............. A61K 31/13 |
| WO | WO 03/072036 | 9/2003 |
| WO | WO 03/074081 | 9/2003 |
| WO | WO 03/075855 | 9/2003 |
| WO | WO 2004/005470 | 1/2004 |
| WO | WO 2004/016225 | 2/2004 |
| WO | 2004/048525 A2 | 6/2004 |
| WO | WO 2005/037992 A2 | 4/2005 |
| WO | WO 2005/049075 | 6/2005 |
| WO | WO 2005/101017 | 10/2005 |
| WO | 2006/096861 A2 | 9/2006 |
| WO | WO 2007/127175 | 11/2007 |
| WO | WO 2007/129161 | 11/2007 |

OTHER PUBLICATIONS

Fields et al., "Enhanced in vitro and in vivo activity of trastuzumab-DM1 anti-drug conjugate combined with GDC-0941, a small molecule inhibitor of P13 kinase" *Proc. Ann. Mtg. Of the Amer. Assoc. for CA Res.*; 100th Ann. Mtg. of the Amer. Assoc. for CA Res., Denver 50:784 (Apr. 1, 2009).

Junttila et al., "Trastuzumab-mertansine (T-DM1) retains all the mechanisms of action (MOA) of trastuzumab and is extremely effective in combination with docetaxel" *EP Journal of Cancer* 6(12) : 163 (Oct. 1, 2008).

PCT International Search Report, mailed Feb. 10, 2010, in counterpart PCT International Application No. PCT/US2009/036608, filed Mar. 10, 2009.

Phillips et al., "Potent anti-tumor activity of trastuzumab-DM1 antibody-drug conjugate in combination with cytotoxic chemotherapeutic agents, antibodies or small molecule kinase inhibitors" *Proceedings of the American Association for Cancer Research Annual Meeting* 49:502 (2008).

Baselga et al., "A Phase II trial of trastuzumab and pertuzumab in patients with HER2—overexpressing metastatic breast cancer that had progressed during trastuzumab therapy: full response data (140P)" *Annals of Oncology* 19(Suppl 8):1 page (Sep 2008).

Beeram et al., "A phase I study of trastuzumab-MCC-DM1 (T-DM1), a first-in-class HER2 antibody-drug conjugate (ADC), in patients (pts) with HER2+metastatic breast cancer (BC) (Abstract No. 1042)" *Journal of Clinical Oncology*, 2007 ASCO Annual Meeting Proceedings 25(No. 18S):1 page (Jun 20, 2007).

Borisy et al., "Systematic discovery of multicomponent therapeutics" *Proc. Natl. Acad. Sci.* 100 (13) : 7977-7982 (2003).

Burris et al., "A Phase II Study of Trastuzumab-DM1 (T-DM1), a HER2 Antibody-Drug Conjugate, in Patients with HER2 Positive Metastatic Breast Cancer (Poster 155)" (ASCO Breast Cancer Symposium, Washington, DC, Sept 5-7, 2008) pps. 1 page.

Chari et al., "Immunoconjugates Containing Novel Maytansinoids: Promising Anticancer Drugs" *Cancer Research* 52:127-131 (Jan 1992).

(56) References Cited

OTHER PUBLICATIONS

Chari, "Targeted Delivery of Chemotherapeutics: Tumor-Activated Prodrug Therapy" *Advanced Drug Delivery Reviews* 31:89-104 (1998).
Fitzgerald et al., "Systems biology and combination therapy in the quest for clinical efficacy" *Nat Chem Biol.* 2(9) : 458-66 (Sep. 2006).
Junttila et al., "Ligand-independent HER2/HER3/PI3K complex is disrupted by trastuzumab and is effectively inhibited by the PI3K inhibitor GDC-0941" *Cancer Cell* 15(5) :429-40 (May 5, 2009).
Junutula et al., "Site-specific conjugation of a cytotoxic drug to an antibody improves the therapeutic index" *Nat Biotechnol.* 26(8):925-32 (Aug 2008).
Krop et al., "A Phase I Study of Trastuzumab-DM1, a First-in-Class HER2 Antibody-Drug Conjugate (ADC), in Patients with HER2+Metastatic Breast Cancer (Poster 2118) " (European Cancer Conference ECCO, Sep. 23-27, 2007, Barcelona) pps. 1 page.
Lee-Hoeflich et al., "A central role for HER3 in HER2—amplified breast cancer: implications for targeted therapy" *Cancer Research* 68(14) :5878-87 (Jul 15, 2008).
Lewis Phillips et al., "Targeting HER2—positive breast cancer with trastuzumab-DM1, an antibody-cytotoxic drug conjugate" *Cancer Research* 68(22):9280-90 (Nov 15, 2008).
Pegram et al., "Inhibitory effects of combinations of HER-2/neu antibody and chemotherapeutic agents used for treatment of human breast cancers" *Oncogene* 18:2241-2251 (1999).
Pegram et al., "Rational combinations of trastuzumab with chemotherapeutic drugs used in the treatment of breast cancer" *Journal of the National Cancer Institute* 96(10):739-749 (May 19, 2004).
Vogel et al., "A Phase II Study of Trastuzumab-DM1 (T-DM1), A HER2 Antibody-Drug Conjugate, in Patients with HER2 Positive Metastatic Breast Cancer (Poster 1017)" (ASCO Amer. Soc. Clinical Oncology, Orlando FL, May 29, 2009) pps. 1 page.
Aasland et al., "Expression of Oncogenes in Thyroid Tumours Coexpression of c-erbB2/neu and c-erbB", Br. J. Cancer, vol. 57, pp. 358-363 (1988).
Apelgren et al., Cancer Research, 50: 3540-3544 (1990).
Arteaga, C. L., et al., "p185[613-2] Signaling Enhances Cisplatin-Induced Cytotoxicity in Human Breast Carcinoma Cells: Association Between an Oncogenic Receptor Tyrosine Kinase and Drug-Induced DNA Repair" Cancer Research, vol. 54, pp. 3758-3765 (1994).
Bacus et al., "Differentiation of Cultured Human Breast Cancer Cells (AU-565 and MCF-7) Associated with Loss of Cell Surface HER-2/neu Antigen", Molecular Carcinogenesis, vol. 3, pp. 350-362 (1990).
Bacus, S. S. et al., "Tumor-inhibitory Monoclonals Antibodies to the HER-2/Neu Receptor Induce Differentiation of Human Breast Cancer Cells", Cancer Research, vol. 52, pp. 2580-2589 (1992).
Bai et al., Cancer Research, 56:4398-4406 (1996).
Baselga et al., "Phase H Study of Weekly Intravenous Recombinant Humanized Anti-p185[HER2]Monoclonal Antibody in Patients with HER2/neu Overexpressing Metastatic Breast Cancer", J. Clin. Oncol., vol. 14, pp. 737-744 (1996).
Borst et al., "Oncogene Alterations in Endometrial Carcinoma", Gynecol. Oncol., vol. 38, pp. 364- 366 (1990).
Burris, "Docetaxel (Taxotere) in Her-2—positive patients and in combination with Trastuzumab (Herceptin)", Seminars in Oncology, 27(No. 2, Suppl. 3):19-23 (2000).
Carter et al., "Humanization of anti-p.185[}4ER2] Antibody for Human Cancer Therapy", Proc. Natl. Acad. Sci. USA. vol. 89, pp. 4285-4289 (1992).
Chan et al., "Synergistic effects of doxorubicin and modulators of multidrug resistance in small cell lung cancer (SCLC) cells naturally expressing MDR-1, MRP and LRP phenotypes", Proceedings Am. Assoc. for Cancer Res., 38: 591-592 (1997).
Chari et al., "Dose-response of the anti-tumor effect of huN901-DM1 against human small-cell lung cancer xenografts", Proceedings of the American Association for Cancer Research, 41: 693 (2000).
Christian et al., Gynecologic Oncology, 55:s143-s150 (1994).
Cobleigh et al., "Multinational Study of the Efficacy and Safety of Humanized Anti-HER2 Monoclonal Antibody in Women Who Have HER2—Overexpressing Metastatic Breast Cancer that has Progressed after Chemotherapy for Metastatic Disease", J. Clin. Oncol., vol. 17, pp. 2639-2648 (1999).
Cohen et al., "Expression Pattern of the neu (NGL) Gene-Coded Growth factor Receptor Protein (3185.e.) in Normal and Transformed Epithelial Tissues of the Digestive Tract", Oncogene, vol. 4, pp. 81-88 (1989).
Dieras et al., 10th NCI-EORTC Symposium on New Drugs in Cancer Therapy, p. 100, Abstract Nos. and 383 (Jun. 1998).
Doria et al., Cancer, 62:1939-1945 (1988).
Drebin et al., "Down-Modulation of an Oncogene Protein Product and Reversion of the Transformed Phenotype by Monoclonal Antibodies", Cell, vol. 41, pp. 695-706 (1985).
Drebin et al., "Monoclonal Antibodies Reactive with Distinct Domains of the neu Oncogene-Encoded p185 Molecule Exert Synergistic Anti-tumor Effects in Vivo", Oncogene, vol. 2, pp. 273- 277 (1988).
D'Souza et al., "Overexpression of ERBB2 in Human Mammary Epithelial Cells Signals Inhibition of Transcription of the E-cadherin Gene", Proc. Natl. Acad. Sci., USA, vol. 91, pp. 7202-7206 (1994).
Embleton et al., Br. J. Cancer, 47:043-049 (1993).
Erickson H.K et al., "Antibody-Maytansinoid Conjugates are acevated in targeted cancer cells by Lysosomal degradation and Linker-Dependent Intracellular Processing", Cancer Res. 66: (8), pp. 4426- 4433, (2006).
Fedier et al., Annals of Oncology, 14:938-945 (2003).
Fendly, B. M. et al., "Characterization of Murine Monoclonal Antibodies Reactive to Either the Human Epidermal Growth Factor Receptor or HER2/neu Gene Product", Cancer Research, vol. 50, pp. I550-1558 (1990).
Fiorentino et al., Dev. Oncol., 54:415-435 (1988).
Fitzpatrick et al., International Immunopharmacology, 3: 1699-1714 (2003).
Fornier et al., "Update on the management of advanced breast cancer", Oncology, 13(5):647-658 (1999).
Fukushige et al., "Localization of a Novel v-erbB-Related Gene, c-erbB-2, on Human Chromosome 17 and its Amplification in a Gastric Cancer Cell Line", Molecular and Cellular Biology, vol. 6, No. 3, pp. 955-958 (1986).
Fundamental Immunology 242 (William E Paul, M.D. ed., 3rd ed. 1993) p. 242.
Ghaemmaghami et al., Chest, 113(Supp. 1):86s-91s (1998).
Gianni et al., "Putting taxanes to work in operable breast cancer: a search for selective indications from empirical studies", Recent Results in Cancer Research, 152:314-322 (1998).
Glisson et al., Journal of Clinical Oncology, 17(8):2309-2315 (1999).
Griffin et al., The Journal of Immunology, 130(6):2947-2951 (1983).
Gu et al., "Overexpression of her-2/neu in Human Prostate Cancer and Benign Hyperplasia", Cancer Letters, vol. 99, pp. 185-189 (1996).
Gu et al., "Synergistic effect of paclitaxel and 4-hydroxytamoxifen on estrogen receptor-negative colon cancer and lung cancer cell lines", Anti-Cancer Research, 10(10):895-901 (1999).
Guchelaar et al., Clinical Oncology, 6:40-48 (1994).
Guerin et al., "Overexpression of Either c-myc or c-erbB-2/neu Proto-Oncogenes in Human Breast Carcinomas: Correlation with Poor Prognosis" Oncogene Research, vol. 3, pp. 21-31 (1988).
Gupta, "Cross-Resistance of Vinblastine and Taxol-Resistant Mutants of Chinese Hamster Ovary Cells to Other Anticancer Drugs." Cancer Treatment Reports, 69(5):515-521 (1985).
Hancock, M.C. et al., A Monoclonal Antibody Against the c-erbB-2 Protein Enhances the Cytotoxicity of cis-Diamminedichloroplatinum Against Human Breast and Ovarian Tumor Cell Lines:, vol. 51, pp. 4575- 4580 (1991).
Harweth et al., "Monoclonal Antibodies Against the Extracelluler Domain of the erbB-2 Receptor Function as Partial Ligand Agonists", The Journal of Biological Chemistry, vol. 267, No. 21, pp. 15160-15167 (1992).
Hortobagyi, "Docetaxel in breast cancer and a rationale for combination therapy", Oncology, 11(6):11-15 (1997).
Hortobagyi, "Recent progress in clinical development of doxetaxel (Taxotere)", Seminars in Oncology, 26(No. 3, Suppl. 9):32-36 (1999).

(56) References Cited

OTHER PUBLICATIONS

Hudziak et al., "p185$^{HER2}$ Monoclonal Antibody has Antiproliferative Effects in Vitro Effects in Vitro and Sensitizes Huamn Breast Tumor Cells to Tumor Necrosis Factor", Molecular and Cellular Biology, vol. 9, No. 3, pp. 1165-1172 (1989).
ImmunoGen, Inc., Press Release (Feb. 25, 1999).
Iwasaki et al., Yakugaku Zasshi, 118:111-126 (1998).
Jordan et al., "Tubulin as a Target for Anticancer Drugs: Agents Which Interact with the Mitotic Spindle." Medicinal Research Reviews, 18(4):259-296 (1998).
Karsprzyk, P. G. et al., "Therapy of an Animal Model of Human Gastric Cancer Using a Combination of Anti-erbB-2 Monoclonals Antibodies", Cancer Research, vol. 52, pp. 2771-2776 (1992).
Kaufman et al., "Utility of 123C3 monoclonal antibody against CD56 (NCAM) for the diagnosis of small cell carcinomas on paraffin sections", Human Pathology, 28(12):1373-1378 (1997).
Kawai et al., "Chemical Modification of Ansamitocins. III. Synthesis and Biological Effects of 3-Acyl Esters of Maytansinol,", Chemical and Pharmaceutical Bulletin, 32(9): 3441-3451 (1984).
Kern, J. A. et al., "p185$^{11}$ Expression in Human Lung Adenocarcinomas Predicts Shortened Survival", Cancer Research, vol. 50, pp. 5184-5191 (1990).
Kibbelaar et al., Journal of Pathology, 159:23-28 (1989).
King et al., "Amplification of a Novel v-erbB-Related Gene in a Human Mammary Carcinoma", Science, vol. 229, pp. 974-976 (1985).
Kraus et al., Isolation and Characterization of ERBB3, a Third Member of the ERBB/epidermal Growth Factor Receptor Family: Evidence for Overexpression in a Subset of Human Mammry Tumors: Proc. Natl. Acad. Sci. USA, vol. 86, pp. 9193-9197 (1989).
Krek et al., "Expression and secretion of a recombinant ricin immunotoxin from murine myeloma cells", Protein Engineering, 8(5):481-489 (1995).
Kumar et al., "Regulation of Phosphorylation of the c-erbB-2/HER2 Gene Product by a Monoclonal Antibody and Serum Growth Factor(s) in Human Mammry Carcinoma Cells", Molecular and Cellular Biology, vol. 11, No. 2, pp. 979-986 (1991).
Laguzza et al., J. Med. Chem., 32: 548-555 (1989).
Lewis et al., "Differential Responses of Human Tumor Cell Lines to Anti-p185$^{HER2}$ Monoclonal Antibodies", Cancer Immunol. Immunother, vol. 37, pp. 255-263 (1993).
Lewis, G.D. et al., "Growth Regulation of Human Breast and Ovarian Tumor Cells by Heregulin: Evidence for the Requirement of ErbB2 as a Critical Component in Mediating Heregulin Responsiveness" Cancer Research, vol. 56, pp. 1457-1465 (1996).
Lidor et al., Journal of Clinical Investigation, 92:2440-2447 (1993).
Liu et al., "Cure of large human colon cancer xenografts by a C242-maystansinoid conjugate", Proceedings of the American Association for Cancer Research, 37(2):466-467 (1996b).
Liu et al., "Eradication of Large Colon Tumor Xenografts b Targeted Delivery of Maytansinoids", Proc. Natl. Acad. Sci. USA, vol. 93, pp. 8618-8623 (1996).
Liu et al., "The development of antibody delivery systems to target cancer with highly potent maystansinoids", Exp. opin. Invest. Drugs, 6(2):169-172 (1997b).
Liu et al., Proc. Annu. Meet. Am. Assoc. Cancer Res., 38:29 (1997a).
Lynch et al., "Immunotoxin therapy of small-cell lung cancer: a phase I study of N901-blocked ricin", Journal of Clinical Oncology, 15(2):723-734 (1997).
Maier, L. A. et al., "Requirements for the Internalization of a Murine Monoclonal Antibody Directed Against the Her-2/neu Gene Product c-erbB-2" Cancer Research, vol. 51, pp. 5361-5369 (1991).
Mandler et al., "Synthethsis and Evaluation of Antiproliferative Activity of a Geldanamycin-herceptin Immunoconjugate", Bioorganic and Medicinal Chem. Letters, 10:1025-1028 (2000).
McCann et al., "c-erbB-2 Oncoprotcin Expression in Primary Human Tumors", Cancer, vol. 65, pp. 89-92 (1990).
McKenzie et al., "Generation and Characterization of Monoclonal Antibodies Specific for the Human neu Oncogene Product, pl 85", Oncogene, vol. 4, pp. 543-548 (1989).

Mendelsohn et al., Clin. Cancer Res., 3:2703-2707 (1997).
Milas et al, "Enhancement of tumor radioresponse of a murine mammary carcinoma by paclitaxel", Cancer Research, 54(13):3560-3510 (1994).
Morikawa et al., "Pulmonary malignant fibrous histiocytoma treated with cisplatin plus etoposide followed by surgery", Nihon Kyobu Shikkan Gakkai Zasshi, Japanese Journal of Thoracic Diseases, 33(9):993-998 (1995).
Morris et al., Journal of Clinical Oncology, 16(3):1094-1098 (1998).
Myers et al., "Biological Effects of Monoclonal Antireceptor Antibodies Reactive with neu Oncogene Product, p185", Methods in Enzymology, vol. 198, pp. 277-290 (1991).
Nakajima et al., "Increase in the Chemically-Induced Differentiation of Human Leukemia Cell Lines by Tubulin Disruptors."Biol. Pharm. Bull., 17(5):742-744 (1994).
Nguyen et al., "Synergistic tumoricidal effect of the paclitaxel and 17 allylernino geldanamycin (17AAG) combination in non-small cell lung cancer: in vitro and in vivo'analysis", Proceedings of the Am. Assoc. for Cancer Research, 42:68-69 (2001).
Niculescu-Duvaz and Springer, "Antibody-Directed Enzyme prodrug Therapy (ADEPT): A Review" Adv. Drq. Del. Rev. 26: 151-172, (1997).
Norton et al., "Overall survival (OS) advantage to simultaneous chemotherapy (CRx) plus the humanized anti-HER2 monoclonal antibody Herceptin (H) in HER2-overexpressing (HER2+)", Proc. Annu. Meet. Am. Soc. Clin. Oncol., 18:A483 (1999).
Panda et al., Proc. Natl. Acad. Sci. USA, 95: 9313-9318 (1998).
Park, Joo-Bae et al., "Amplification, Overexpression, and Rearrangement of the erbB-2 Protooncogene in Primary Human Stomach Carcinomas", Cancer Research, vol. 49, pp. 6605-6609 (1989).
Payne, Gillian, "Progress in Immunoconjugate Cancer Therapeutics" Cancer Cell 3: 207-212, (2003).
Perez, "Current management of metastatic breast cancer", Seminars in Oncology, 26(No. 4, Suppl. 12):1-10 (1999a).
Perez, "Paclitaxel plus nonathracycline combinations in metastatic breast cancer, Seminars in Oncology" , 26(No. 1, Suppl. 2):21-26 (1999b).
Pettitt et al., J. Am. Chem. Soc., 111:5463-5465 (1989).
Pietras et al., "Antibody to Her-2/neu Receptor Blocks DNA Repair after Cisplatin in Human Breast and Ovarian Cancer Cells", Oncogene, vol. 9, pp. 1829-1838 (1994).
Pitot et al., Clinical Cancer Research, 5:525-531 (1999).
Plowman et al., "Heregulin Induces Tyrosine Phosphorylation of HER4/P180$^{ERBb4}$", Letters to Nature, vol. 366, pp. 473-475 (1993).
Plowman et al., "Ligand-specific Activation of HER4/p180'$^{6B4}$, a Fourth Member of the Epidermal Growth Factor Receptor Family", Proc. Natl. Acad. Sci. USA, vol. 90, pp. 1746-1750 (1993).
Queen, et al., "A Humanized antibody that binds to the interleukin 2 receptor", Proc. Natl. Acad. Sci. USA, vol. 86, pp. 10029-10033, Dec. 1989.
Roguska et al., "A comparison of two murine monoclonal antibodies humanized by CDR-grafting and variable domain resurfacing", Protein Engineering, 9(10):895-904 (1996).
Roguska et al., "Humanization of murine monoclonal antibodies through variable domain resurfacing", Proceedings of the National Academy of Sciences USA, 91(3):969-973 (1994).
Rosenblum et al., Cancer Immunol Immunother, 42: 115-121 (1996).
Ross et al., "Her-2/neu Gene Amplification Status in Prostate Cancer by Fluorescence in Situ Hybridization", Human Pathology, vol. 28, no. 7, pp. 827-833 (1997).
Ross et al., "Prognostic Significance of HER-21neu Gene Amplification Status by Fluorescence in Situ Hybridization of Prostate Carcinoma", Cancer, vol. 79, pp. 2162-2170 (1997).
Ross et al., "Prostate Stem Cell Antigen as Therapy Target: Tissue Experssion and in Vivo Efficacy of an Immunoconjugate" Cancer Research, 62: 2546-2553, (2002).
Roy et al., "Elimination of neuroblastoma and small-cell lung cancer cells with an anti-neural cell adhesion molecule immunotoxin", Journal of the National Cancer Institute, 88(16):1136-1145 (1996).
Rygaard et al., Br. J. Cancer, 65:573-577 (1992).
Sadasivan et al., "Overexpression of HER-2/NEU May be an Indicator of Poor Prognosis in Prostate Cancer", The Journal of Urology, vol. 150, pp. 126-131 (1993).

(56) References Cited

OTHER PUBLICATIONS

Sarup, J. C. et al., "Characterization of an Anti-p185$^{HER2}$ Monoclonal Antibody that Stimulates Receptor Funcion and Inhibits Tumor Cell Growth ", Growth Regulation, vol. 1, pp. 72-82 (1991).
Schaefer et al., "7-Heregulin: A Novel Heregulin Isoform that is an Autocrine Growth Factor for the Human Breast Cancer Cell Line, MDA-MB-175", Oncogene, vol. 15, pp. 1385-1394 (1997).
Schlom, "Monoclonal Antibodies: They're More and Less Than You Think, In: Molecular Foundations of Oncology", Ed. S. Broder, pp. 95-134 (1991).
Schrappe et al., Cancer Research, 52:3838-3844 (1992).
Scott et al., "p185$^{HER2}$ Signal Transduction in Breast Cancer Cells", The Journal of Biological Chemistry, vol. 266, No. 22, pp. 14300-14305 (1991).
Shawver, L. K. et al., "Ligand-like Effects Induced by Anti-c-erbB2 Antibodies Do Not Correlate with and Are Not Required for Growth Inhibition of Human Carcinoma Cells", Cancer research, vol 54, pp. 1367-1373 (1994).
Shepard et al., "Monoclonal Antibody Therapy of Human Cancer: Taking the HER2 Protoocogene to the Clinic", Journal of Clinical Immunology, vol. 11, No. 3 (1991).
Siegall et al., Proc. Annu. Meet. Am. Assoc. Cancer Res., 38:A185 (1997).
Slamon et al., "Human Breast Cancer: Correlation of Relapse and Survival with Amplification of the HER2/neu Oncogene", Science, vol. 235, pp. 177-182 (1987).
Slamon et al., "Studies of the HER-2/neu Proto-Oncogene in Human Breast and Ovarian Cancer", Science, vol. 244, pp. 707-712 (1989).
Sliwkowski et al., "Coexpression of erbB2 and erbB3 Proteins Reconstitutes a High Affinity Receptor for Heregulin", the Journal of Biological Chemistry, vol. 269, No. 20, pp.14661-1665 (1994).
Smith et al., Cancer Research, 54:3779-3784 (1994).
Souhami, "The antigens of lung cancer", Thorax, 47: 53-56, (1992).
Spector et al., "Study of the Biologic Effects of Lapatinib, a Reversible Inhibitor of ErbB1 and ErbB2 Tyrosine Kinases, on Tumor Growth and Survival pathways in Patients With Advanced Malignancies, " Jour. of Clin. Onc. 23(11):2502-2512 (2005).
Stancovski et al., "Mechanistic Aspects of the Opposing Effects of Monoclonal Antibodies to the ERBB2 Receptor on Tumor Growth", Proc. Natl. Acad. Sci. USA, vol. 88, pp. 8691-8695 (1991).
Syrigos, K. N. et and al., "Antibody Directed Enzyme Prodrug Therapy (ADEPT): A Review of the Experimental Clinical Considerations" Anticancer Research 19: 605-614, (1999).
Tagliabue et al., "Selection of Monoclonal Antibodies which Induce Internalization and Phosphorylation of p185$^{HER2}$ and Growth Inhibition of Cells with HER2/NEU Gene Amplification", Int. J. Cancer, vol. 47, pp. 933-937 (1991).
Tolcher et al., "Cantuzumab Mertansine, a Maytansinoid Immunoconjugate Directed to the CanAg Antigene: A Phase 1, Pharmacokinetic, and Biologic Correlative Studay" Journal of Clinical Oncology 21: 211-222, (2003).
Trail et al., "Enhanced antitumor activity of paclitaxel in combination with the anticarcinoma immunoconuugate BR96-doxorubicin", Clincal Cancer Research, 5(11): 3632-3638 (1999).
Trail et al., "Effect of linker variation on the stability, potency, and efficacy of carcinoma-reactive BR64-doxorubicin immunoconjugates" Cancer Research 57(1):100-105, (1997).

Villalona-Calero, Journal of Clinical Oncology, 16(8):2770-2779 (1998).
Vitetta, E. S. et al., "Monoclonal Antibodies as Agonists: An Expanded Role for their Use in Cancer Therapy", Cancer Research, vol. 54, pp.5301-5309 (1994).
Vogel et al., "Monotherapy of metastatic breast cancer: a review of newer agents", Oncologist, 4(1):17-33 (1999).
Watson et al., Proc. Annu. Meet. Am. Assoc. Cancer Res., 37:A2997 (1996).
Weiner, D. B. et al., "Expression of the neu Gene-encoded Protein (P185) in Human Non-Small Cell Carcinomas of the Lung", Cancer Research, vol. 50, pp. 421-425 (1990).
Williams et al., "Expression of c-erbB-2 in Human Pancreatic Adenocarcinomas", Pathobiology, vol. 59, pp. 46-52 (1991).
Xie et al, "Pharmacokinetics and biodistribution of the antitumor immunoconjugate, cantuzumab mertansine (huC242-DM1), and its two components in mice" J pharmacol Exp Ther. 308(3): 1073-1082, (2004).
Xu et al. (Clinical Cancer Research vol. 3(9), pp. 1629-1634, 1997).
Yeh et al., "Growth inhibitory action of brefeldin A with taxol and tiazofurin in human breast carcinoma cells", Cancer Biochemistry Biophysics, 15(1):11-17 (1995).
Yokota, J. et al., "Amplification of c-erbB2 Oncogene in Human Adenocarcinomas in Vivo", The Lancet, vol. 1, pp. 765-767 (1986).
Yonemura, Y. et al., "Evaluation of Immunoreactivity for crbB-2 Protein as a Marker of Poor Short Term Prognosis in Gastric Cancer", Cancer Research, vol. 51, pp. 1034-1038 (1991).
Zhau et al., "Amplification and Expression of the c-erb B-2/neu Proto-Oncogene in Human Bladder Cancer", Molecular Carcinogenesis, vol. 3, pp. 254-257 (1990).
U.S. Appl. No. 13/305,042, filed Nov. 28, 2011, Blatter et al.
Junttilla, T et al. "Trastuzumab-DM1 (T_DM1) retains all the mechanisms of action of trastuzumab and efficiently inhibits growth of lapatinib insensitive breast cancer" *Breast Cancer Res Treat* 128:347-356 (2011).
Examination Report received in corresponding JP Application No. 2009-550630.
AACR 98$^{th}$ Annual Meeting Apr. 14-18, 2007, abstract #651.
AACR 98$^{th}$ Annual Meeting Apr. 14-18, 2007, abstract #1554 '.
Burris, H. "Initial trials with next-generation trastuzumab DMl(Herceptin)", P&T 32(12):677, 2007.
Brocichoff, et al. "Differential impact of Cetuximab, Pertuzuma and Trastuzumab on BT474 and SK-BR-3 breast cancer cell proliferation", Cell Prolife 40,488-507, 2007.
Giamas, G. et al. "Protein kinases as targets for cancer treatment", Pharmacogenomics 8(8):1005-1016, 2007.
Ito, Y. et al. "Lapatinib: ErbB/HER1 and 2", Japanese J. Breast Cancer 20(3)211-215, 2005 (with English abstract).
Kan, N. et al. "Stratification with respect to hormone receptor and HER2/neu in the treatment of metastatic breast cancer: sensitivity to taxane", Japanese Journal of Cancer and Chemotherapy 34(1):53-57, 2007 (with English abstract).
Pegram, M. et al. "Trastuzumab and chemotherapeutics: drug interactions and synergies", Seminars in Oncology 27(6):21-25, Dec 2000.
Wardley et al. "Safety of pertuzumab plus trastuzumab in a phase II trial of patients with HER2—overexpressing metastatic breast cancer which had progressed during trastuzumab therapy", Breast Cancer Research Treatment 106:S19, 73, 2007.

\* cited by examiner

COMBINATIONS OF AN ANTI-HER2 ANTIBODY-DRUG CONJUGATE AND CHEMOTHERAPEUTIC AGENTS, AND METHODS OF USE

CROSS REFERENCE TO RELATED APPLICATIONS

This non-provisional application filed under 37 CFR §1.53 (b), claims the benefit under 35 USC §119(e) of U.S. Provisional Application Ser. No. 61/037,410 filed on 18 Mar. 2008, which is incorporated by reference in entirety.

FIELD OF THE INVENTION

The invention relates generally to pharmaceutical combinations of compounds with activity against hyperproliferative disorders such as cancer. The invention also relates to methods of using the combinations of compounds for in vitro, in situ, and in vivo diagnosis or treatment of mammalian cells, or associated pathological conditions.

BACKGROUND OF THE INVENTION

The HER2 (ErbB2) receptor tyrosine is a member of the epidermal growth factor receptor (EGFR) family of transmembrane receptors. Overexpression of HER2 is observed in approximately 20% of human breast cancers and is implicated in the aggressive growth and poor clinical outcomes associated with these tumors (Slamon et al (1987) Science 235:177-182).

Trastuzumab (CAS 180288-69-1, HERCEPTIN®, huMAb4D5-8, rhuMAb HER2, Genentech) is a recombinant DNA-derived humanized, IgG1 kappa, monoclonal antibody version of the murine HER2 antibody which selectively binds with high affinity in a cell-based assay (Kd=5 nM) to the extracellular domain of the human epidermal growth factor receptor2 protein, HER2 (ErbB2) (U.S. Pat. No. 5,677,171; U.S. Pat. No. 5,821,337; U.S. Pat. No. 6,054,297; U.S. Pat. No. 6,165,464; U.S. Pat. No. 6,339,142; U.S. Pat. No. 6,407,213; U.S. Pat. No. 6,639,055; U.S. Pat. No. 6,719,971; U.S. Pat. No. 6,800,738; U.S. Pat. No. 7,074,404; Coussens et al (1985) Science 230:1132-9; Slamon et al (1989) Science 244:707-12; Slamon et al (2001) New Engl. J. Med. 344:783-792). Trastuzumab contains human framework regions with the complementarity-determining regions of a murine antibody (4D5) that binds to HER2. Trastuzumab binds to the HER2 antigen and thus inhibits the growth of cancerous cells. Trastuzumab has been shown, in both in vitro assays and in animals, to inhibit the proliferation of human tumor cells that overexpress HER2 (Hudziak et al (1989) Mol Cell Biol 9:1165-72; Lewis et al (1993) Cancer Immunol Immunother; 37:255-63; Baselga et al (1998) Cancer Res. 58:2825-2831). Trastuzumab is a mediator of antibody-dependent cellular cytotoxicity, ADCC (Lewis et al (1993) Cancer Immunol Immunother 37(4):255-263; Hotaling et al (1996) [abstract]. Proc. Annual Meeting Am Assoc Cancer Res; 37:471; Pegram M D, et al (1997) [abstract]. Proc Am Assoc Cancer Res; 38:602; Sliwkowski et al (1999) Seminars in Oncology 26(4), Suppl 12:60-70; Yarden Y. and Sliwkowski, M. (2001) Nature Reviews Molecular Cell Biology, Macmillan Magazines, Ltd., Vol. 2:127-137).

HERCEPTIN® was approved in 1998 for the treatment of patients with ErbB2-overexpressing metastatic breast cancers (Baselga et al, (1996) J. Clin. Oncol. 14:737-744) that have received extensive prior anti-cancer therapy, and has since been used in over 300,000 patients (Slamon D J, et al. N Engl J Med 2001; 344:783-92; Vogel C L, et al. J Clin Oncol 2002; 20:719-26; Marty M, et al. J Clin Oncol 2005; 23:4265-74; Romond E H, et al. T N Engl J Med 2005; 353:1673-84; Piccart-Gebhart M J, et al. N Engl J Med 2005; 353:1659-72; Slamon D, et al. [abstract]. Breast Cancer Res Treat 2006, 100 (Suppl 1): 52). In 2006, the FDA approved HERCEPTIN® (trastuzumab, Genentech Inc.) as part of a treatment regimen containing doxorubicin, cyclophosphamide and paclitaxel for the adjuvant treatment of patients with HER2-positive, node-positive breast cancer. While the development of HERCEPTIN® provided patients with HER2-positive tumors a markedly better outcome than with chemotherapy alone, virtually all HER2-positive, metastatic breast cancer (MBC) patients will eventually progress on available therapies. Opportunities remain to improve outcomes for patients with MBC. Despite trastuzumab's diverse mechanisms of action, a number of patients treated with trastuzumab show either no response or stop responding after a period of treatment benefit. Some HER2+ (HER2 positive) tumors fail to respond to HERCEPTIN® and the majority of patients whose tumors respond eventually progress. There is a significant clinical need for developing further HER2-directed cancer therapies for patients with HER2-overexpressing tumors or other diseases associated with HER2 expression that do not respond, or respond poorly, to HERCEPTIN® treatment.

An alternative approach to antibody-targeted therapy is to utilize antibodies for delivery of cytotoxic drugs specifically to antigen-expressing cancer cells. Maytansinoids, derivatives of the anti-mitotic drug maytansine, bind to microtubules in a manner similar to vinca alkaloid drugs (Issell B F et al (1978) Cancer Treat. Rev. 5:199-207; Cabanillas F et al. (1979) Cancer Treat Rep, 63:507-9. Antibody-drug conjugates (ADCs) composed of the maytansinoid DM1 linked to trastuzumab show potent anti-tumor activity in HER2-overexpressing trastuzumab-sensitive and trastuzumab-resistant tumor cell lines, and xenograft models of human breast cancer. A conjugate of maytansinoids linked to the anti-HER2 murine breast cancer antibody TA.1 via the MCC linker was 200-fold less potent than the corresponding conjugate with a disulfide linker (Chari et al (1992) Cancer Res. 127-133). Antibody-drug conjugates (ADCs) composed of the maytansinoid, DM1, linked to trastuzumab show potent anti-tumor activity in HER2-overexpressing trastuzumab-sensitive and -resistant tumor cell lines and xenograft models of human cancer. Trastuzumab-MCC-DM1 (T-DM1) is currently undergoing evaluation in phase II clinical trials in patients whose disease is refractory to HER2-directed therapies (Beeram et al (2007) "A phase I study of trastuzumab-MCC-DM1 (T-DM1), a first-in-class HER2 antibody-drug conjugate (ADC), in patients (pts) with HER2+ metastatic breast cancer (BC)", American Society of Clinical Oncology 43rd: June 2 (Abs 1042; Krop et al, European Cancer Conference ECCO, Poster 2118, Sep. 23-27, 2007, Barcelona; U.S. Pat. No. 7,097,840; US 2005/0276812; US 2005/0166993).

Combination therapy in which two or more drugs are used together in some dosing regimen or administration form, typically has one or more goals of: (i) reducing the frequency at which acquired resistance arises by combining drugs with minimal cross-resistance, (ii) lowering the doses of drugs with non-overlapping toxicity and similar therapeutic profile so as to achieve efficacy with fewer side effects, i.e. increase therapeutic index, (iii) sensitizing cells to the action of one drug through use of another drug, such as altering cell-cycle stage or growth properties, and (iv) achieving enhanced potency by exploiting additivity, or greater than additivity, effects in the biological activity of two drugs (Pegram, M., et al (1999) Oncogene 18:2241-2251; Konecny, G., et al (2001)

Breast Cancer Res. and Treatment 67:223-233; Pegram, M., et al (2004) J. of the Nat. Cancer Inst. 96(10):739-749; Fitzgerald et al (2006) Nature Chem. Biol. 2(9):458-466; Borisy et al (2003) Proc. Natl. Acad. Sci. 100(13):7977-7982).

Loewe additivity (Chou, T. C. and Talalay, P. (1977) J. Biol. Chem. 252:6438-6442; Chou, T. C. and Talalay, P. (1984) Adv. Enzyme Regul. 22:27-55; Berenbaum, M. C. (1989) Pharmacol. Rev. 41:93-141) and Bliss independence/synergy (Bliss, C. I. (1956) Bacteriol. Rev. 20:243-258; Greco et al (1995) Pharmacol. Rev. 47:331-385) are methods used for calculating the expected dose-response relationship for combination therapy compared to monotherapy based on parameters such as IC50, the dose of drug needed to achieve 50% target inhibition and equal to Ki in the simplest case.

HER2 dimerization inhibitor antibodies and EGFR inhibitors have been reported for combination therapy against cancer (US 2007/0020261). Trastuzumab-MCC-DM1 (T-DM1) and pertuzumab have individually demonstrated activity in MBC patients, and a combination of pertuzumab and trastuzumab has been shown to be active in HER-positive MBC patients (Baselga J, et al. "A Phase II trial of trastuzumab and pertuzumab in patients with HER2-positive metastatic breast cancer that had progressed during trastuzumab therapy: full response data", European Society of Medical Oncology, Stockholm, Sweden, Sep. 12-16, 2008).

SUMMARY OF THE INVENTION

The invention relates generally to the anti-HER2 antibody-drug conjugate, trastuzumab-MCC-DM1, administered in combination with one or more chemotherapeutic agents to inhibit the growth of cancer cells. Certain combinations of trastuzumab-MCC-DM1 and a chemotherapeutic agent show synergistic effects in inhibiting the growth of cancer cells in vitro and in vivo. The combinations and methods of the invention may be useful in the treatment of hyperproliferative disorders such as cancer. The combinations may inhibit tumor growth in mammals and may be useful for treating human cancer patients.

In one aspect, the invention includes a method for the treatment of a hyperproliferative disorder comprising administering a therapeutic combination as a combined formulation or by alternation to a mammal, wherein the therapeutic combination comprises a therapeutically effective amount of trastuzumab-MCC-DM1, and a therapeutically effective amount of a chemotherapeutic agent selected from a HER2 dimerization inhibitor antibody, an anti-VEGF antibody, 5-FU, carboplatin, lapatinib, ABT-869, docetaxel, GDC-0941, and GNE-390.

The therapeutically effective amount of trastuzumab-MCC-DM1 and the therapeutically effective amount of the chemotherapeutic agent may be administered as a combined formulation or by alternation.

The invention also relates to methods of using the compositions for in vitro, in situ, and in vivo diagnosis or treatment of mammalian cells, organisms, or associated pathological conditions.

The invention also relates to methods wherein administration of the therapeutic combination results in a synergistic effect.

Another aspect of the invention are pharmaceutical compositions comprising trastuzumab-MCC-DM1, a chemotherapeutic agent selected from a HER2 dimerization inhibitor antibody, an anti-VEGF antibody, 5-FU, carboplatin, lapatinib, ABT-869, docetaxel, GDC-0941, and GNE-390; and one or more pharmaceutically acceptable carrier, glidant, diluent, or excipient.

Another aspect of the invention provides methods of treating a hyperproliferative disease or disorder, comprising administering to a mammal in need of such treatment effective amounts of trastuzumab-MCC-DM1 and a chemotherapeutic agent. Trastuzumab-MCC-DM1 and the chemotherapeutic agent may be co-formulated for administration in a combination as a pharmaceutical formulation or they may be administered separately in alternation (alternating, sequential dosages) as a therapeutic combination. In one embodiment, T-DM1 is delivered by infusion and the chemotherapeutic agent is delivered orally.

Another aspect of the invention provides methods to predict effective drug combinations for in vivo efficacy where the combinations include trastuzumab-MCC-DM1 and an anti cancer, standard-of-care, chemotherapeutic agent. Efficacy data from in vitro cell proliferation and in vivo tumor xenograft experiments are analyzed qualitatively and quantitatively. Quantitative analysis methods may be based on the Chou & Talalay median effect and isobolograms generating a combination index (CI) value to denote synergy, antagonism, or additivity, or on the Bliss Independence ribbon graph deflection.

Another aspect of the invention is a method of using a therapeutic combination of the invention to treat a disease or condition such as cancer, including one modulated by HER2 or KDR9 (VEGF receptor 1) in a mammal.

Another aspect of the invention is the use of a therapeutic combination of the invention in the preparation of a medicament for the treatment of a disease or condition such as cancer, including one modulated by HER2 or KDR9 (VEGF receptor 1) in a mammal.

Another aspect of the invention includes articles of manufacture or kits comprising trastuzumab-MCC-DM1, a chemotherapeutic agent, a container, and optionally a package insert or label indicating a treatment.

Another aspect of the invention includes a method for determining compounds to be used in combination for the treatment of cancer comprising: a) administering a therapeutic combination of trastuzumab-MCC-DM1, and a chemotherapeutic agent selected from a HER2 dimerization inhibitor antibody, an anti-VEGF antibody, 5-FU, carboplatin, lapatinib, ABT-869, docetaxel, GDC-0941, and GNE-390 to an in vitro tumor cell line, and b) measuring a synergistic or non-synergistic effect.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

DETAILED DESCRIPTION OF EXEMPLARY EMBODIMENTS

Figure 1:
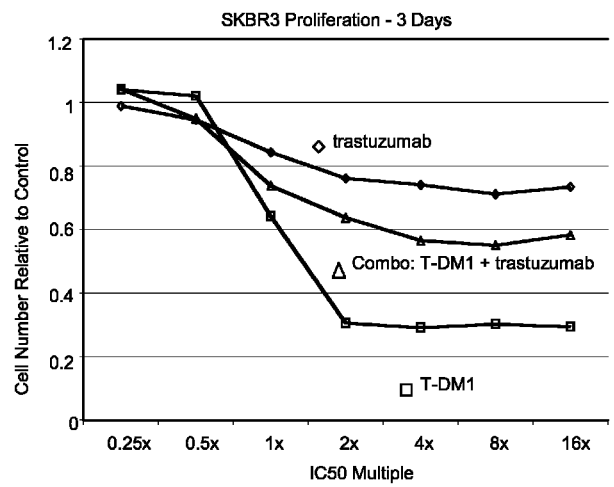
FIG. 1 shows a plot of SK-BR-3 in vitro cell viability at 3 days versus IC50 multiple concentrations of trastuzumab, trastuzumab-MCC-DM1 (T-DM1), and the combination of trastuzumab and T-DM1.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

DEFINITIONS

The words "comprise," "comprising," "include," "including," and "includes" when used in this specification and claims are intended to specify the presence of stated features, integers, components, or steps, but they do not preclude the presence or addition of one or more other features, integers, components, steps, or groups thereof.

The terms "treat" and "treatment" refer to both therapeutic treatment and prophylactic or preventative measures, wherein the object is to prevent or slow down (lessen) an undesired physiological change or disorder, such as the growth, development or spread of a hyperproliferative condition, such as cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

"Hyperproliferative disorder" is indicated by tumors, cancers, and neoplastic tissue, including pre-malignant and non-neoplastic stages, and also include psoriasis, endometriosis, polyps and fibroadenoma.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethyl-ethanamine, NOLVADEX®, ISTUBAL®, VALODEX®), and doxorubicin (ADRIAMYClNO), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (MEK inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclophosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omegaI1 (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (T-2 toxin, verracurin A, roridin A and anguidine); urethan; vindesine; dacarbazine; mannomustine; mitobronitol; mitolactol; pipobroman; gacytosine; arabinoside (Ara-C); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug-conjugate, gemtuzumab ozogamicin (MYLOTARG®, Wyeth).

Humanized monoclonal antibodies with therapeutic potential as chemotherapeutic agents in combination with trastuzumab-MCC-DM1 include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. Acids which are generally considered suitable for the formation of pharmaceutically useful or acceptable salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1 19; P. Gould, International J. of Pharmaceutics (1986) 33 201 217; Anderson et al, The Practice of Medicinal Chemistry (1996), Academic Press, New York; Remington's Pharmaceutical Sciences, 18$^{th}$ ed., (1995) Mack Publishing Co., Easton Pa.; and in The Orange Book (Food & Drug Administration, Washington, D.C. on their website). These disclosures are incorporated herein by reference thereto.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to a physical association or complex of one or more solvent molecules and a compound of the invention. The compounds of the invention may exist in unsolvated as well as solvated forms. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water. This physical association involves varying degrees of ionic and covalent bonding, including hydrogen bonding. In certain instances the solvate will be capable of isolation, for example when one or more solvent molecules are incorporated in the crystal lattice of the crystalline solid. Preparation of solvates is generally known, for example, M. Caira et al, J. Pharmaceutical Sci., 93(3), 601 611 (2004). Similar preparations of solvates, hemisolvate, hydrates and the like are described by E. C. van Tonder et al, AAPS PharmSciTech., 5(1), article 12 (2004); and A. L. Bingham et al, Chem. Commun., 603 604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I.R. spectroscopy, show the presence of the solvent (or water) in the crystals as a solvate (or hydrate).

The term "synergistic" as used herein refers to a therapeutic combination which is more effective than the additive effects of the two or more single agents. A determination of a synergistic interaction between trastuzumab-MCC-DM1, and one or more chemotherapeutic agent may be based on the results obtained from the assays described herein. The results of these assays are analyzed using the Chou and Talalay combination method and Dose-Effect Analysis with CalcuSyn software in order to obtain a Combination Index "CI" (Chou and Talalay (1984) Adv. Enzyme Regul. 22:27-55). The combinations provided by this invention have been evaluated in several assay systems, and the data can be analyzed utilizing a standard program for quantifying synergism, additivism, and antagonism among anticancer agents. The program preferably utilized is that described by Chou and Talalay, in "New Avenues in Developmental Cancer Chemotherapy," Academic Press, 1987, Chapter 2. Combination Index (CI) values less than 0.8 indicate synergy, values greater than 1.2 indicate antagonism and values between 0.8 to 1.2 indicate additive effects. The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially in time.

Trastuzumab-MCC-DM1

The present invention includes therapeutic combinations comprising trastuzumab-MCC-DM1 (T-DM1), an antibody-drug conjugate (CAS Reg. No. 139504-50-0), which has the structure:

quent and manageable. This treatment schedule was well tolerated and associated with significant clinical activity as described previously. A Phase II study has shown similar tolerability at the 3.6 mg/kg dose level administered every 3 weeks, with only a small percentage of patients (3 out of 112 patients) requiring dose reduction. Thus, the T-DM1 dose of 3.6 mg/kg administered every 3 weeks was selected for testing in this study based on 1) the demonstrated efficacy and safety of T-DM1 at 3.6 mg/kg every 3 weeks, and 2) the convenience of a 3-week regimen for this patient population.

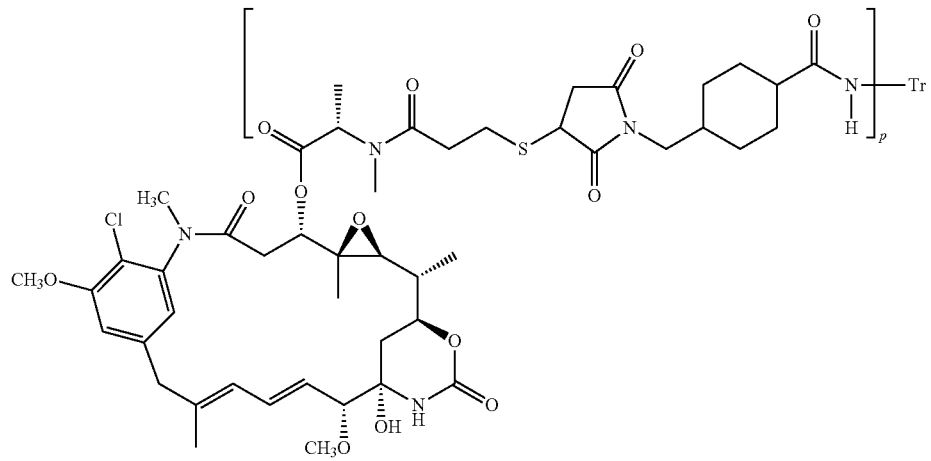

where Tr is trastuzumab, linked through linker moiety MCC, to the maytansinoid drug moiety, DM1 (U.S. Pat. No. 5,208,020; U.S. Pat. No. 6,441,163). The drug to antibody ratio or drug loading is represented by p in the above structure of trastuzumab-MCC-DM1, and ranges in integer values from 1 to about 8. The drug loading value p is 1 to 8. Trastuzumab-MCC-DM1 includes all mixtures of variously loaded and attached antibody-drug conjugates where 1, 2, 3, 4, 5, 6, 7, and 8 drug moieties are covalently attached to the antibody trastuzumab (U.S. Pat. No. 7,097,840; US 2005/0276812; US 2005/0166993). Trastuzumab-MCC-DM1 may be prepared according to Example 1.

Trastuzumab is produced by a mammalian cell (Chinese Hamster Ovary, CHO) suspension culture. The HER2 (or c-erbB2) proto-oncogene encodes a transmembrane receptor protein of 185 kDa, which is structurally related to the epidermal growth factor receptor. HER2 protein overexpression is observed in 25%-30% of primary breast cancers and can be determined using an immunohistochemistry based assessment of fixed tumor blocks (Press M F, et al (1993) Cancer Res 53:4960-70. Trastuzumab is an antibody that has antigen binding residues of, or derived from, the murine 4D5 antibody (ATCC CRL 10463, deposited with American Type Culture Collection, 12301 Parklawn Drive, Rockville, Md. 20852 under the Budapest Treaty on May 24, 1990). Exemplary humanized 4D5 antibodies include huMAb4D5-1, huMAb4D5-2, huMAb4D5-3, huMAb4D5-4, huMAb4D5-5, huMAb4D5-6, huMAb4D5-7 and huMAb4D5-8 (HERCEPTIN®) as in U.S. Pat. No. 5,821,337.

In a Phase I Study, the maximum tolerated dose (MTD) of T-DM1 administered by IV infusion every 3 weeks was 3.6 mg/kg. A DLT (Dose-Limiting Toxicity) consisted of Grade 4 thrombocytopenia in 2 of 3 patients treated at 4.8 mg/kg. Related Grade ≥2 adverse events at 3.6 mg/kg were infre- Chemotherapeutic Agents Certain chemotherapeutic agents have demonstrated surprising and unexpected properties in combination with trastuzumab-MCC-DM1 in inhibiting cellular proliferation in vitro and in vivo. Such chemotherapeutic agents include a HER2 dimerization inhibitor antibody, an anti-VEGF antibody, 5-FU, carboplatin, lapatinib, ABT-869, docetaxel, GDC-0941, and GNE-390.

Pertuzumab (CAS Reg. No. 380610-27-5, OMNITARG®, 2C4, Genentech) is a recombinant, humanized monoclonal antibody that inhibits dimerization of HER2 (U.S. Pat. No. 6,054,297; U.S. Pat. No. 6,407,213; U.S. Pat. No. 6,800,738; U.S. Pat. No. 6,627,196, U.S. Pat. No. 6,949,245; U.S. Pat. No. 7,041,292). Pertuzumab and trastuzumab target different extracellular regions of the HER-2 tyrosine kinase receptor (Nahta et al (2004) Cancer Res. 64:2343-2346). The hybridoma cell line expressing 2C4 (pertuzumab) was deposited with the American Type Culture Collection (ATCC), 10801 University Boulevard, Manassas, Va. 20110-2209, USA as ATCC HB-12697 on Apr. 8, 1999. Pertuzumab blocks the ability of the HER2 receptor to collaborate with other HER receptor family members, i.e. HER1/EGFR, HER3, and HER4 (Agus et al (2002) Cancer Cell 2:127-37; Jackson et al (2004) Cancer Res 64:2601-9; Takai et al (2005) Cancer 104:2701-8; U.S. Pat. No. 6,949,245). In cancer cells, interfering with the ability of HER2 to collaborate with other HER family receptors blocks cell signaling and may ultimately lead to cancer cell growth inhibition and death of the cancer cell. HDIs, because of their unique mode of action, have the potential to work in a wide variety of tumors, including those that do not overexpress HER2 (Mullen et al (2007) Molecular Cancer Therapeutics 6:93-100).

Pertuzumab is based on the human IgG1 (κ) framework sequences. It consists of two heavy chains and two light chains. Like trastuzumab, pertuzumab is directed against the extracellular domain of HER2. However, it differs from trastuzumab in the epitope-binding regions of the light chain and heavy chain. As a result, pertuzumab binds to an epitope within what is known as a sub-domain 2 of HER2, while the epitope from trastuzumab is localized to sub-domain 4 (Cho et al. 2003; Franklin et al. 2004). Pertuzumab acts by blocking the association of HER2 with other HER family members, including HER1 (epidermal growth factor receptor; EGFR), HER3, and HER4. This association is required for signaling in the presence of ligand via MAP-kinase and PI3-kinase. As a result, pertuzumab inhibits ligand-initiated intracellular signaling Inhibition of these signaling pathways can result in growth arrest and apoptosis, respectively (Hanahan and Weinberg 2000). Because pertuzumab and trastuzumab bind at distinct epitopes on the HER2 receptor, ligand-activated downstream signaling is blocked by pertuzumab but not by trastuzumab. Pertuzumab, therefore, may not require HER2 overexpression to exert its activity as an anti-tumor agent. In addition, because of their complementary modes of action, the combination of pertuzumab and T-DM1 may have a potential role in HER2-overexpressing diseases.

Pertuzumab has been evaluated as a single agent in five Phase II studies conducted in various cancer types, including MBC expressing low levels of HER2, non-small cell lung cancer, hormone-refractory prostate cancer, and ovarian cancer. A Phase II trial evaluated pertuzumab as a single agent in the second- or third-line treatment of metastatic breast cancer (MBC) patients with normal HER2 expression (Cortes et al. (2005) J. Clin. Oncol. 23:3068). Pertuzumab has been evaluated in two Phase II studies in combination with trastuzumab (Baselga J, et al. "A Phase II trial of trastuzumab and pertuzumab in patients with HER2-positive metastatic breast cancer that had progressed during trastuzumab therapy: full response data", European Society of Medical Oncology, Stockholm, Sweden, Sep. 12-16, 2008; Gelmon et al (2008) J. Clin. Oncol. 26:1026). The first study enrolled 11 patients with HER2-positive MBC who previously received up to three prior trastuzumab-containing regimens (Portera et al. 2007).

Bevacizumab (CAS Reg. No. 216974-75-3, AVASTIN®, Genentech) is an anti-VEGF monoclonal antibody against vascular endothelial growth factor (U.S. Pat. No. 7,227,004; U.S. Pat. No. 6,884,879; U.S. Pat. No. 7,060,269; U.S. Pat. No. 7,169,901; U.S. Pat. No. 7,297,334) used in the treatment of cancer, where it inhibits tumor growth by blocking the formation of new blood vessels. Bevacizumab was the first clinically available angiogenesis inhibitor in the United States, approved by the FDA in 2004 for use in combination with standard chemotherapy in the treatment of metastatic colon cancer and most forms of metastatic non-small cell lung cancer. Several late-stage clinical studies are underway to determine its safety and effectiveness for patients with: adjuvant/non-metastatic colon cancer, metastatic breast cancer, metastatic renal cell carcinoma, metastatic glioblastoma multiforme, metastatic ovarian cancer, metastatic hormone-refractory prostate cancer, and metastatic metastatic or unresectable locally advanced pancreatic cancer.

An anti-VEGF antibody will usually not bind to other VEGF homologues such as VEGF-B or VEGF-C, nor other growth factors such as PlGF, PDGF or bFGF. Preferred anti-VEGF antibodies include a monoclonal antibody that binds to the same epitope as the monoclonal anti-VEGF antibody A4.6.1 produced by hybridoma ATCC HB 10709; a recombinant humanized anti-VEGF monoclonal antibody generated according to Presta et al. (1997) Cancer Res. 57:4593-4599, including but not limited to bevacizumab. Bevacizumab includes mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of bevacizumab, including most of the framework regions, is derived from human IgG1, and about 7% of the sequence is derived from the murine antibody A4.6.1. Bevacizumab has a molecular mass of about 149,000 daltons and is glycosylated. Bevacizumab and other humanized anti-VEGF antibodies are further described in U.S. Pat. No. 6,884,879. Additional anti-VEGF antibodies include the G6 or B20 series antibodies (e.g., G6-31, B20-4.1), as described in any one of FIGS. 27-29 of WO2005/012359. In one embodiment, the B20 series antibody binds to a functional epitope on human VEGF comprising residues F17, M18, D19, Y21, Y25, Q89, I91, K101, E103, and C104

The A 4.6.1 (ATCC HB 10709) and B 2.6.2 (ATCC HB 10710) anti-VEGF expressing hybridoma cell lines have been deposited and maintained with the American Type Culture Collection (ATCC), 10801 University Boulevard, Manassas, Va. 20110-2209 USA. The clone expressing VEGF-E polypeptide (U.S. Pat. No. 6,391,311) encoded by the nucleotide sequence insert of the ATCC deposit identified as DNA29101-1276 was deposited on Mar. 5, 1998 and maintained as ATCC 209653 with the American Type Culture Collection, 10801 University Boulevard, Manassas, Va. 20110-2209, USA.

5-FU (fluorouracil, 5-fluorouracil, CAS Reg. No. 51-21-8) is a thymidylate synthase inhibitor and has been used for decades in the treatment of cancer, including colorectal and pancreatic cancer (U.S. Pat. No. 2,802,005; U.S. Pat. No. 2,885,396; Barton et al (1972) Jour. Org. Chem. 37:329; Hansen, R. M. (1991) Cancer Invest. 9:637-642). 5-FU is named as 5-fluoro-1H-pyrimidine-2,4-dione, and has the structure:

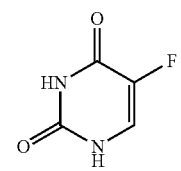

Carboplatin (CAS Reg. No. 41575-94-4) is a chemotherapeutic drug used against ovarian carcinoma, lung, head and neck cancers (U.S. Pat. No. 4,140,707). Carboplatin is named as azanide; cyclobutane-1,1-dicarboxylic acid platinum, and has the structure:

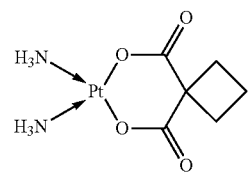

Lapatinib (CAS Reg. No. 388082-78-8, TYKERB®, GW572016, Glaxo SmithKline) has been approved for use in combination with capecitabine (XELODA®, Roche) for the treatment of patients with advanced or metastatic breast cancer whose tumors over-express HER2 (ErbB2) and who have received prior therapy including an anthracycline, a taxane and trastuzumab. Lapatinib is an ATP-competitive epidermal growth factor (EGFR) and HER2/neu (ErbB-2) dual tyrosine kinase inhibitor (U.S. Pat. No. 6,727,256; U.S. Pat. No. 6,713,485; U.S. Pat. No. 7,109,333; U.S. Pat. No. 6,933,299; U.S. Pat. No. 7,084,147; U.S. Pat. No. 7,157,466; U.S. Pat. No. 7,141,576) which inhibits receptor autophosphorylation and activation by binding to the ATP-binding pocket of the EGFR/HER2 protein kinase domain. Lapatinib is named as N-(3-chloro-4-(3-fluorobenzyloxy)phenyl)-6-(5-((2-(methylsulfonyl)ethylamino)methyl)furan-2-yl)quinazolin-4-amine, and has the structure:

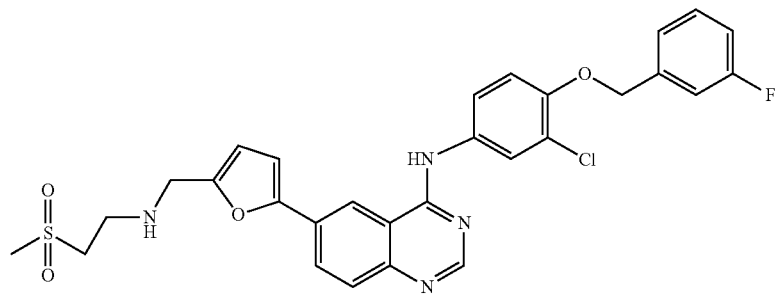 [SMILES: CS(=O)(=O)CCNCc1ccc(-c2ccc3ncnc(Nc4ccc(OCc5cccc(F)c5)c(Cl)c4)c3c2)o1]

ABT-869 (Abbott and Genentech) is a multi-targeted inhibitor of VEGF and PDGF family receptor tyrosine kinases, for the potential oral treatment of cancer (U.S. Pat. No. 7,297,709; US 2004/235892; US 2007/104780). Clinical trials have been initiated, treating non-small cell lung cancer (NSCLC), hepatocellular carcinoma (HCC), and renal cell carcinoma (RCC). ABT-869 is named as 1-(4-(3-amino-1H-indazol-4-yl)phenyl)-3-(2-fluoro-5-methylphenyl)urea (CAS No. 796967-16-3), and has the structure:

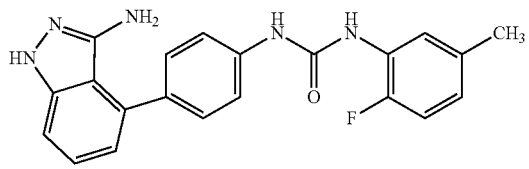 [SMILES: Cc1ccc(F)c(NC(=O)Nc2ccc(-c3cccc4[nH]nc(N)c34)cc2)c1]

Docetaxel (TAXOTERE®, Sanofi-Aventis) is used to treat breast, ovarian, and NSCLC cancers (U.S. Pat. No. 4,814,470; U.S. Pat. No. 5,438,072; U.S. Pat. No. 5,698,582; U.S. Pat. No. 5,714,512; U.S. Pat. No. 5,750,561). Docetaxel is named as (2R,3S)—N-carboxy-3-phenylisoserine, N-tert-butyl ester, 13-ester with 5,20-epoxy-1,2,4,7,10,13-hexahydroxytax-11-en-9-one 4-acetate 2-benzoate, trihydrate (U.S. Pat. No. 4,814,470; EP 253738; CAS Reg. No. 114977-28-5) and has the structure:

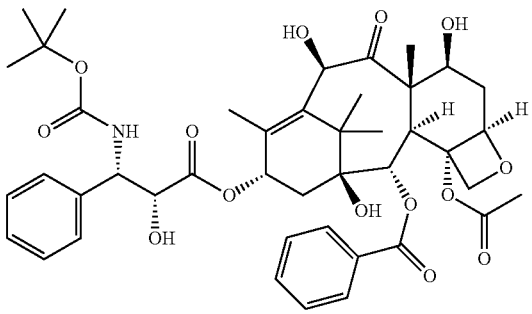

GDC-0941 (Genentech Inc.), is a selective, orally bioavailable thienopyrimidine inhibitor of PI3K with promising pharmacokinetic and pharmaceutical properties (Folkes et al (2008) Jour. of Med. Chem. 51(18):5522-5532; US 2008/0076768; US 2008/0207611; Belvin et al, American Association for Cancer Research Annual Meeting 2008, 99th:April 15, Abstract 4004; Folkes et al, American Association for Cancer Research Annual Meeting 2008, 99th:April 14, Abstract LB-146; Friedman et al, American Association for Cancer Research Annual Meeting 2008, 99th:April 14, Abstract LB-110). GDC-0941, shows synergistic activity in vitro and in vivo in combination with certain chemotherapeutic agents against solid tumor cell lines (U.S. Ser. No. 12/208,227, Belvin et al "Combinations Of Phosphoinositide 3-Kinase Inhibitor Compounds And Chemotherapeutic Agents, And Methods Of Use", filed 10 Sep. 2008). GDC-0941 is named as 4-(2-(1H-indazol-4-yl)-6-((4-(methylsulfonyl)piperazin-1-yl)methyl)thieno[3,2-d]pyrimidin-4-yl)morpholine (CAS Reg. No. 957054-30-7), and has the structure:

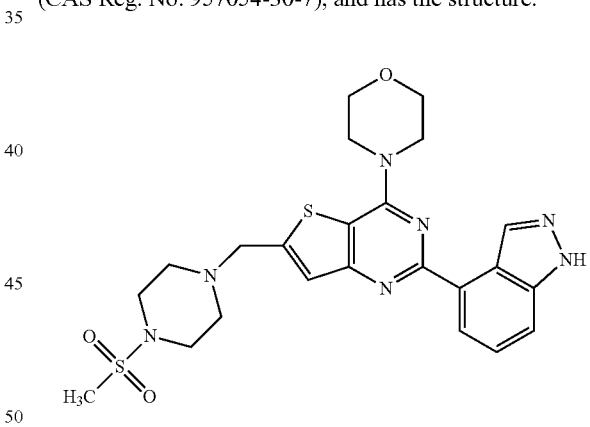

GNE-390 (Genentech Inc.), is a selective, orally bioavailable thienopyrimidine inhibitor of PI3K with promising pharmacokinetic and pharmaceutical properties (US 2008/0242665; WO 2008/070740). GNE-390 shows synergistic activity in vitro and in vivo in combination with certain chemotherapeutic agents against solid tumor cell lines (U.S. Ser. No. 12/208,227, Belvin et al "Combinations Of Phosphoinositide 3-Kinase Inhibitor Compounds And Chemotherapeutic Agents, And Methods Of Use", filed 10 Sep. 2008). GNE-390 is named as (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one, and has the structure:

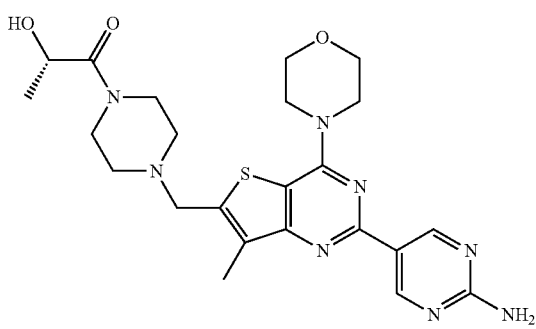 [SMILES: Cc1c(CN2CCN(C(=O)[C@H](C)O)CC2)sc2c(N3CCOCC3)nc(-c3cnc(N)nc3)nc12]

Biological Evaluation

In vitro cell culture studies using trastuzumab-MCC DM1 T-DM1) combined with different chemotherapeutic or biologically targeted agents were performed on a number of HER2-amplified cell lines. Data were analyzed using the Chou & Talalay method to determine the Combination Index (CI) value for each combination, set up in multiples of the IC50 for each drug. CI values less than 0.7 denote synergy; CI values between 0.7-1.3 denote additivity; and CI values greater than 1.3 denote antagonism. For combinations with chemotherapeutic agents, T-DM1 combined with docetaxel or 5-FU resulted in additive or synergistic anti-proliferative activity, while combinations with either gemcitabine or carboplatin had no effect or were antagonistic with T-DM1. Mouse xenograft studies showed similar results where T-DM1 combined with docetaxel or 5-FU resulted in greatly enhanced anti-tumor efficacy compared to treatment with individual agents. T-DM1 combined with carboplatin resulted in enhanced efficacy compared to either drug alone whereas the combination of T-DM1 with gemcitabine was not more efficacious than T-DM1 alone. T-DM1 combined with either pertuzumab, lapatinib or GDC-0941 resulted in additive or synergistic anti-proliferative activity in cell culture experiments, and in greatly enhanced anti-tumor efficacy in vivo compared to treatment with individual agents. In contrast, unconjugated trastuzumab antagonized the activity of T-DM1 due to binding of the same epitope on HER2. In vivo studies using combinations of T-DM1 with anti-angiogenic agents such as the antibody B20-4.1 or the small molecule inhibitor ABT-869 resulted in enhanced anti-tumor efficacy with all combinations tested, with the exception of the highest dose of T-DM1 (10 or 15 mg/kg) given with B20-4.1.

Combinations of trastuzumab-MCC-DM1 (T-DM1) with numerous anti-cancer drugs were studied by measuring both the in vitro anti-proliferative activity in HER2-overexpressing breast tumor cells and in vivo anti-tumor efficacy in breast cancer xenograft models. In these studies, trastuzumab-MCC-DM1 was added to either cytotoxic chemotherapeutic agents, antibodies, or small molecule kinase inhibitors.

The combination of anti-VEGF murine antibody B20-4.1 (Liang et al (2006) Jour. Biol. Chem. 281:951-961), a bevacizumab surrogate, and trastuzumab-MCC-DM1 in breast cancer mouse xenograft models resulted in greater anti-tumor activity than B20-4.1 alone. The results of these studies provide predictive basis of synergistic effects and rationale for future clinical evaluation of treatment regimens which include trastuzumab-MCC-DM1 in combination with different anti-tumor therapies in HER2-positive breast cancer.

Synergistic drug effects were observed with combinations of HER2-targeted agents, such as trastuzumab-DM1 plus lapatinib, or trastuzumab-DM1 combined with the HER2 antibody pertuzumab (a HER2 dimerization inhibitor). Trastuzumab-MCC-DM1 combined with carboplatin or 5-FU showed enhanced activity compared to treatment with individual agents alone, whereas combination treatment with gemcitabine did not result in increased anti-tumor activity.

Blockade of the PI3 kinase pathway with GDC-0941, a small molecule kinase pan inhibitor of p110 isoforms (WO 2007/129161), potentiated the activity of trastuzumab-DM1.

T-DM1 combined with the PI3K inhibitor GDC-0941 enhanced anti-tumor activity of, in HER2-amplified breast cancer lines with mutated PI3K: BT-474 (K111N), MDA-361.1 (E545K), and KPL4 (H1047R). Combination treatment in vitro resulted in additive or synergistic inhibition of cell proliferation, as well as increased apoptosis. Similarly, in vivo efficacy was augmented with combined drug treatment compared to single agent activity in the MDA-MB-361.1 and Fo5 HER2-amplified xenograft models. Biochemical analyses of biomarkers for each agent showed inhibition of phospho-Akt and phospho-ERK by both T-DM1 and GDC-0941, decreased phosphorylation of Rb and PRAS40 by GDC-0941, and increased levels of the mitotic markers phospho-histone H3 and cyclin B1 after treatment with T-DM1. In addition, T-DM1 treatment resulted in apoptosis in these breast cancer models as determined by appearance of the 23 kDa PARP-cleavage fragment, decreased levels of Bcl-XL, as well as activation of caspases 3 and 7. Addition of GDC-0941 to T-DM1 further enhanced apoptosis induction. These studies provide evidence for the use of rational drug combinations in HER2-amplified breast cancer and offer additional therapeutic approaches for patients whose disease progresses on trastuzumab or lapatinib-based therapy.

In Vitro Cell Proliferation Assays

The in vitro potency of the combinations of trastuzumab-MCC-DM1 with chemotherapeutic agents was measured by the cell proliferation assay of Example 2; the CellTiter-Glo® Luminescent Cell Viability Assay, commercially available from Promega Corp., Madison, Wis. This homogeneous assay method is based on the recombinant expression of *Coleoptera* luciferase (U.S. Pat. No. 5,583,024; U.S. Pat. No. 5,674,713; U.S. Pat. No. 5,700,670) and determines the number of viable cells in culture based on quantitation of the ATP present, an indicator of metabolically active cells (Crouch et al (1993) J. Immunol. Meth. 160:81-88; U.S. Pat. No. 6,602, 677). The CellTiter-Glo® Assay was conducted in 96 or 384 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay can be used with various multiwell formats, e.g. 96 or 384 well format. Data can be recorded by luminometer or CCD camera imaging device. The luminescence output is presented as relative light units (RLU), measured over time.

The anti-proliferative effects of trastuzumab-MCC-DM1 and combinations with chemotherapeutic agents were measured by the CellTiter-Glo® Assay (Example 2) against the tumor cell lines in FIGS. 1-9 and 18-33.

Exemplary embodiments include a method for determining compounds to be used in combination for the treatment of cancer comprising: a) administering a therapeutic combination of trastuzumab-MCC-DM1 (T-DM1) and a chemotherapeutic agent to an in vitro tumor cell line, and b) measuring a synergistic or non-synergistic effect. A combination index (CI) value greater than 1.3 denotes antagonism; CI values between 0.7-1.3 denote additivity, and CI values less than 0.7 denote synergistic drug interactions.

FIG. 1 shows the antagonistic effect of trastuzumab in combination with trastuzumab-MCC-DM1 (T-DM1) at various concentrations in multiples of the individual IC50 values (Table 1) in SK-BR-3 cells which are trastuzumab-sensitive. The viable cell number is plotted relative to the IC50 multiple values. The combination index (CI) over $IC_{10}$ to $IC_{90}$ for each combination is greater than 2, indicating antagonism in vitro. However the combination of T-DM1+ trastuzumab in vivo does not show an antagonistic effect.

TABLE 1

SK-BR-3 Proliferation - 3 days

| IC50 multiple | trastuzumab ng/ml | T-DM1 ng/ml | Effect (%) | CI |
|---|---|---|---|---|
| 0.5X | 20.57 | 2.28 | 5.1 | >2 |
| 1X | 61.72 | 6.86 | 26.2 | >2 |
| 2X | 185.19 | 20.58 | 36.3 | >2 |
| 4X | 555.56 | 61.73 | 43.6 | >2 |
| 8X | 1666.67 | 185.19 | 45.0 | >2 |
| 16X | 5000 | 555.56 | 41.7 | >2 |

Figure 2:
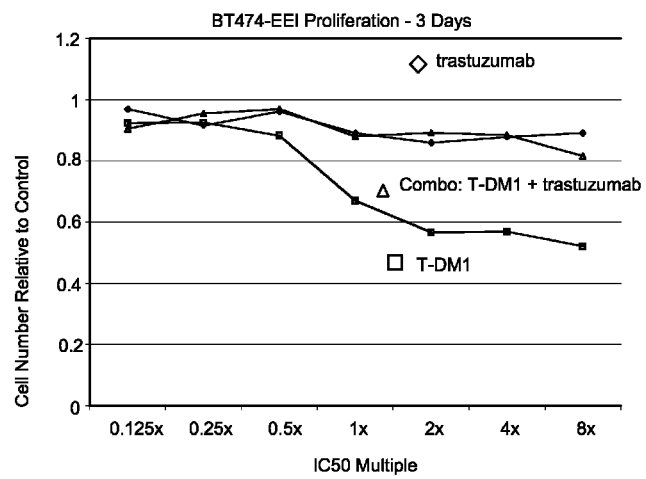
FIG. 2 shows a plot of BT-474 EEI in vitro cell viability at 3 days versus IC50 multiple concentrations of trastuzumab, trastuzumab-MCC-DM1 (T-DM1), and the combination of trastuzumab and T-DM1.

FIG. 2 shows the antagonistic effect of trastuzumab in combination with trastuzumab-MCC-DM1 (T-DM1) at various concentrations in multiples of the individual IC50 values (Table 2) in BT-474 EEI cells which are trastuzumab-resistant. The viable cell number is plotted relative to the IC50 multiple values. The combination index (CI) over $IC_{10}$ to $IC_{90}$ for each combination is great than 2, indicating antagonism.

TABLE 2

BT-474-EEI Proliferation - 3 days

| IC50 multiple | trastuzumab ng/ml | T-DM1 ng/ml | Effect (%) | CI |
|---|---|---|---|---|
| 0.125X | 1.52 | 1.52 | 9.5 | >2 |
| 0.25X | 4.57 | 4.57 | 4.5 | >2 |
| 0.5X | 13.71 | 13.71 | 3.1 | >2 |
| 1X | 41.15 | 41.15 | 12.1 | >2 |
| 2X | 123.46 | 123.46 | 10.8 | >2 |
| 4X | 370.4 | 370.4 | 11.6 | >2 |
| 8X | 1111.1 | 1111.1 | 18.4 | >2 |

Figure 3:
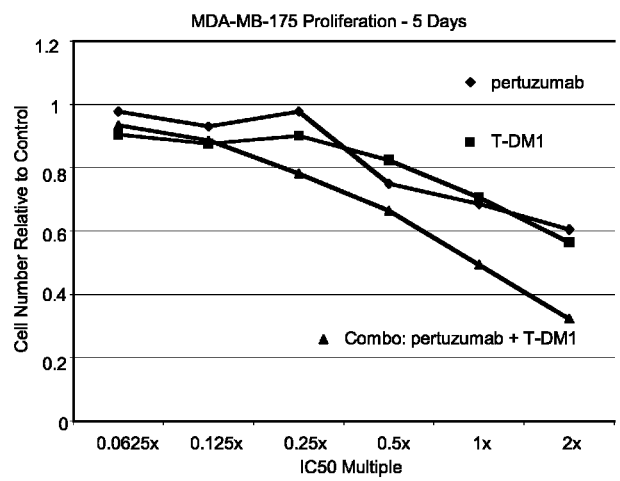
FIG. 3 shows a plot of MDA-MB-175 in vitro cell viability at 5 days versus IC50 multiple concentrations of pertuzumab, trastuzumab-MCC-DM1 (T-DM1), and the combination of pertuzumab and T-DM1.

FIG. 3 shows the synergistic effect of pertuzumab in combination with trastuzumab-MCC-DM1 (T-DM1) at various concentrations in multiples of the individual IC50 values (Table 3) in MDA-MB-175 cells. The viable cell number is plotted relative to the IC50 multiple values. The combination index (CI) over $IC_{10}$ to $IC_{90}$ for each combination is under 1, with the average CI=0.387, indicating synergism (Table 3).

TABLE 3

MDA-MB-175 Proliferation - 5 days

| IC50 multiple | pertuzumab ng/ml | T-DM1 ng/ml | Effect (%) | CI |
|---|---|---|---|---|
| 0.0625X | 39.06 | 31.25 | 21.1 | 0.2 |
| 0.125X | 78.13 | 62.5 | 33.3 | 0.107 |
| 0.25X | 156.3 | 125 | 21.9 | .766 |
| 0.5X | 312.5 | 250 | 33.6 | 0.597 |
| 1X | 625 | 500 | 50.7 | 0.391 |
| 2X | 1250 | 1000 | 67.7 | 0.259 |

Figure 3A:
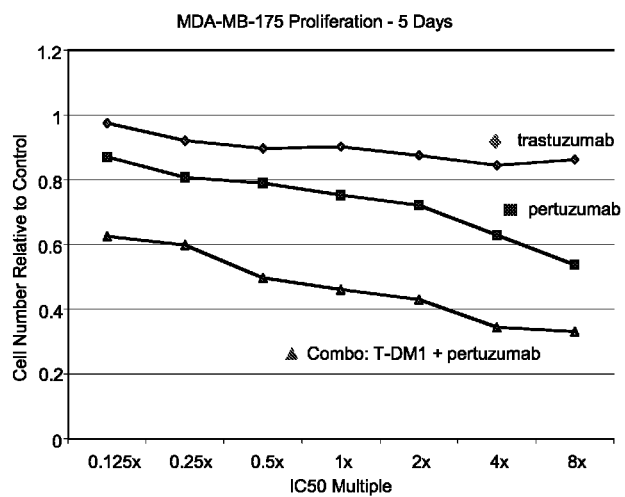
FIG. 3a shows a plot of MDA-MB-175 in vitro cell viability at 5 days versus IC50 multiple concentrations of pertuzumab, trastuzumab-MCC-DM1 (T-DM1), and the combination of pertuzumab and T-DM1.

FIG. 3a shows a plot of MDA-MB-175 in vitro cell viability at 5 days versus IC50 multiple concentrations of pertuzumab, trastuzumab-MCC-DM1 (T-DM1), and the combination of pertuzumab and T-DM1. The viable cell number is plotted relative to the IC50 multiple values. The combination index (CI) over $IC_{10}$ to $IC_{90}$ for each combination is under 1, with the average CI=0.096, indicating synergism (Table 3a).

TABLE 3a

MDA-MB-175 Proliferation - 5 days

| IC50 multiple | Effect (%) | CI |
|---|---|---|
| 0.0625x | 21.3 | 0.093 |
| 0.125x | 37.5 | 0.037 |
| 0.25x | 40.1 | 0.060 |
| 0.5x | 50.3 | 0.052 |
| 1x | 53.9 | 0.078 |
| 2x | 57.0 | 0.120 |
| 4x | 65.5 | 0.117 |
| 8x | 66.8 | 0.208 |

Figure 4:
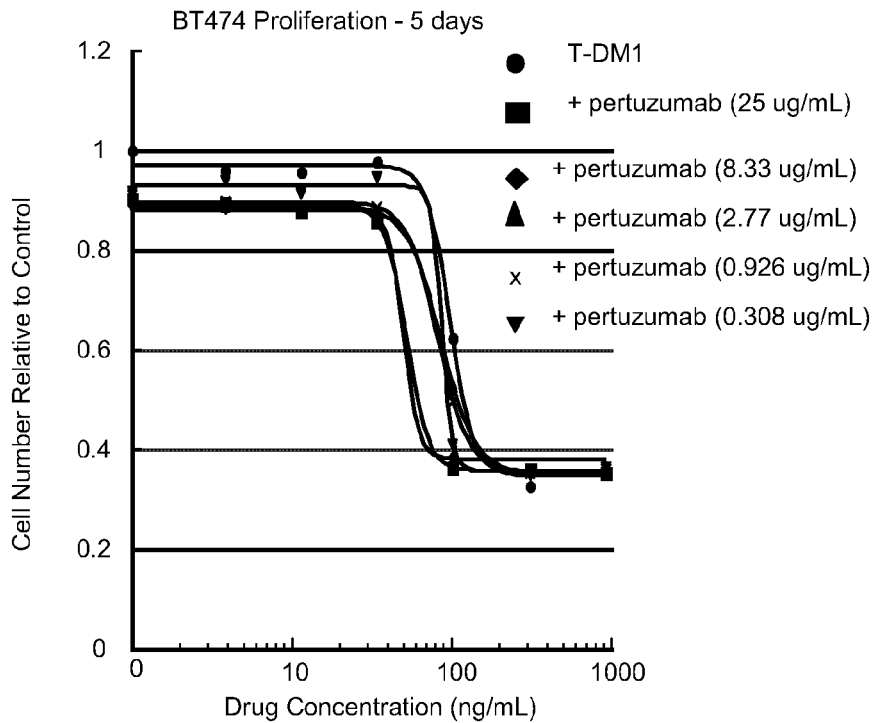
FIG. 4 shows a plot of BT-474 in vitro cell viability at 5 days versus various fixed doses of pertuzumab in combination with dose response of trastuzumab-MCC-DM1 (T-DM1), and various doses of T-DM1 alone.

FIG. 4 shows a plot of BT-474 in vitro cell viability at 5 days versus various fixed doses of pertuzumab in combination with dose response of trastuzumab-MCC-DM1 (T-DM1), and various doses of T-DM1 alone. FIG. 4 shows the effects of fixed doses of T-DM1 in combination with various dosages of pertuzumab. Addition of pertuzumab to T-DM1 results in slightly greater anti-proliferative activity than T-DM1 alone.

Figure 5:
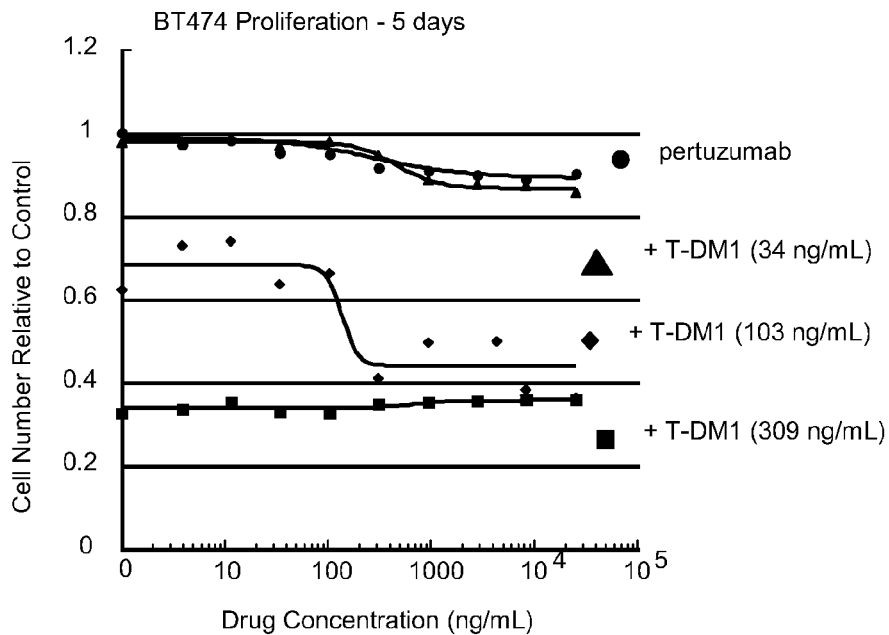
FIG. 5 shows a plot of BT-474 in vitro cell viability at 5 days versus various fixed doses of trastuzumab-MCC-DM1 (T-DM1) in combination with dose response of pertuzumab, and various doses of pertuzumab alone.

FIG. 5 shows a plot of BT-474 in vitro cell viability at 5 days versus various fixed doses of trastuzumab-MCC-DM1 (T-DM1) in combination with dose response of pertuzumab, and various doses of pertuzumab alone. FIG. 5 shows the effects of fixed doses of pertuzumab in combination with various dosages of T-DM1 on BT-474 cell proliferation. Addition of T-DM1 to pertuzumab enhances the effect of pertuzumab alone.

Figure 6:
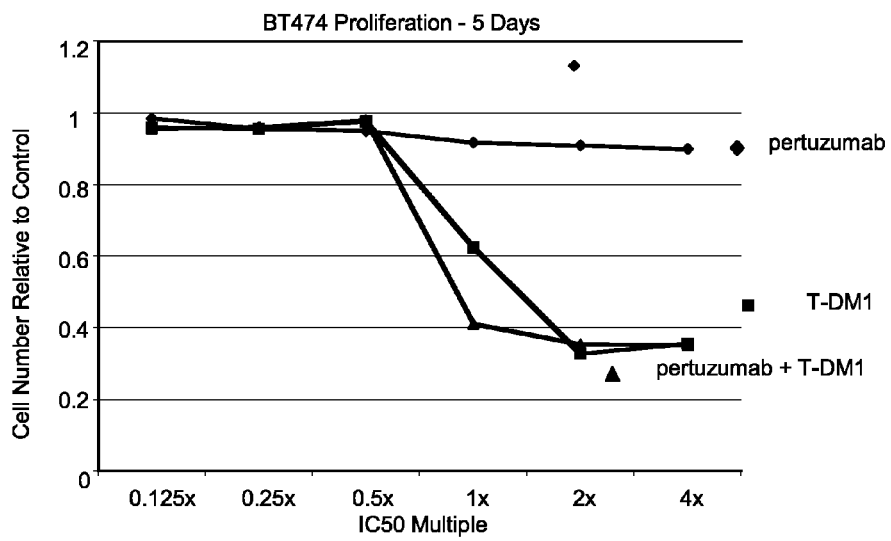
FIG. 6 shows a plot of BT-474 in vitro cell viability at 5 days versus IC50 multiple concentrations of pertuzumab, trastuzumab-MCC-DM1 (T-DM1), and the combination of pertuzumab and T-DM1.

FIG. 6 shows the synergistic effect of pertuzumab in combination with trastuzumab-MCC-DM1 (T-DM1) at various concentrations in multiples of the individual IC50 values (Table 4) in BT-474 cells. The viable cell number is plotted relative to the IC50 multiple values. Combination index (CI) values from $IC_{10}$ to $IC_{90}$ range from 0.198 to 1.328. The average CI for this range=0.658 indicating synergy.

TABLE 4

BT-474 Proliferation - 5 days

| IC50 multiple | pertuzumab ng/ml | T-DM1 ng/ml | Effect (%) | CI |
|---|---|---|---|---|
| 0.25X | 34.29 | 11.43 | 3.9 | >2 |
| 0.5X | 102.88 | 34.29 | 2.0 | >2 |
| 1X | 308.64 | 102.88 | 58.9 | 0.198 |
| 2X | 925.93 | 308.64 | 64.6 | 0.449 |
| 4X | 2777 | 926 | 64.9 | 1.328 |

Figure 7:
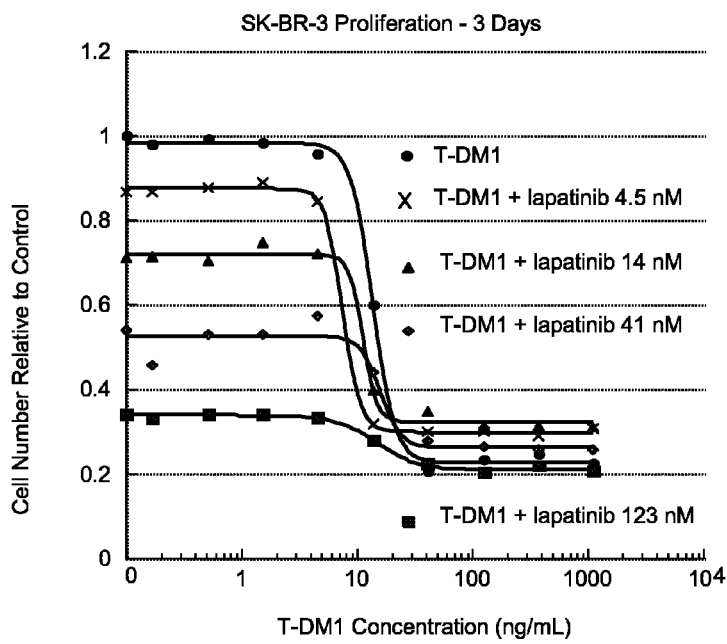
FIG. 7 shows a plot of SK-BR-3 in vitro cell viability at 3 days versus varying doses of T-DM1 in combination with fixed doses of lapatinib (4.5 nM, 14 nM, 41 nM, 123 nM), and varying doses of T-DM1 alone (0-1000 ng/ml).

FIG. 7 shows a plot of SK-BR-3 in vitro cell viability at 3 days versus varying doses of T-DM1 in combination with fixed doses of lapatinib (4.5 nM, 14 nM, 41 nM, 123 nM), and varying doses of T-DM1 alone (0-1000 ng/ml). Addition of lapatinib to T-DM1 results in slightly greater anti-proliferative activity than T-DM1 alone.

Figure 7A:
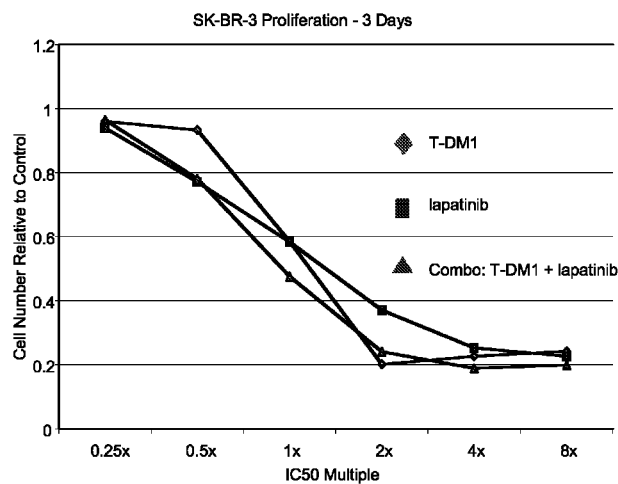
FIG. 7a shows a plot of SK-BR-3 in vitro cell viability at 3 days versus T-DM1, lapatinib, and fixed dose ratio combinations of T-DM1 and lapatinib.

FIG. 7a shows a plot of SK-BR-3 in vitro cell viability at 3 days versus T-DM1, lapatinib, and fixed dose ratio combinations of T-DM1 and lapatinib as shown in Table 7a. The average CI value between the IC10 and IC90=0.793, indicating additivity.

TABLE 7a

SK-BR-3 Proliferation - 3 days

| IC50 multiple | lapatinib nM | T-DM1 ng/ml | Effect (%) | CI |
|---|---|---|---|---|
| 0.25x | 4.57 | 1.52 | 3.5 | >2 |
| 0.5x | 13.72 | 4.57 | 22.0 | 1.384 |
| 1x | 41.15 | 13.72 | 52.5 | 0.596 |
| 2x | 123.44 | 41.15 | 75.9 | 0.406 |
| 4x | 370.33 | 123.44 | 81.1 | 0.787 |
| 8x | 1111 | 370.33 | 80.1 | >2 |

Figure 8A:
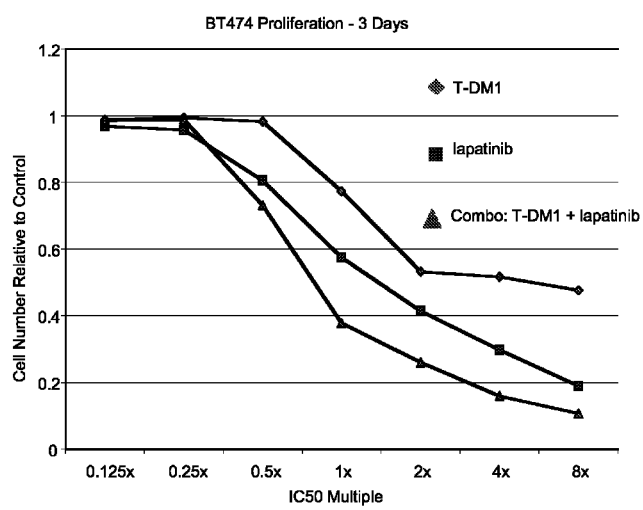
FIG. 8a shows a plot of BT-474 in vitro cell viability at 3 days versus T-DM1, lapatinib, and fixed dose ratio combinations of T-DM1 and lapatinib.

FIG. 8a shows a plot of BT-474 in vitro cell viability at 3 days versus T-DM1, lapatinib, and fixed dose ratio combinations of T-DM1 and lapatinib as shown in Table 8a. The average CI value between the IC10 and IC90=0.403, indicating synergy.

TABLE 8a

BT-474 Proliferation - 3 days

| IC50 multiple | lapatinib nM | T-DM1 ng/ml | Effect (%) | CI |
|---|---|---|---|---|
| 1.25x | 0.51 | 1.52 | 1.4 | >2 |
| 0.25x | 1.52 | 4.57 | 1.2 | >2 |
| 0.5x | 4.57 | 13.72 | 26.8 | 0.493 |
| 1x | 13.72 | 41.15 | 62.2 | 0.201 |
| 2x | 41.15 | 123.44 | 73.9 | 0.293 |
| 4x | 123.44 | 370.33 | 84.1 | 0.390 |
| 8x | 370.33 | 1111 | 89.3 | 0.638 |

Figure 8:
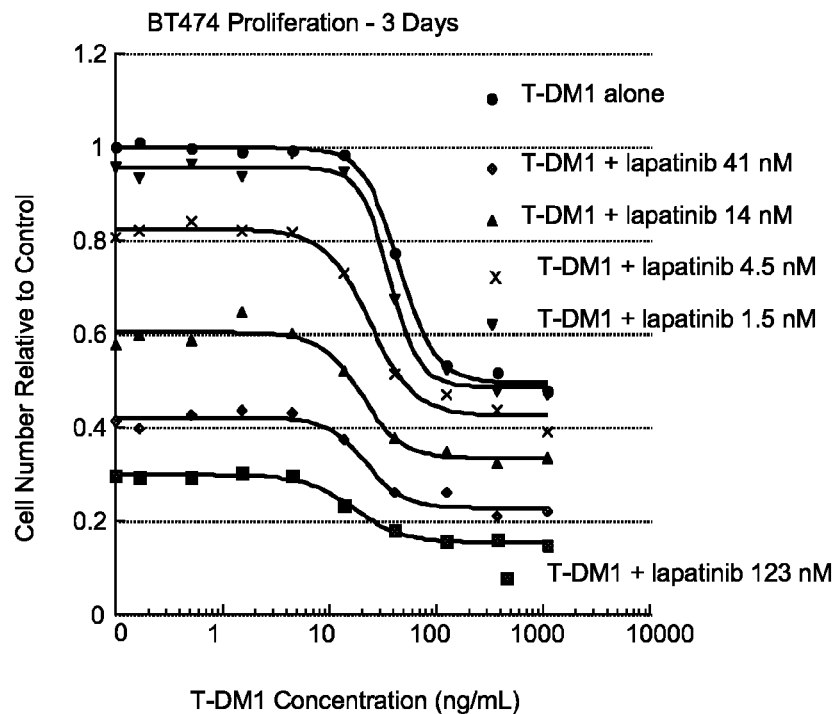
FIG. 8 shows a plot of BT-474 in vitro cell viability at 3 days versus varying doses of T-DM1 in combination with fixed doses of lapatinib (1.5 nM, 4.5 nM, 14 nM, 41 nM, 123 nM), and varying doses of T-DM1 alone (0-1000 ng/ml).

FIG. 8 shows a plot of BT-474 in vitro cell viability at 3 days versus varying doses of T-DM1 in combination with fixed doses of lapatinib (1.5 nM, 4.5 nM, 14 nM, 41 nM, 123 nM), and varying doses of T-DM1 alone (0-1000 ng/ml). Addition of lapatinib to T-DM1 results in greater anti-proliferative activity compared to either drug alone.

Figure 9:
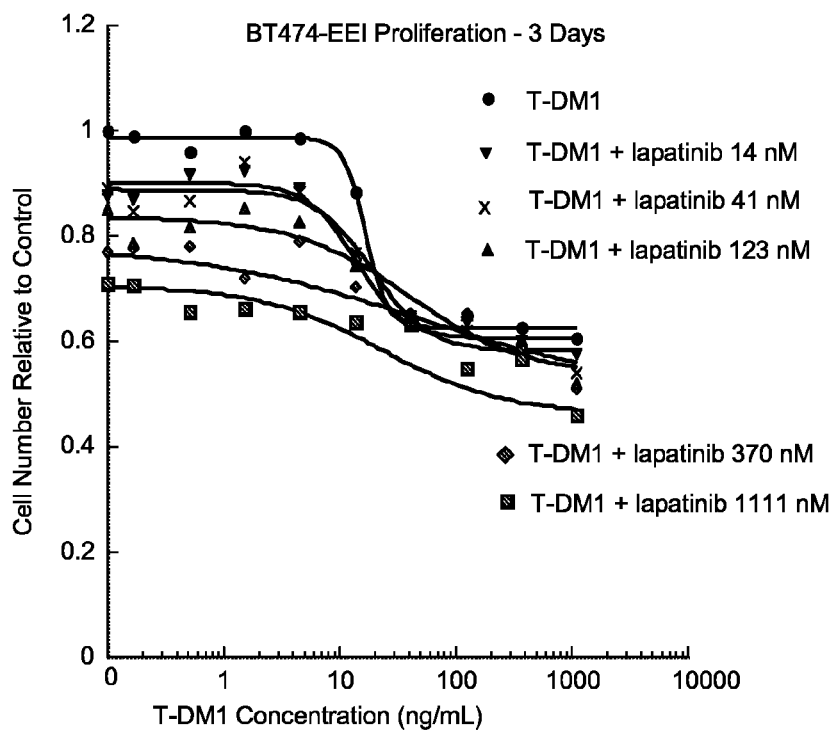
FIG. 9 shows a plot of BT-474-EEI in vitro cell viability at 3 days versus varying doses of T-DM1 in combination with fixed doses of lapatinib (14 nM, 41 nM, 123 nM, 370 nM, 1111 nM), and varying doses of T-DM1 alone (0-1000 ng/ml).

FIG. 9 shows a plot of BT-474-EEI in vitro cell viability at 3 days versus varying doses of T-DM1 in combination with fixed doses of lapatinib (14 nM, 41 nM, 123 nM, 370 nM, 1111 nM), and varying doses of T-DM1 alone (0-1000 ng/ml). Addition of lapatinib to T-DM1 results in greater anti-proliferative activity compared to either drug alone.

Figure 18:
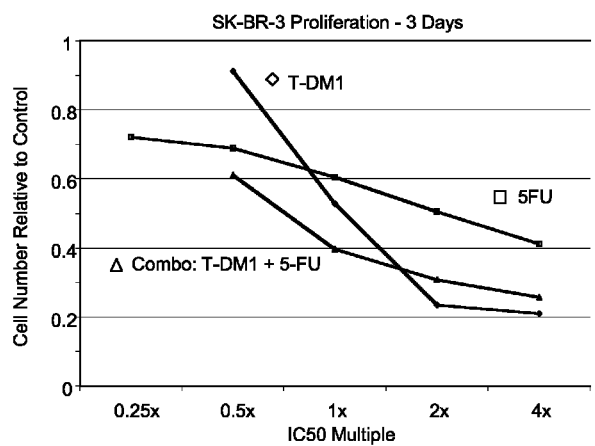
FIG. 18 shows a plot of SK-BR-3 in vitro cell viability at 3 days versus IC50 multiple concentrations of 5-FU, trastuzumab-MCC-DM1 (T-DM1), and fixed dose ratio combinations of 5-FU and T-DM1.

FIG. 18 shows a plot of SK-BR-3 in vitro cell viability at 3 days versus IC50 multiple concentrations of 5-FU, trastuzumab-MCC-DM1 (T-DM1), and fixed dose ratio combinations of 5-FU and T-DM1 (Table 18). The combination of 5-FU and T-DM1 is additive on SK-BR-3 cells, with the average CI between the IC10 and IC90=0.952.

TABLE 18

5-FU + T-DM1: SK-BR-3 Proliferation - 3 days

| IC50 multiple | 5-FU (µM) | T-DM1 ng/ml | Effect (%) | CI |
|---|---|---|---|---|
| 0.5x | 62.5 | 1.95 | 38.9 | 1.035 |
| 1x | 125 | 3.91 | 60.3 | 0.647 |

TABLE 18-continued

5-FU + T-DM1: SK-BR-3 Proliferation - 3 days

| IC50 multiple | 5-FU (µM) | T-DM1 ng/ml | Effect (%) | CI |
|---|---|---|---|---|
| 2x | 250 | 7.81 | 69.2 | 0.835 |
| 4x | 500 | 15.625 | 74.3 | 1.292 |

Figure 19:
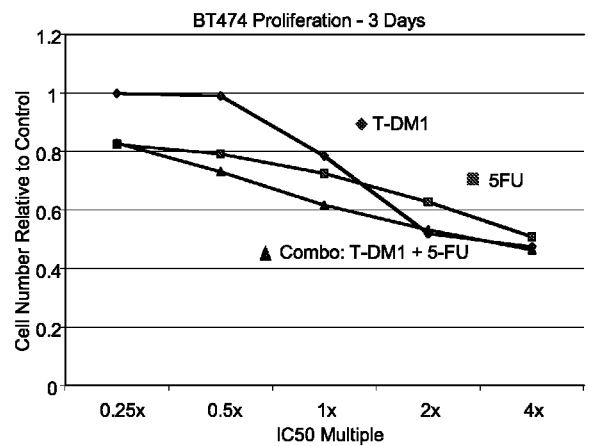
FIG. 19 shows a plot of BT-474 in vitro cell viability at 3 days versus IC50 multiple concentrations of 5-FU, trastuzumab-MCC-DM1 (T-DM1), and fixed dose ratio combinations of 5-FU and T-DM1.

FIG. 19 shows a plot of BT-474 in vitro cell viability at 3 days versus IC50 multiple concentrations of 5-FU, trastuzumab-MCC-DM1 (T-DM1), and fixed dose ratio combinations of 5-FU and T-DM1 (Table 19). The combination of 5-FU and T-DM1 is synergistic on BT-474 cells, with average CI value=0.623.

TABLE 19

5-FU + T-DM1: BT-474 Proliferation - 3 days

| IC50 multiple | 5-FU (µM) | T-DM1 ng/ml | Effect (%) | CI |
|---|---|---|---|---|
| 0.25x | 0.488 | 3.90 | 17.1 | 0.508 |
| 0.5x | 0.976 | 7.81 | 26.8 | 0.494 |
| 1x | 1.95 | 15.62 | 38.2 | 0.513 |
| 2x | 3.91 | 31.25 | 46.8 | 0.661 |
| 4x | 7.81 | 62.5 | 53.6 | 0.941 |

Figure 20:
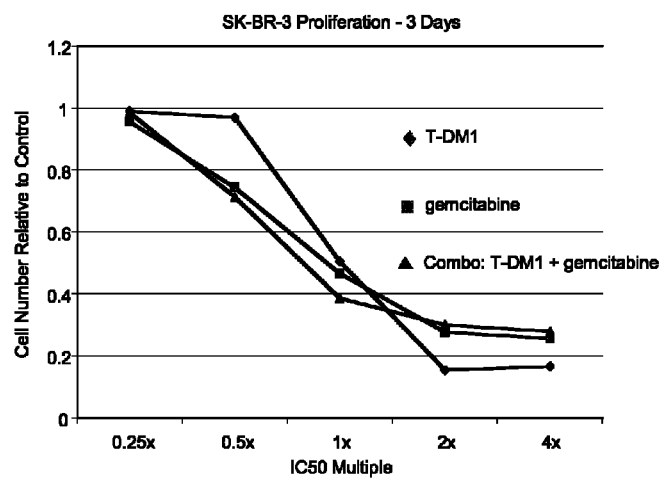
FIG. 20 shows a plot of SK-BR-3 in vitro cell viability at 3 days versus IC50 multiple concentrations of gemcitabine, trastuzumab-MCC-DM1 (T-DM1), and fixed dose ratio combinations of gemcitabine and T-DM1.

FIG. 20 shows a plot of SK-BR-3 in vitro cell viability at 3 days versus IC50 multiple concentrations of gemcitabine, trastuzumab-MCC-DM1 (T-DM1), and fixed dose ratio combinations of gemcitabine and T-DM1 (Table 20). Gemcitabine combined with T-DM1 results in an antagonistic drug interaction, with CI values >1.3 at all combinations tested.

TABLE 20 gemcitabine (GEM) + T-DM1: SK-BR-3 Proliferation - 3 days

| IC50 multiple | GEM (nM) | T-DM1 ng/ml | Effect (%) | CI |
|---|---|---|---|---|
| 0.5x | 3.12 | 6.25 | 28.7 | 1.308 |
| 1x | 6.25 | 12.5 | 61.4 | 1.500 |
| 2x | 12.5 | 25 | 69.9 | 2.588 |
| 4x | 25 | 50 | 72.2 | 4.957 |

Figure 21:
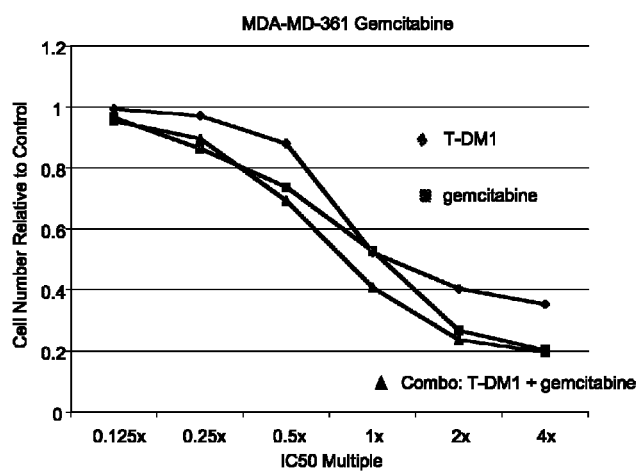
FIG. 21 shows a plot of MDA-MD-361 in vitro cell viability at 3 days versus IC50 multiple concentrations of gemcitabine, trastuzumab-MCC-DM1 (T-DM1), and fixed dose ratio combinations of gemcitabine and T-DM1.

FIG. 21 shows a plot of MDA-MD-361 in vitro cell viability at 3 days versus IC50 multiple concentrations of gemcitabine, trastuzumab-MCC-DM1 (T-DM1), and fixed dose ratio combinations of gemcitabine and T-DM1 (Table 21). The drug combination gives an antagonistic effect with the average CI=1.706.

TABLE 21 gemcitabine (GEM) + T-DM1:
MDA-MD-361 Proliferation - 3 days

| IC50 multiple | GEM (nM) | T-DM1 ng/ml | Effect (%) | CI |
|---|---|---|---|---|
| 0.125x | 0.39 | 3.12 | 4.5 | 1.420 |
| 0.25x | 0.78 | 6.25 | 10.3 | 1.584 |
| 0.5x | 1.56 | 12.5 | 30.7 | 1.336 |
| 1x | 3.12 | 25 | 59.2 | 1.280 |
| 2x | 6.25 | 50 | 76.3 | 1.581 |
| 4x | 12.5 | 100 | 80.3 | 2.747 |

Figure 22:
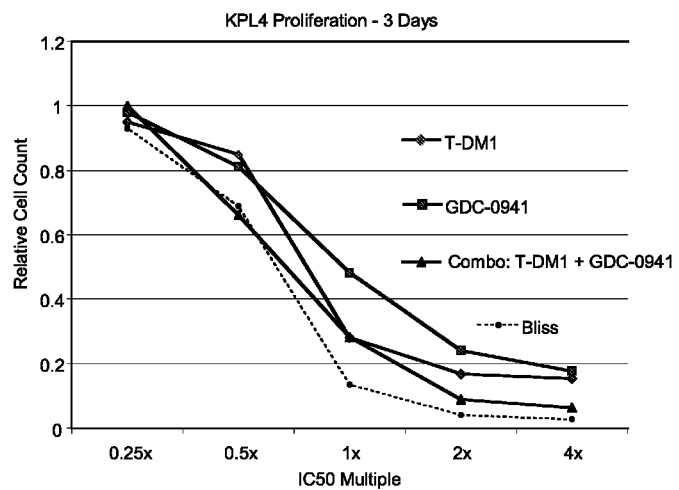
FIG. 22 shows a plot of KPL4 in vitro cell viability (proliferation) at 3 days after treatment with T-DM1, GDC-0941, and 1:10 fixed dose ratio combinations of T-DM1 and GDC-0941 (62.5 nM to 1 μM) at IC50 multiple concentrations from 0.25× to 4×. The Bliss prediction of additivity is plotted as the dotted line.

FIG. 22 shows a plot of KPL4 in vitro cell viability (proliferation) at 3 days after treatment with T-DM1, GDC-0941, and fixed dose ratio combinations of T-DM1 (6.25 to 100 ng/ml) and GDC-0941 (62.5 nM to 1 µM) at IC50 multiple concentrations from 0.25x to 4x. Table 22 shows the effect in the 10-90% inhibition range with calculated CI values and average CI of 1.111.

The Bliss prediction of additivity is plotted as the dotted line in FIG. 22. The Bliss independence plot shows the calculated additivity response from combination of two single compounds.

TABLE 22

GDC-0941 + T-DM1: KPL4 Proliferation - 3 days

| IC50 multiple | GDC-0941 (nM) | T-DM1 ng/ml | Effect (%) | CI |
|---|---|---|---|---|
| 0.25x | 62.5 | 6.25 | 1.0 | 6.319 |
| 0.5x | 125 | 12.5 | 33.9 | 1.229 |
| 1x | 250 | 25 | 71.8 | 1.053 |
| 2x | 500 | 50 | 91.1 | 1.051 |
| 4x | 1000 | 100 | 93.7 | 1.753 |

Figure 23:
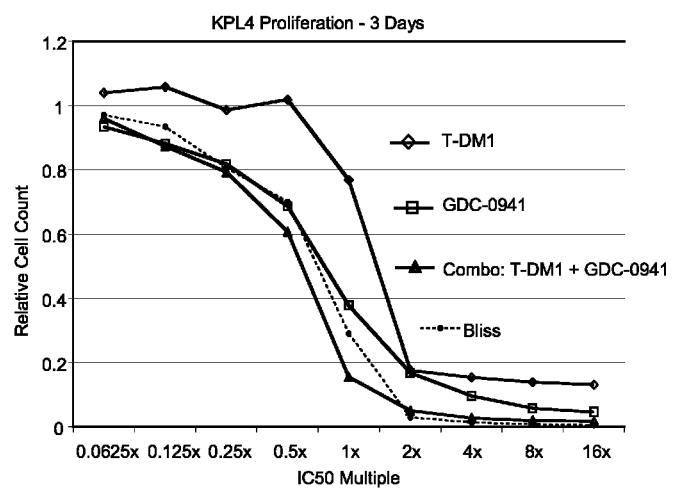
FIG. 23 shows a plot of KPL4 in vitro cell viability (proliferation) at 3 days after treatment with T-DM1, GDC-0941, and 1:25 fixed dose ratio combinations of T-DM1 (1.25 to 80 ng/ml) and GDC-0941 (31.25 nM to 2 μM) at IC50 multiple concentrations from 0.0625× to 16×. The Bliss prediction of additivity is plotted as the dotted line.

FIG. 23 shows a plot of KPL4 in vitro cell viability (proliferation) at 3 days after treatment with T-DM1, GDC-0941, and fixed dose ratio combinations of T-DM1 (1.25 to 80 ng/ml) and GDC-0941 (31.25 nM to 2 µM) at IC50 multiple concentrations from 0.0625x to 16x. The Bliss prediction of additivity is plotted as the dotted line. Table 23 shows the effect in the 10-90% inhibition range with calculated CI values and average CI of 0.802. The combination of T-DM1 and GDC-0941 is additive in the KPL4 cell line

TABLE 23

GDC-0941 + T-DM1: KPL4 Proliferation - 3 days

| IC50 multiple | GDC-0941 (nM) | T-DM1 ng/ml | Effect (%) | CI |
|---|---|---|---|---|
| 0.125x | 31.25 | 1.25 | 12.6 | 1.100 |
| 0.25x | 62.5 | 2.5 | 20.6 | 1.344 |
| 0.5x | 125 | 5 | 39.2 | 1.263 |
| 1x | 250 | 10 | 84.5 | 0.452 |
| 2x | 500 | 20 | 94.9 | 0.350 |
| 4x | 1000 | 40 | 97.1 | 0.440 |
| 8x | 2000 | 80 | 97.9 | 0.668 |

Figure 24:
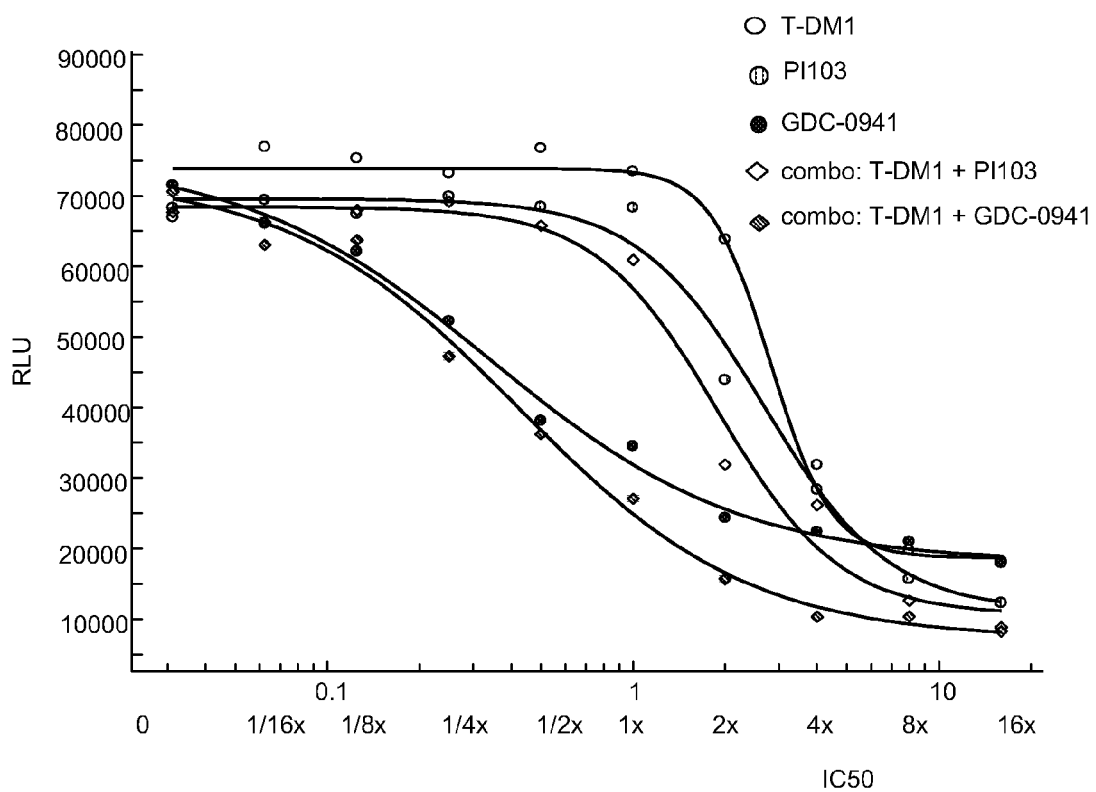
FIG. 24 shows a plot of Her2 amplified, HERCEPTIN® resistant, PIK3CA (H1047R) mutant, KPL-4 cells in vitro cell viability (proliferation) at 3 days after treatment with T-DM1, PI103, GDC-0941, and fixed dose ratio combinations of T-DM1+PI103, and T-DM1+GDC-0941, at IC50 multiple concentrations from 0 to 16×.

FIG. 24 shows a plot of Her2 amplified, HERCEPTIN® resistant, PIK3CA (H1047R) mutant, KPL-4 cells in vitro cell viability (proliferation) after treatment with T-DM1, PI103, GDC-0941, and fixed dose ratio combinations of T-DM1+PI103, and T-DM1+GDC-0941, at IC50 multiple concentrations from 0 to 16x. Table 24 shows the Combination Index values. The results suggest moderate in vitro synergy between T-DM-1 and GDC-0941 since the CI values are between 0.5 and 1, and additivity between T-DM-1 and PI103 since CI values are near 1.

TABLE 24

Combinations: KPL4 Proliferation

| CI at: | T-DM1 + GDC-0941 | T-DM1 + PI103 |
|---|---|---|
| ED50 | 0.74303 | 1.04069 |
| ED75 | 0.63448 | 0.9721 |
| ED90 | 0.54179 | 0.91094 |

The PI3K selective inhibitor, PI103 (Hayakawa et al (2007) Bioorg. Med. Chem. Lett. 17:2438-2442; Raynaud et al (2007) Cancer Res. 67:5840-5850; Fan et al (2006) Cancer Cell 9:341-349; U.S. Pat. No. 6,608,053), and has the structure:

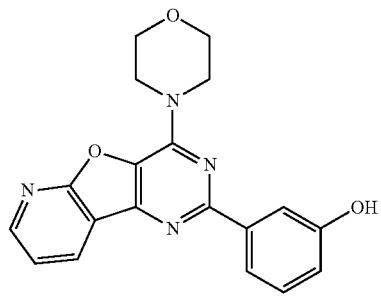 [SMILES: Oc1cccc(-c2nc(N3CCOCC3)c3oc4ncccc4c3n2)c1]

Figure 25:
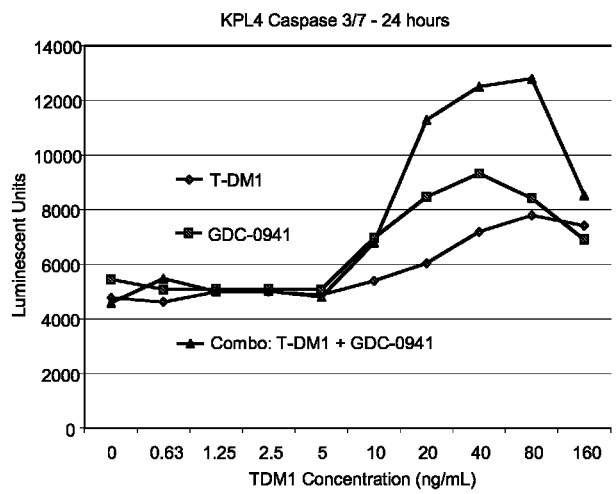
FIG. 25 shows a plot of KPL4 Caspase 3/7 in vitro cell viability (proliferation) at 24 hours after treatment with T-DM1, GDC-0941, and fixed dose ratio T-DM1 and GDC-0941 combinations at T-DM1 concentrations up to 160 ng/ml.

FIG. 25 shows a plot of KPL4 Caspase 3/7 in vitro cell apoptosis (programmed cell death) at 24 hours after treatment with T-DM1, GDC-0941, and fixed dose ratio combinations of T-DM1 and GDC-0941. The combination of T-DM1 and GDC-0941 results in greatly enhanced apoptosis compared to either agent alone.

Figure 26:
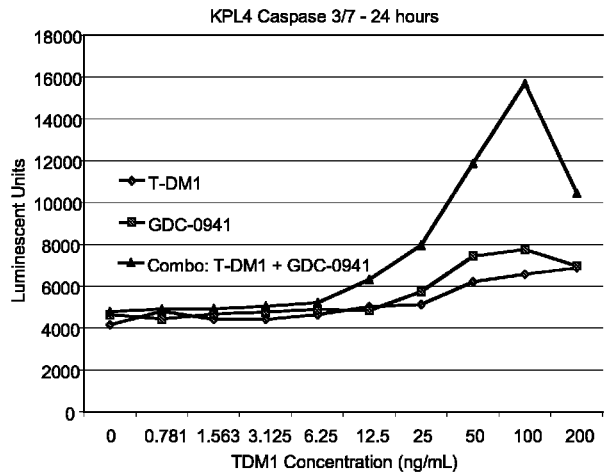
FIG. 26 shows a plot of KPL4 in vitro cell viability (proliferation) at 3 days after treatment with T-DM1, GDC-0941, and fixed dose ratio combinations of T-DM1 and GDC-0941 at T-DM1 concentrations from 0 to 200 ng/ml.

FIG. 26 shows a plot of KPL4 in vitro cell apoptosis (programmed cell death) at 3 days after treatment with T-DM1, GDC-0941, and fixed dose ratio combinations of T-DM1 and GDC-0941. The combination of T-DM1 and GDC-0941 results in greatly enhanced apoptosis compared to either agent alone.

Figure 27:
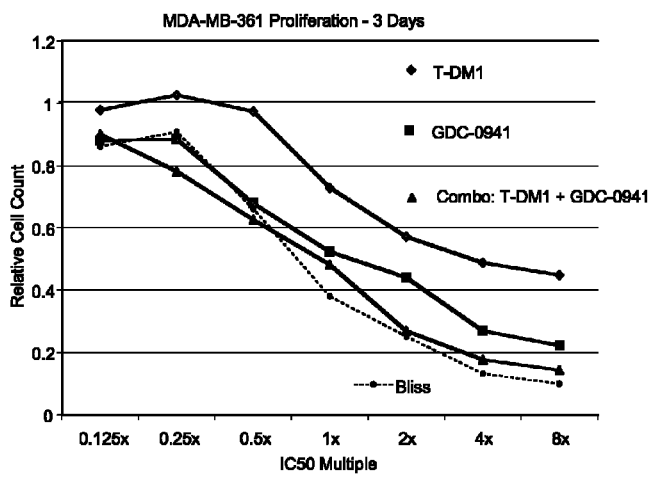
FIG. 27 shows a plot of MDA-0MB-361 in vitro cell viability (proliferation) at 3 days after treatment with T-DM1, GDC-0941, and 1:20 fixed dose ratio combinations of T-DM1 (3.125 to 50 ng/ml) and GDC-0941 (62.5 nM to 1 μM) at IC50 multiple concentrations from 0.125× to 8×. The Bliss prediction of additivity is plotted as the dotted line.

FIG. 27 shows a plot of MDA-MB-361 in vitro cell viability (proliferation) at 3 days after treatment with T-DM1, GDC-0941, and fixed dose ratio combinations of T-DM1 (3.125 to 50 ng/ml) and GDC-0941 (62.5 nM to 1 µM) at IC50 multiple concentrations from 0.125x to 8x. The Bliss prediction of additivity is plotted as the dotted line. Table 27 shows the effect in the 10-90% inhibition range with calculated CI values and average CI of 0.888. T-DM1 combined with GDC-0941 results in additive anti-proliferative activity in the MDA-MB-361 cells, with the average CI=0.889.

TABLE 27

GDC-0941 + T-DM1: MDA-MB-361 Proliferation - 3 days

| IC50 multiple | GDC-0941 (nM) | T-DM1 ng/ml | Effect (%) | CI |
|---|---|---|---|---|
| 0.25x | 62.5 | 3.125 | 21.9 | 1.003 |
| 0.5x | 125 | 6.25 | 37.3 | 0.862 |
| 1x | 250 | 12.5 | 51.8 | 0.920 |
| 2x | 500 | 25 | 73.1 | 0.742 |
| 4x | 1000 | 50 | 82.3 | 0.917 |

Figure 28:
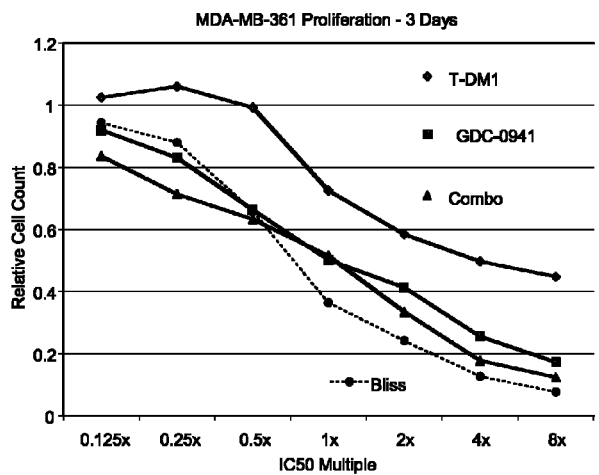
FIG. 28 shows a plot of MDA-0MB-361 in vitro cell viability (proliferation) at 3 days after treatment with T-DM1, GDC-0941, and 1:20 fixed dose ratio combinations of T-DM1 (3.125 to 100 ng/ml) and GDC-0941 (62.5 nM to 2 μM) at IC50 multiple concentrations from 0.125× to 8×. The Bliss prediction of additivity is plotted as the dotted line.

FIG. 28 shows a plot of MDA-MB-361 in vitro cell viability (proliferation) at 3 days after treatment with T-DM1, GDC-0941, and fixed dose ratio combinations of T-DM1 (3.125 to 100 ng/ml) and GDC-0941 (62.5 nM to 2 µM) at IC50 multiple concentrations from 0.125x to 8x. The Bliss prediction of additivity is plotted as the dotted line. Table 28 shows the Effect in the 10-90% inhibition range with calculated CI values and average CI of 0.813. T-DM1 combined with GDC-0941 results in additive anti-proliferative activity in the MDA-MB-361 cells, with the average CI=0.813.

TABLE 28

GDC-0941 + T-DM1: MDA-MB-361 Proliferation - 3 days

| IC50 multiple | GDC-0941 (nM) | T-DM1 ng/ml | Effect (%) | CI |
|---|---|---|---|---|
| 0.25x | 62.5 | 3.125 | 28.6 | 0.785 |
| 0.5x | 125 | 6.25 | 36.7 | 0.960 |
| 1x | 250 | 12.5 | 48.5 | 1.026 |

TABLE 28-continued

GDC-0941 + T-DM1: MDA-MB-361 Proliferation - 3 days

| IC50 multiple | GDC-0941 (nM) | T-DM1 ng/ml | Effect (%) | CI |
|---|---|---|---|---|
| 2x | 500 | 25 | 66.6 | 0.807 |
| 4x | 1000 | 50 | 82.2 | 0.590 |
| 8x | 2000 | 100 | 87.7 | 0.709 |

Figure 29:
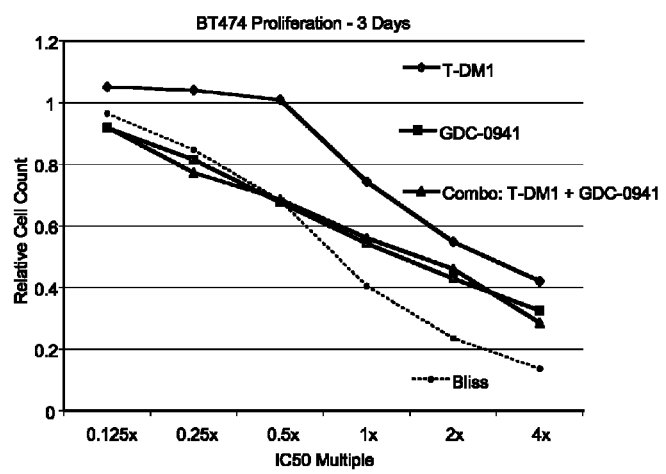
FIG. 29 shows a plot of BT-474 in vitro cell viability (proliferation) at 3 days after treatment with T-DM1, GDC-0941, and 1:10 fixed dose ratio combinations of T-DM1 (3.125 to 100 ng/ml) and GDC-0941 (31.25 nM to 1 μM) at IC50 multiple concentrations from 0.125× to 4×. The Bliss prediction of additivity is plotted as the dotted line.

FIG. 29 shows a plot of BT-474 in vitro cell viability (proliferation) at 3 days after treatment with T-DM1, GDC-0941, and fixed dose ratio combinations of T-DM1 (3.125 to 100 ng/ml) and GDC-0941 (31.25 nM to 1 µM) at IC50 multiple concentrations from 0.125× to 4×. The Bliss prediction of additivity is plotted as the dotted line. Table 29 shows the effect in the 10-90% inhibition range with calculated CI values and average CI of 1.2122. GDC-0941 and T-DM1 do not have a combination effect on BT-474, using these dose ratios.

TABLE 29

GDC-0941 + T-DM1: BT-474 Proliferation - 3 days

| IC50 multiple | GDC-0941 (nM) | T-DM1 ng/ml | Effect (%) | CI |
|---|---|---|---|---|
| 0.125x | 31.25 | 3.125 | 8.0 | >2 |
| 0.25x | 62.5 | 6.25 | 22.7 | 1.032 |
| 0.5x | 125 | 12.5 | 31.4 | 1.178 |
| 1x | 250 | 25 | 43.9 | 1.207 |
| 2x | 500 | 50 | 53.9 | 1.473 |
| 4x | 1000 | 100 | 71.5 | 1.171 |

Figure 30:
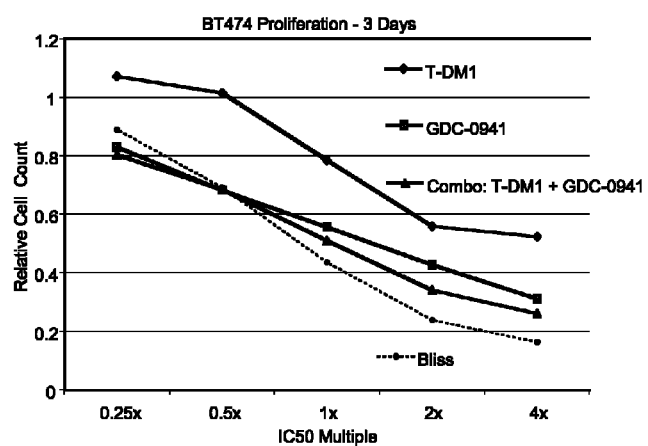
FIG. 30 shows a plot of BT-474 in vitro cell viability (proliferation) at 3 days after treatment with T-DM1, GDC-0941, and 1:10 fixed dose ratio combinations of T-DM1 (6.25 to 100 ng/ml) and GDC-0941 (62.5 nM to 1 μM) at IC50 multiple concentrations from 0.25× to 4×. The Bliss prediction of additivity is plotted as the dotted line.

FIG. 30 shows a plot of BT-474 in vitro cell viability (proliferation) at 3 days after treatment with T-DM1, GDC-0941, and fixed dose ratio combinations of T-DM1 (6.25 to 100 ng/ml) and GDC-0941 (62.5 nM to 1 µM) at IC50 multiple concentrations from 0.25× to 4×. The Bliss prediction of additivity is plotted as the dotted line. Table 30 shows the effect in the 10-90% inhibition range with calculated CI values and average CI of 0.997, indicating additivity.

TABLE 30

GDC-0941 + T-DM1: BT-474 Proliferation - 3 days

| IC50 multiple | GDC-0941 (nM) | T-DM1 ng/ml | Effect (%) | CI |
|---|---|---|---|---|
| 0.25x | 62.5 | 6.25 | 19.7 | 1.338 |
| 0.5x | 125 | 12.5 | 31.5 | 1.167 |
| 1x | 250 | 25 | 49.0 | 0.886 |
| 2x | 500 | 50 | 66.0 | 0.708 |
| 4x | 1000 | 100 | 73.9 | 0.886 |

Figure 31:
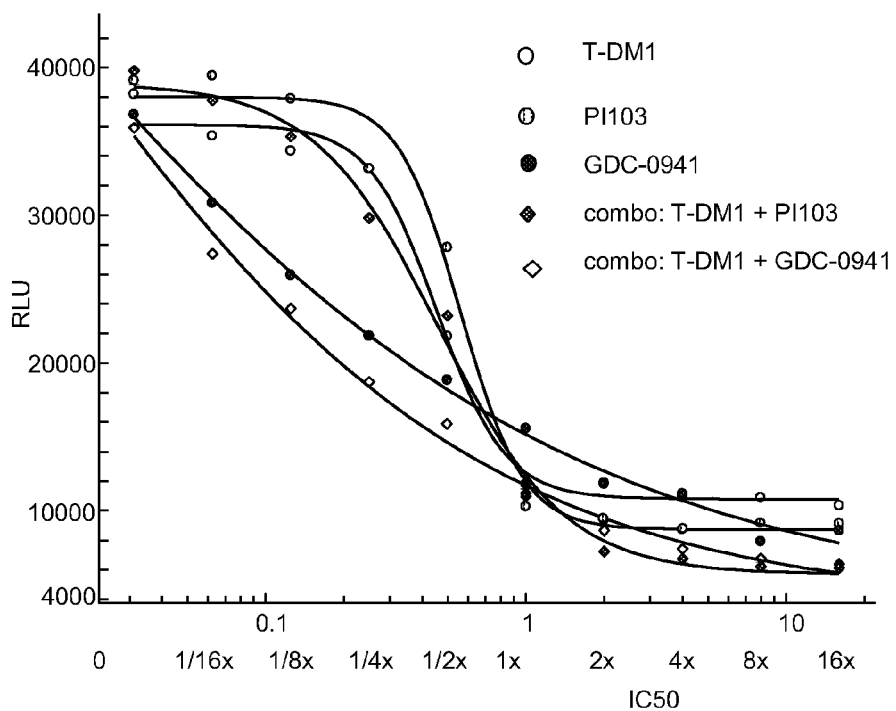
FIG. 31 shows a plot of Her2 amplified, non-PI3K mutant, AU565 cells in vitro cell viability (proliferation) at 3 days after treatment with T-DM1, PI103, GDC-0941, and fixed dose ratio combinations of T-DM1+PI103, and T-DM1+GDC-0941 at IC50 multiple concentrations from 0 to 16×.

FIG. 31 shows a plot of Her2 amplified, non-PI3K mutant, AU565 cells in vitro cell viability (proliferation) at 3 days after treatment with T-DM1, PI103, GDC-0941, and fixed dose ratio combinations of T-DM1+PI103, and T-DM1+GDC-0941 at IC50 multiple concentrations from 0 to 16×. Table 31 shows the Combination Index values. The results suggest in vitro antagonism between T-DM-1 and GDC-0941 since the CI values are between >1, and additivity or slight antagonism between T-DM-1 and PI103 since CI values are near or slightly greater than 1.

TABLE 31

Combinations: AU565 Proliferation

| CI at: | T-DM1 + GDC-0941 | T-DM1 + PI103 |
|---|---|---|
| ED50 | 1.19123 | 1.12269 |
| ED75 | 1.36342 | 0.97338 |
| ED90 | 1.56063 | 0.84956 |

Figure 32:
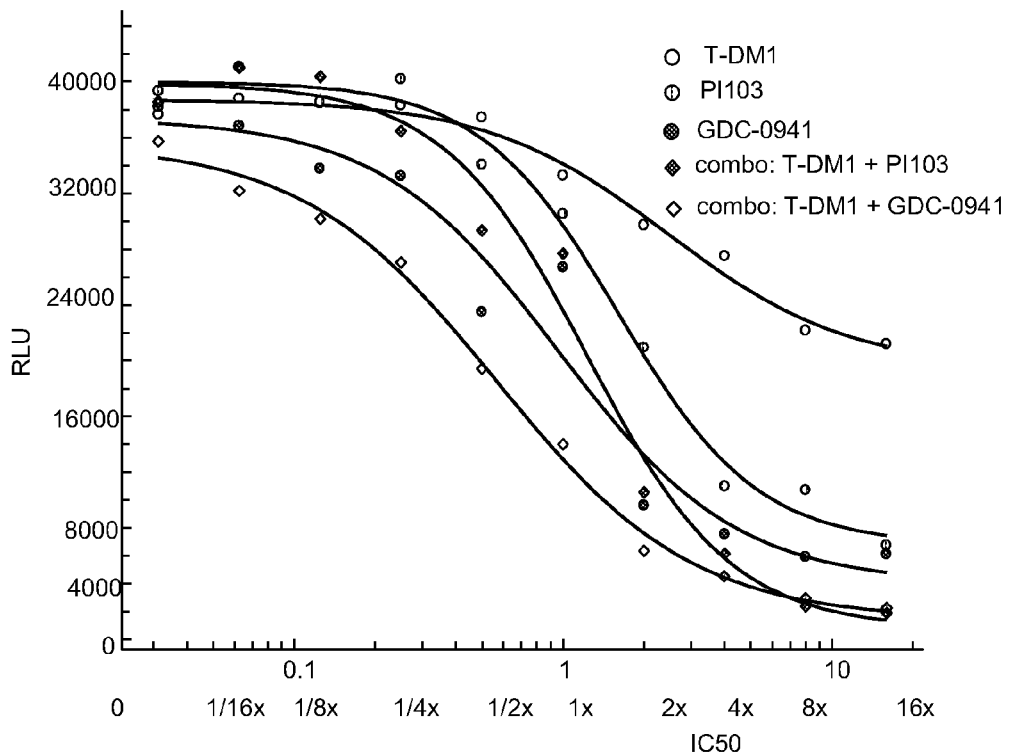
FIG. 32 shows a plot of Her2 amplified, PIK3CA (C420R) mutant, EFM192A cells in vitro cell viability (proliferation) at 3 days after treatment with T-DM1, PI103, GDC-0941, and fixed dose ratio combinations of T-DM1+PI103, and T-DM1+GDC-0941, at IC50 multiple concentrations from 0 to 16×.

FIG. 32 shows a plot of Her2 amplified, PIK3CA (C420R) mutant, EFM192A cells in vitro cell viability (proliferation) at 3 days after treatment with T-DM1, PI103, GDC-0941, and fixed dose combinations of T-DM1+PI103, and T-DM1+GDC-0941, at IC50 multiple concentrations from 0 to 16×. Table 32 shows the Combination Index values. The results suggest moderate in vitro synergy between T-DM-1 and GDC-0941 since the CI values are between between 0.5 and 1, and synergy between T-DM-1 and PI103 since CI values are near 0.5.

TABLE 32

Combinations: EFM192A Proliferation

| CI at: | T-DM1 + GDC-0941 | T-DM1 + PI103 |
|---|---|---|
| ED50 | 0.80379 | 0.53861 |
| ED75 | 0.66352 | 0.52087 |
| ED90 | 0.5485 | 0.52001 |

Figure 33:
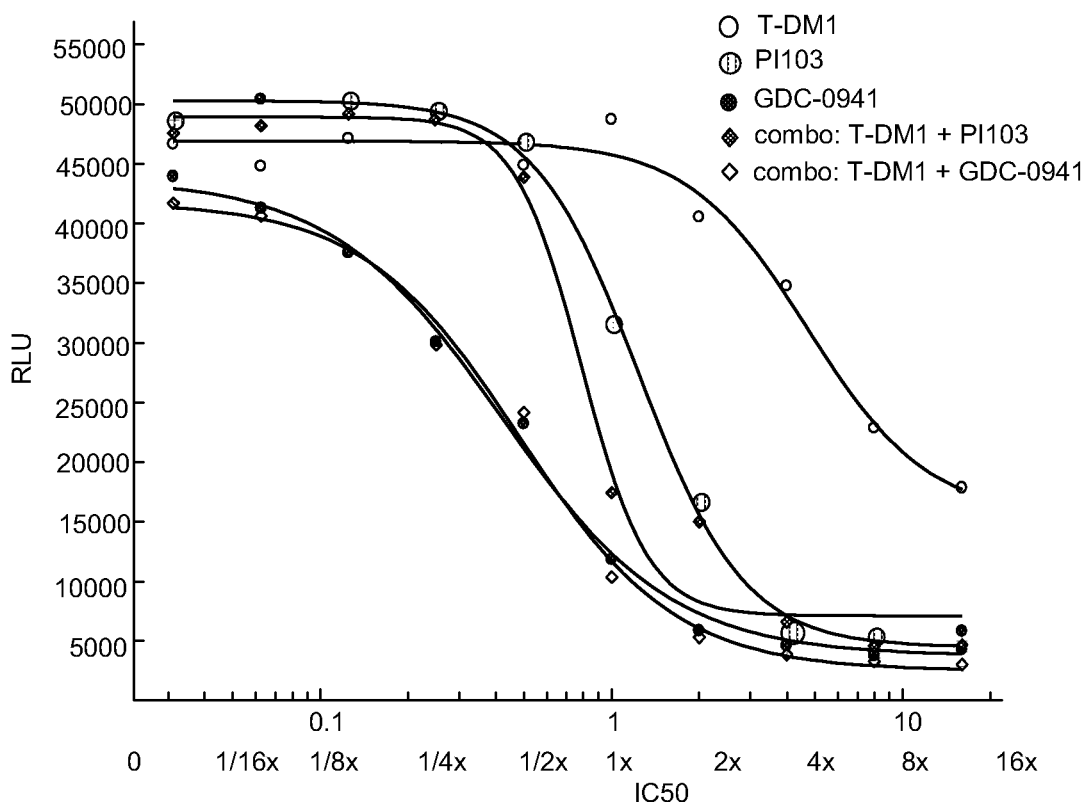
FIG. 33 shows a plot of Her2 amplified, HERCEPTIN® resistant, PIK3CA (H1047R) mutant, HCC1954 cells in vitro cell viability (proliferation) after treatment with T-DM1, PI103, GDC-0941, and fixed dose ratio combinations of T-DM1+PI103, and T-DM1+GDC-0941, at IC50 multiple concentrations from 0 to 16×.

FIG. 33 shows a plot of Her2 amplified, HERCEPTIN® resistant, PIK3CA (H1047R) mutant, HCC1954 cells in vitro cell viability (proliferation) at 3 days after treatment with T-DM1, PI103, GDC-0941, and fixed dose ratio combinations of T-DM1+PI103, and T-DM1+GDC-0941, at IC50 multiple concentrations from 0 to 16×. Table 33 shows the Combination Index values. The results suggest additivity or slight in vitro synergy between T-DM-1 and GDC-0941 since the CI values are close to 1, and slight synergy between T-DM-1 and PI103 since CI values are <1.

TABLE 33

Combinations: HCC1954 Proliferation

| CI at: | T-DM1 + GDC-0941 | T-DM1 + PI103 |
|---|---|---|
| ED50 | 1.15864 | 0.78902 |
| ED75 | 0.92365 | 0.78684 |
| ED90 | 0.74198 | 0.80771 |

In Vivo Tumor Xenograft Efficacy

The efficacy of the combinations of the invention may be measured in vivo by implanting allografts or xenografts of cancer cells in rodents and treating the tumors with the combinations. Variable results are to be expected depending on the cell line, the presence or absence of certain mutations in the tumor cells, the sequence of administration of trastuzumab-MCC-DM1 and chemotherapeutic agent, dosing regimen, and other factors. Subject mice were treated with drug(s) or control (Vehicle) and monitored over several weeks or more to measure the time to tumor doubling, log cell kill, and tumor inhibition (Example 3). FIGS. 10-17 and 34-37 show the efficacy of trastuzumab-MCC-DM1 in combinations with chemotherapeutic agents by xenograft tumor inhibition in mice.

Figure 10:
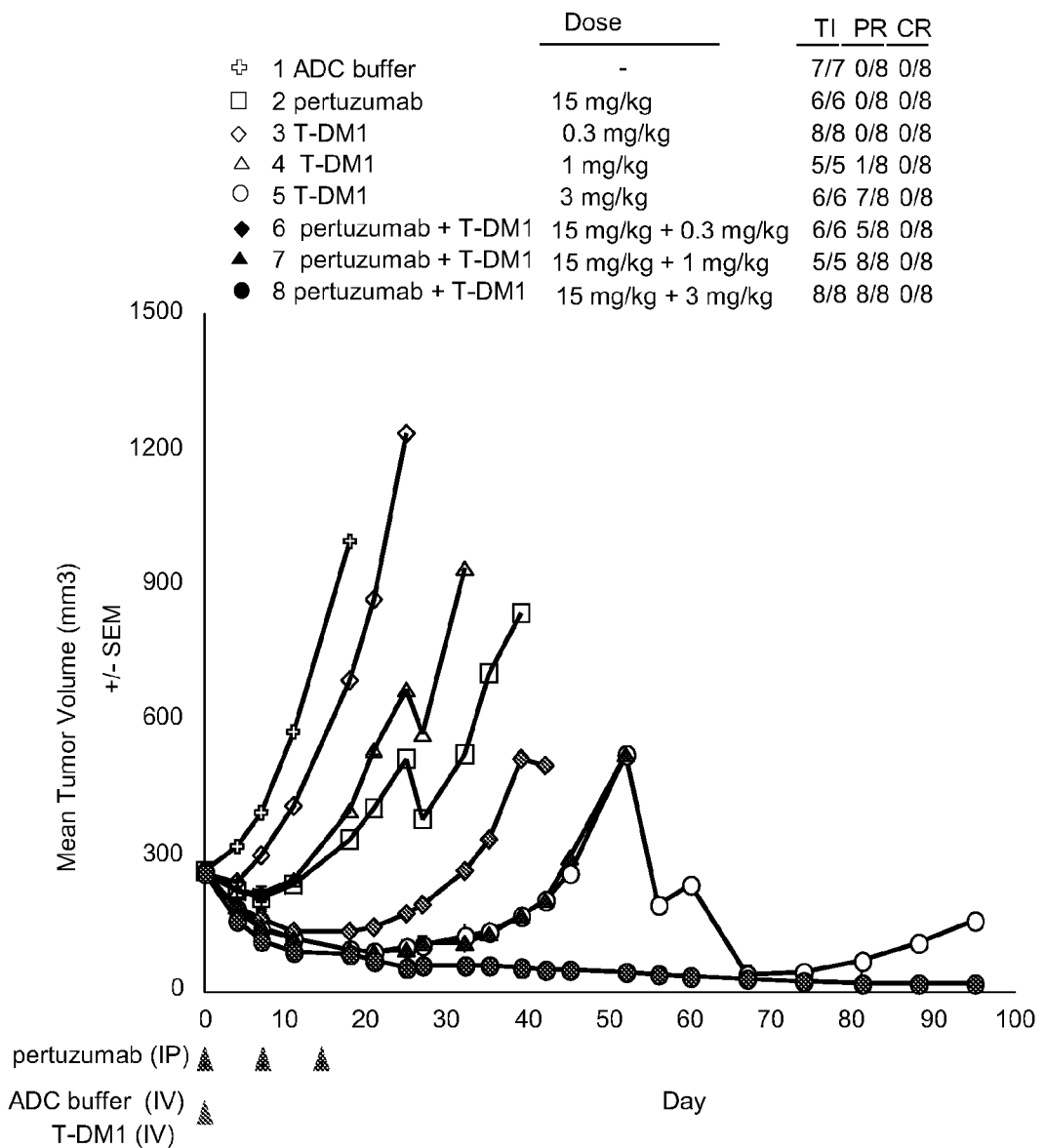
FIG. 10 shows a plot of the in vivo mean tumor volume change over time in KPL-4 tumors inoculated into the mammary fat pad of SCID beige mice (3 million cells in matrigel per mouse) after dosing with: (1) ADC buffer, (2) pertuzumab 15 mg/kg, (3) T-DM1 0.3 mg/kg, (4) T-DM1 1 mg/kg, (5) T-DM1 3 mg/kg, (6) pertuzumab 15 mg/kg+T-DM1 0.3 mg, (7) pertuzumab 15 mg/kg+T-DM1 1 mg/kg, (8) pertuzumab 15 mg/kg+T-DM1 3 mg/kg. ADC buffer and T-DM1 were dosed once on day 0. Pertuzumab was dosed on days 0, 7, and 14.

FIG. 10 shows a plot of the in vivo mean tumor volume change over time on KPL-4 tumors inoculated into the mammary fat pad of SCID beige mice after dosing with: (1) ADC buffer, (2) pertuzumab 15 mg/kg, (3) T-DM1 0.3 mg/kg, (4) T-DM1 1 mg/kg, (5) T-DM1 3 mg/kg, (6) pertuzumab 15 mg/kg+T-DM1 0.3 mg, (7) pertuzumab 15 mg/kg+T-DM1 1 mg/kg, (8) pertuzumab 15 mg/kg+T-DM1 3 mg/kg. Animals dosed with ADC buffer (1) gave 0 PR and 0 CR. Animals dosed with pertuzumab (2) at 15 mg/kg gave 0 PR and 0 CR. Animals dosed with T-DM1 at 0.3 mg/kg (3) alone gave 0 PR and 0 CR. Animals dosed with T-DM1 at 1 mg/kg (4) alone gave 1 PR and 0 CR. Animals dosed with T-DM1 at 3 mg/kg (5) alone gave 7 PR and 0 CR. Animals dosed with the combination of pertuzumab at 15 mg/kg and T-DM1 at 0.3 mg/kg (6) gave 5 PR and 0 CR. Animals dosed with the combination of pertuzumab at 15 mg/kg and T-DM1 at 1 mg/kg (7) gave 8 PR and 0 CR. Animals dosed with the combination of pertuzumab at 15 mg/kg and T-DM1 at 3 mg/kg (8) gave 8 PR and 0 CR. The combination of pertuzumab and T-DM1 results in greater anti-tumor activity in KPL4 xenografts than either agent alone.

Figure 11:
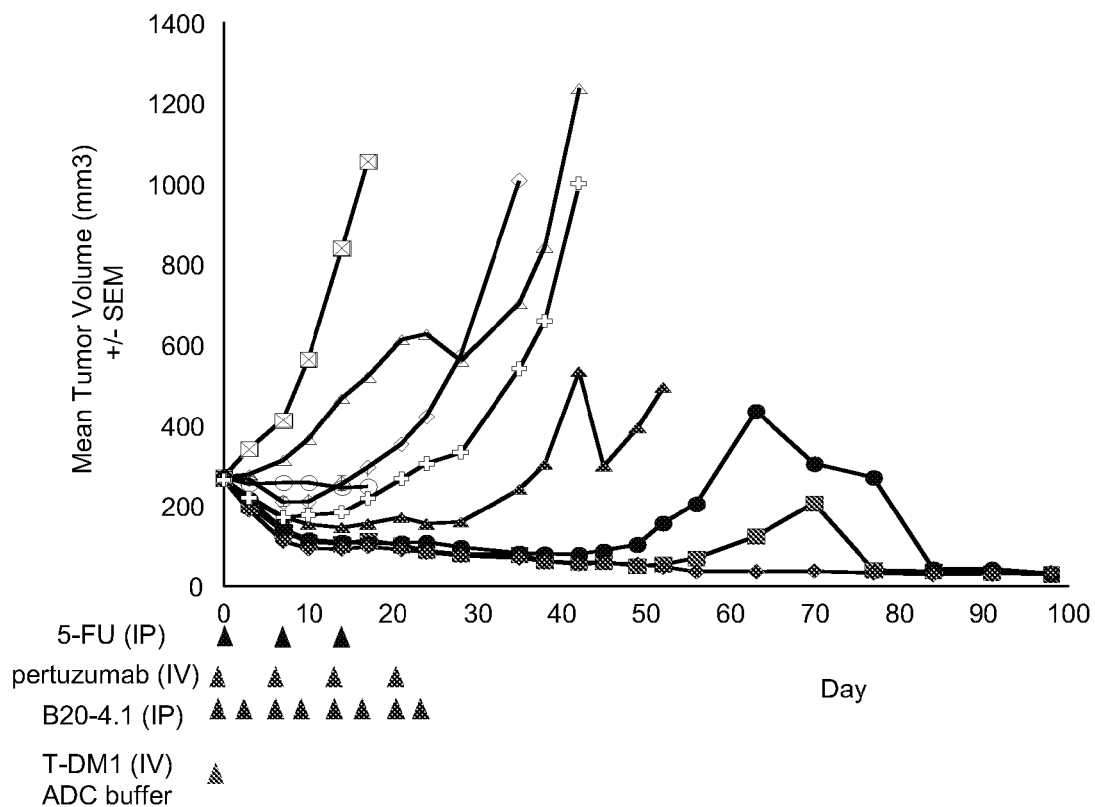
FIG. 11 shows a plot of the in vivo mean tumor volume change over time in KPL-4 tumors inoculated into the mammary fat pad of SCID beige mice (3 million cells in matrigel per mouse) after dosing with: (1) ADC buffer, (2) 5-FU 100 mg/kg, (3) pertuzumab 40 mg/kg, the first pertuzumab dose (groups 5, 7, and 9) was a 2× loading dose, (4) B20-4.1, 5 mg/kg, (5) T-DM1, 5 mg/kg, (6) 5-FU, 100 mg/kg+T-DM1, 5 mg, (7) pertuzumab 40 mg/kg+T-DM1, 5 mg/kg, (8) B20-4.1, 5 mg/kg+T-DM1, 5 mg/kg, (9) B20-4.1, 5 mg/kg+pertuzumab, 40 mg/kg. ADC buffer and T-DM1 were dosed once on day 0 by single iv injection. Pertuzumab was dosed on days 0, 7, 14, 21 (qwk×4. 5-FU was dosed on days 0, 7 and 14 (qwk×3). B20-4.1 was dosed on days 0, 3, 7, 10, 14, 17, 21 and 24 (2×/wk×8 total).

FIG. 11 shows a plot of the in vivo mean tumor volume change over time on KPL-4 tumors inoculated into the mammary fat pad of SCID beige mice after dosing with: (1) ADC buffer, (2) 5-FU 100 mg/kg, (3) pertuzumab, 40 mg/kg, (4) B20-4.1, 5 mg/kg, (5) T-DM1, 5 mg/kg, (6) 5-FU, 100 mg/kg+T-DM1, 5 mg, (7) pertuzumab, 40 mg/kg+T-DM1, 5 mg/kg, (8), –4.1 5 mg/kg+T-DM1, 5 mg/kg, (9) B20-4.1, 5 mg/kg+pertuzumab, 40 mg/kg. At the end of the study, all remaining tumors less than 50 mm$^3$ volume were histologically evaluated and determined that 8 samples in single agent (5) T-DM1, 5 mg/kg, 5 samples in combination group (6) 5-FU, 100 mg/kg+T-DM1, 5 mg, and 8 samples in combination group (7) pertuzumab, 40 mg/kg+T-DM1, 5 mg/kg had no evidence of viable tumor cells.

Figure 12:
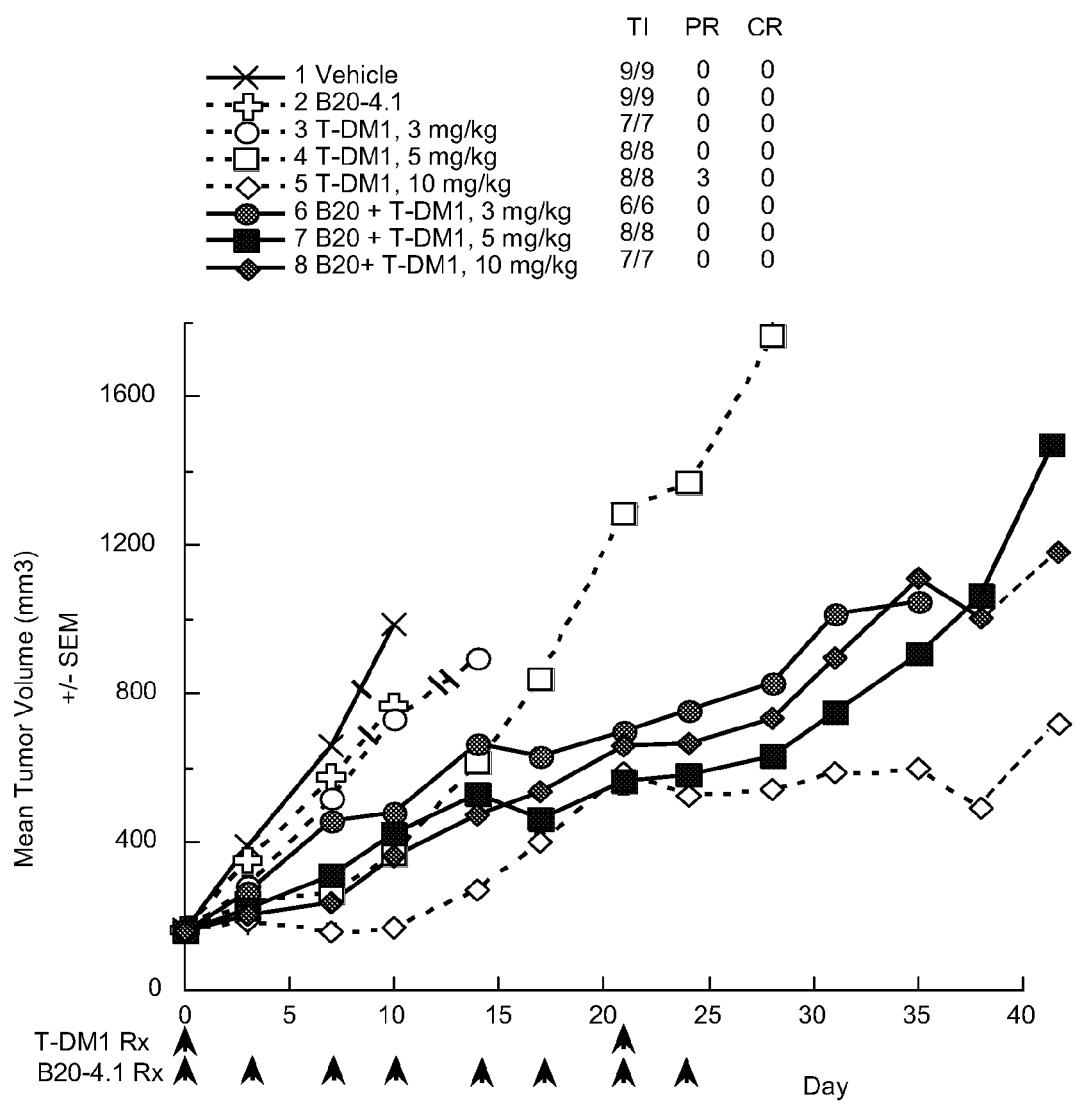
FIG. 12 shows a plot of the in vivo mean tumor volume change over time in MMTV-HER2 Fo5 transgenic mammary tumors inoculated into the mammary fat pad of CRL nu/nu mice after dosing with: (1) Vehicle (ADC buffer), (2) B20-4.1, 5 mg/kg, (3) T-DM1, 3 mg/kg, (4) T-DM1, 5 mg/kg, (5) T-DM1, 10 mg/kg, (6) B20-4.1, 5 mg/kg+T-DM1 3 mg/kg, (7) B20-4.1, 5 mg/kg+T-DM1 5 mg/kg, (8) B20-4.1, 5 mg/kg+T-DM1, 10 mg/kg. ADC buffer and T-DM1 were dosed on days 0 and 21. B20-4.1 was dosed on days 0, 3, 7, 10, 14, 17, 21 and 24 (2×/wk×4 for 8 total).

FIG. 12 shows a plot of the in vivo mean tumor volume change over time on MMTV-HER2 Fo5 transgenic mammary tumor inoculated into the mammary fat pad of CRL nu/nu mice after dosing with: (1) Vehicle (ADC buffer), (2) B20-4.1, 5 mg/kg, (3) T-DM1, 3 mg/kg, (4) T-DM1, 5 mg/kg, (5) T-DM1, 10 mg/kg, (6) B20-4.1, 5 mg/kg+T-DM1, 3 mg/kg, (7) B20-4.1, 5 mg/kg+T-DM1, 5 mg/kg, (8) B20-4.1, 5 mg/kg+T-DM1, 10 mg/kg. The combination of T-DM1 and B20-4.1 results in enhanced tumor growth inhibition with T-DM1 of 3 and 5 mg/kg, but not 10 mg/kg.

Figure 13:
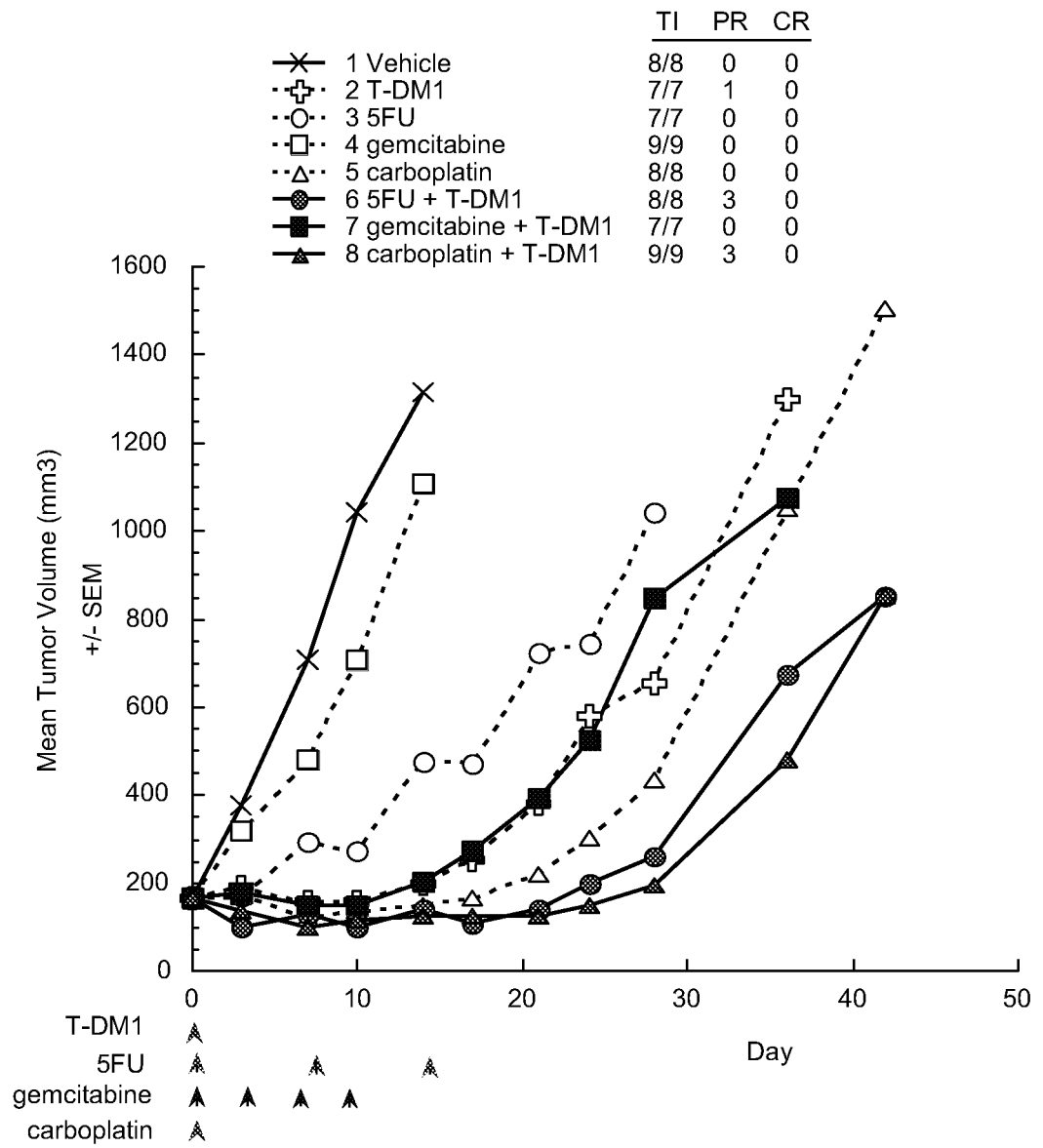
FIG. 13 shows a plot of the in vivo mean tumor volume change over time in MMTV-HER2 Fo5 transgenic mammary tumors inoculated into the mammary fat pad of CRL nu/nu mice after dosing with: (1) Vehicle (ADC buffer), (2) T-DM1 10 mg/kg, (3) 5-FU 100 mg/kg, (4) gemcitabine 120 mg/kg, (5) carboplatin 100 mg/kg, (6) 5-FU 100 mg/kg+T-DM1 10 mg/kg, (7) gemcitabine 120 mg/kg+T-DM1 10 mg/kg, (8) carboplatin 100 mg/kg+T-DM1 10 mg/kg. ADC buffer, T-DM1 and carboplatin were dosed on day 0; single injection. 5-FU was dosed on day 0, 7 and 14 (qwk×3). Gemcitabine was dosed on days 0, 3, 6 and 9 (q3d×4).

FIG. 13 shows a plot of the in vivo mean tumor volume change over time on MMTV-HER2 Fo5 transgenic mammary tumor inoculated into the mammary fat pad of CRL nu/nu mice after dosing with: (1) Vehicle (ADC buffer), (2) T-DM1, 10 mg/kg, (3) 5-FU, 100 mg/kg, (4) gemcitabine, 120 mg/kg, (5) carboplatin, 100 mg/kg, (6) 5-FU, 100 mg/kg+T-DM1, 10 mg/kg, (7) gemcitabine, 120 mg/kg+T-DM1, 10 mg/kg, (8) carboplatin, 100 mg/kg+T-DM1, 10 mg/kg. T-DM1 combined with either 5-FU, carboplatin or gemcitabine results in enhanced anti-tumor efficacy compared to single agent treatment.

Figure 14:
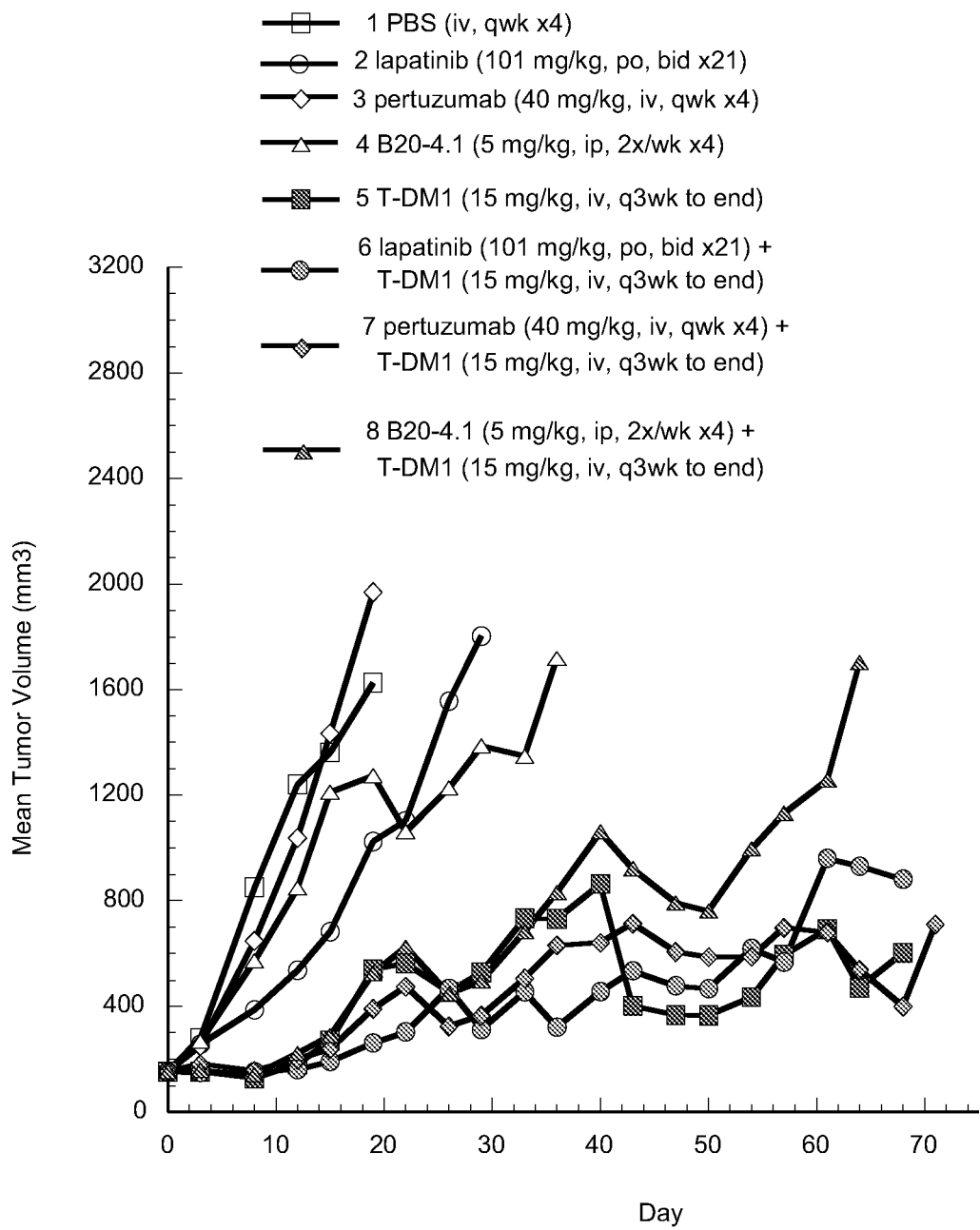
FIG. 14 shows a plot of the in vivo mean tumor volume change over time in MMTV-Her2 Fo5 transgenic mammary tumors inoculated into the mammary fat pad of Harlan athymic nude mice after dosing with: (1) Vehicle (PBS buffer) iv, qwk×4, (2) lapatinib 101 mg/kg, po, bid×21, (3) pertuzumab 40 mg/kg, iv, qwk×4, (4) B20-4.1 5 mg/kg, ip, 2×/wk×4, (5) T-DM1 15 mg/kg, iv, q3wk to end, (6) lapatinib 101 mg/kg, po, bid×21+T-DM1 15 mg/kg, iv, q3wk to end (7) pertuzumab 40 mg/kg, iv, qwk×4+T-DM1 15 mg/kg, iv, q3wk to end, (8) B20-4.1 5 mg/kg, ip, 2×/wk×4+T-DM1 15 mg/kg, iv, q3wk to end.

FIG. 14 shows a plot of the in vivo mean tumor volume change over time on MMTV-Her2 Fo5 transgenic mammary tumor xenografts inoculated into the mammary fat pad of Harlan athymic nude mice after dosing with: (1) Vehicle (PBS buffer) iv, qwk×4, (2) lapatinib, 101 mg/kg, po, bid×21, (3) pertuzumab, 40 mg/kg, iv, qwk×4, (4) B20-4.1, 5 mg/kg, ip, 2×/wk×4, (5) T-DM1, 15 mg/kg, iv, q3wk to end, (6) lapatinib, 101 mg/kg, po, bid×21+T-DM1, 15 mg/kg, iv, q3wk to end (7) pertuzumab, 40 mg/kg, iv, qwk×4+T-DM1, 15 mg/kg, iv, q3wk to end, (8) B20-4.1, 5 mg/kg, ip, 2×/wk×4+T-DM1, 15 mg/kg, iv, q3wk to end.

The single agent T-DM1 at 15 mg/kg dose (5) is not significantly different from the combination of T-DM1 at 15 mg/kg and B20-4.1 at 5 mg/kg (8). Lapatinib and pertuzumab were not different from vehicle in this study. B20-4.1 showed a trend towards increased efficacy compared to vehicle. T-DM1 was efficacious as a single agent (p<0.01). The combination of T-DM1 with lapatinib was significantly better than lapatinib alone (p<0.01), but not different than T-DM1 alone. The combination of T-DM1 with pertuzumab was significantly better than pertuzumab alone (p<0.01), but not different than T-DM1 alone. The combination of T-DM1 with B20-4.1 was significantly better than B20-4.1 alone (p<0.01), but not different than T-DM1 alone.

Figure 15:
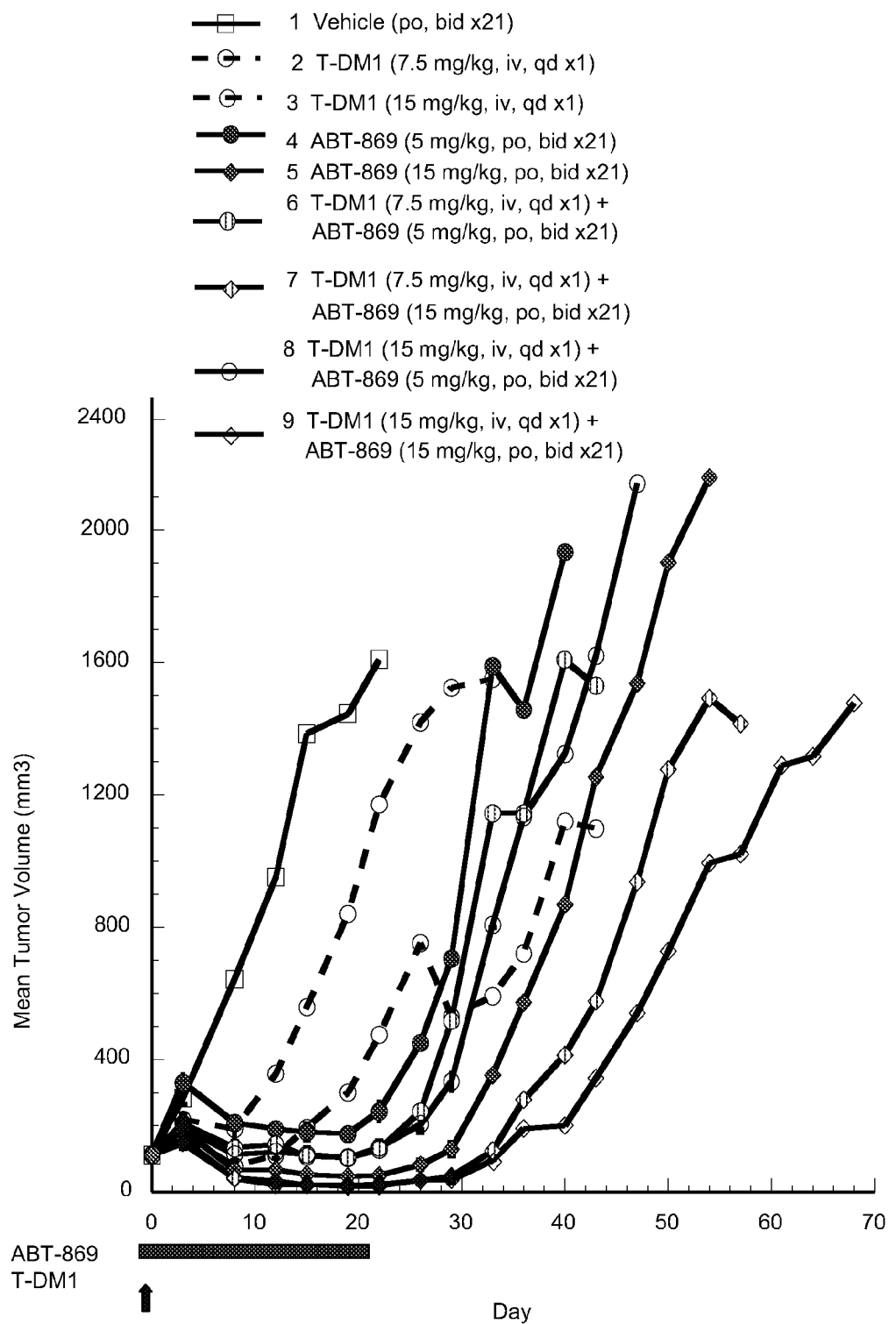
FIG. 15 shows a plot of the in vivo mean tumor volume change over time on MMTV-Her2 Fo5 transgenic mammary tumor inoculated into the mammary fat pad of Harlan athymic nude mice after dosing with: (1) Vehicle (PBS buffer) po, bid×21 (2) T-DM1, 7.5 mg/kg, iv, qd×1 (3) T-DM1, 15 mg/kg, iv, qd×1 (4) ABT-869, 5 mg/kg, po, bid×21 (5) ABT-869, 15 mg/kg, po, bid×21 (6) T-DM1, 7.5 mg/kg, iv, qd×1+ABT-869, 5 mg/kg, po, bid×21 (7) T-DM1 7.5 mg/kg, iv, qd×1+ABT-869, 15 mg/kg, po, bid×21 (8) T-DM1, 15 mg/kg, iv, qd×1+ABT-869, 5 mg/kg, po, bid×21 (9) T-DM1, 15 mg/kg, iv, qd×1+ABT-869, 15 mg/kg, po, bid×21.

FIG. 15 shows a plot of the in vivo efficacy by mean tumor volume change over time on MMTV-Her2 Fo5 transgenic mammary tumor xenografts inoculated into the mammary fat pad of Harlan athymic nude mice after dosing with: (1) Vehicle (PBS buffer) po, bid×21 (2) T-DM1, 7.5 mg/kg, iv, qd×1 (3) T-DM1, 15 mg/kg, iv, qd×1 (4) ABT-869, 5 mg/kg, po, bid×21 (5) ABT-869, 15 mg/kg, po, bid×21 (6) T-DM1, 7.5 mg/kg, iv, qd×1+ABT-869, 5 mg/kg, po, bid×21 (7) T-DM1 7.5 mg/kg, iv, qd×1+ABT-869, 15 mg/kg, po, bid×21 (8) T-DM1, 15 mg/kg, iv, qd×1+ABT-869, 5 mg/kg, po, bid× 21 (9) T-DM1, 15 mg/kg, iv, qd×1+ABT-869, 15 mg/kg, po, bid×21.

The combination of T-DM1 and ABT-869, 5 mg/kg showed two partial responses (8), and is not significantly more efficacious than single agent ABT-869, 5 mg/kg (4). The combination of T-DM1 and ABT-869, 15 mg/kg (9) is slightly more efficacious than single agent ABT-869, 15 mg/kg (5). ABT-869 dosed at 5 mg/kg was significantly better than vehicle by time to endpoint (p<0.01), but was not different than vehicle by time to tumor doubling. ABT-869 dosed at 15 mg/kg and T-DM1 dosed at either 7.5 or 15 mg/kg were significantly better than vehicle by both time to tumor doubling and time to tumor endpoint (p<0.01). The combination of 7.5 mg/kg T-DM1 and 5 mg/kg ABT-869 was not different than the single agent of 7.5 mg/kg T-DM1. Compared to single agent 5 mg/kg ABT-869, the combination of 7.5 mg/kg T-DM1+5 mg/kg ABT-869 was significantly better by time to tumor doubling (p<0.01), but was not different by time to endpoint. The combination of 7.5 mg/kg T-DM1 and 15 mg/kg ABT-869 was significantly better than either single agent (p<0.01). The combination of 15 mg/kg T-DM1+5 mg/kg ABT-869 was not different than 15 mg/kg T-DM1 single agent. Compared to 5 mg/kg ABT-869 single agent, the combination of 15 mg/kg T-DM1 and 5 mg/kg ABT-869 was not different by time to endpoint, but was significantly different by time to tumor doubling (p<0.01). The combination of 15 mg/kg T-DM1+15 mg/kg ABT-869 was significantly better than 15 mg/kg ABT-869 alone and was better than 15 mg/kg T-DM1 alone by time to tumor doubling (p<0.01). The time to endpoint of 15 mg/kg T-DM1 and 15 mg/kg T-DM1+15 mg/kg ABT-869 was not different.

Figure 16:
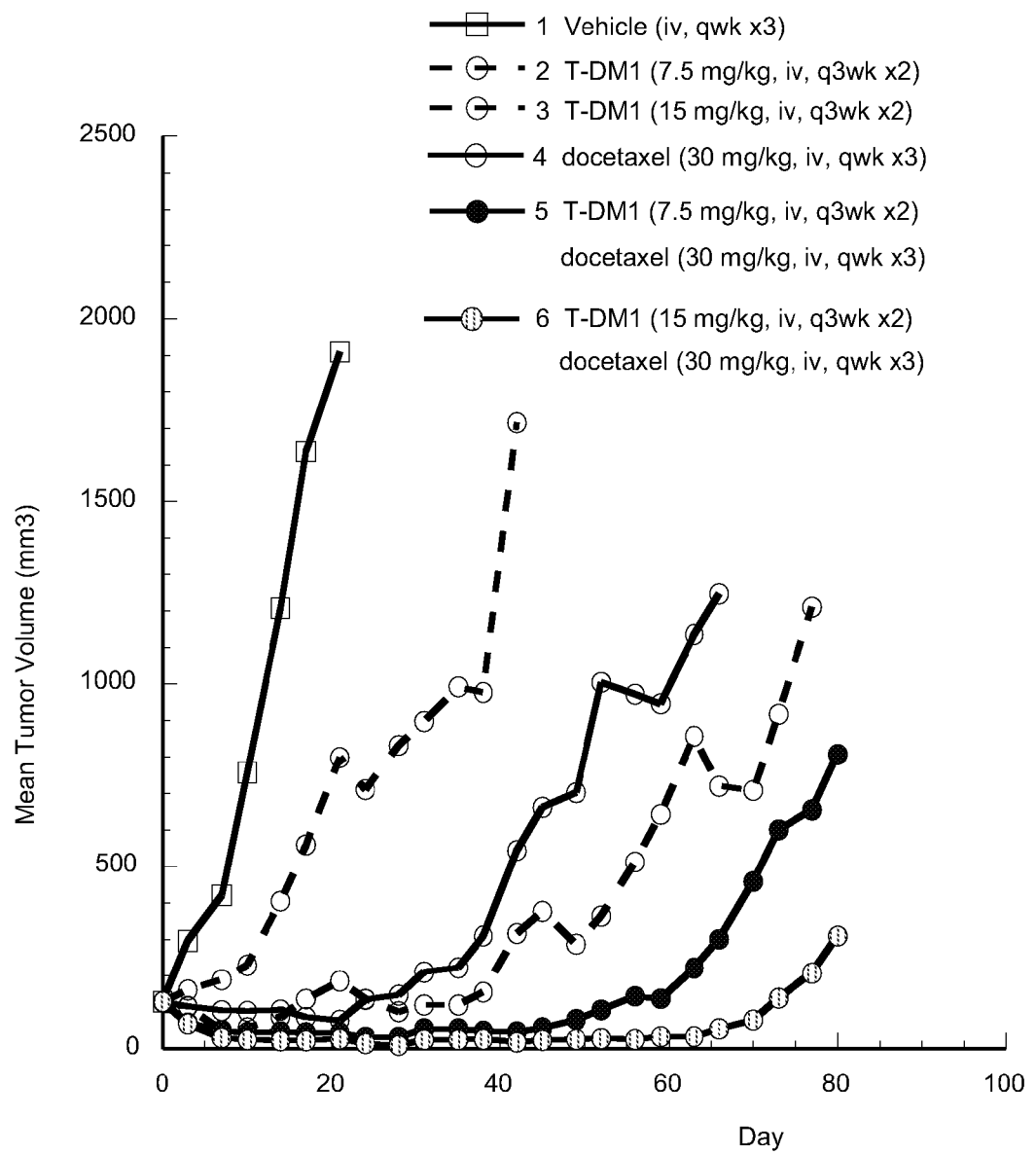
FIG. 16 shows a plot of the in vivo mean tumor volume change over time on MMTV-Her2 Fo5 transgenic mammary tumor inoculated into the mammary fat pad of Harlan athymic nude mice after dosing with: (1) Vehicle, iv, qwk×3 (2) T-DM1, 7.5 mg/kg, iv, q3wk×2 (3) T-DM1, 15 mg/kg, iv, q3wk×2 (4) docetaxel, 30 mg/kg, iv, qwk×3 (5) T-DM1, 7.5 mg/kg, iv, q3wk×2+docetaxel, 30 mg/kg, iv, qwk×3 (6) T-DM1, 15 mg/kg, iv, q3wk×2+docetaxel, 30 mg/kg, iv, qwk×3

FIG. 16 shows a plot of the in vivo mean tumor volume change over time on MMTV-Her2 Fo5 transgenic mammary tumor xenografts inoculated into the mammary fat pad of Harlan athymic nude mice after dosing with: (1) Vehicle. iv. qwk×3 (2) T-DM1, 7.5 mg/kg, iv, q3wk×2 (3) T-DM1, 15 mg/kg, iv, q3wk×2 (4) docetaxel, 30 mg/kg, iv, qwk×3 (5) T-DM1, 7.5 mg/kg, iv, q3wk×2+docetaxel, 30 mg/kg, iv, qwk×3 (6) T-DM1, 15 mg/kg, iv, q3wk×2+docetaxel, 30 mg/kg, iv, qwk×3.

Animals dosed with T-DM1 at 15 mg/kg (3) alone gave 6 partial responses (PR) and 1 complete response (CR). Animals dosed with docetaxel alone at 30 mg/kg (4) gave 2 PR. Animals dosed with the combination of T-DM1 at 7.5 mg/kg and docetaxel at 30 mg/kg (5) gave 10 PR. Animals dosed with the combination of T-DM1 at 15 mg/kg and docetaxel at 30 mg/kg (6) showed a dose response with 7 PR and 3 CR. All single agent groups were significantly different than the vehicle group (p<0.01). The combination of 7.5 mg/kg T-DM1+docetaxel was significantly better than either single agent by both time to tumor doubling and time to endpoint (p<0.01). There were no objective responses in the 7.5 mg/kg T-DM1 group and 2 partial responses (PR) in the docetaxel single agent group. The combination of 7.5 mg/kg T-DM1 and docetaxel resulted in 9 PRs and 1 complete response (CR). The combination of 15 mg/kg T-DM1+docetaxel was significantly better than either single agent by time to tumor doubling and time to endpoint (p<0.01). The single agent 15 mg/kg T-DM1 treatment resulted in 5 PRs and 2 CRs. The combination of 15 mg/kg T-DM1+docetaxel increased the objective response rate to 7 PRs and 3 CRs. All mice in this combination group had an objective response to treatment.

Figure 17:
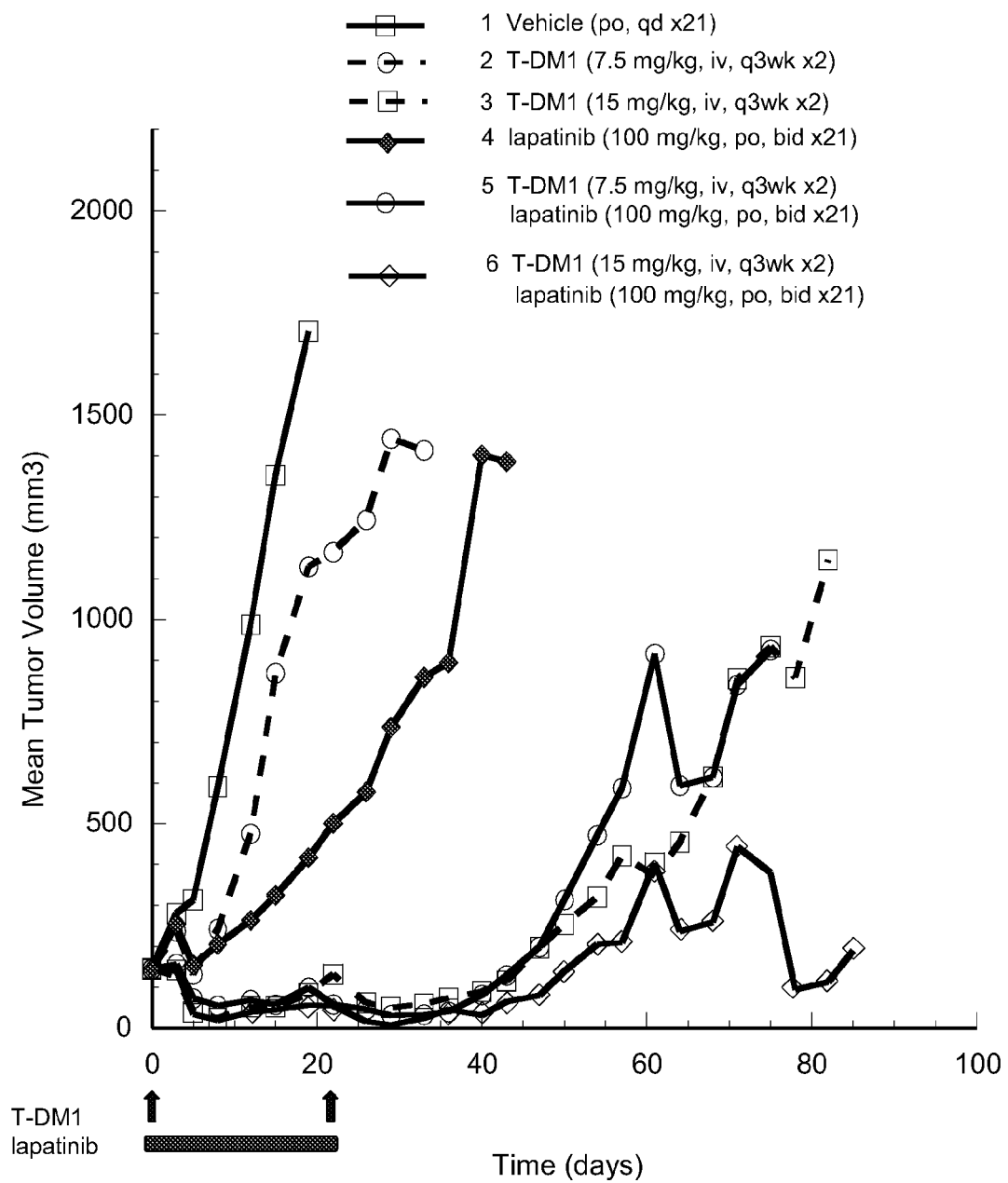
FIG. 17 shows a plot of the in vivo mean tumor volume change over time on MMTV-Her2 Fo5 transgenic mammary tumor inoculated into the mammary fat pad of Harlan athymic nude mice after dosing with: (1) Vehicle, po, qd×21 (2) T-DM1, 7.5 mg/kg, iv, q3wk×2, (3) T-DM1, 15 mg/kg, iv, q3wk×2 (4) lapatinib, 100 mg/kg, po, bid×21, (5) T-DM1, 7.5 mg/kg, iv, q3wk×2+lapatinib, 100 mg/kg, po, bid×21, (6) T-DM1, 15 mg/kg, iv, q3wk×2+lapatinib, 100 mg/kg, po, bid×21

FIG. 17 shows a plot of the in vivo mean tumor volume change over time on MMTV-Her2 Fo5 transgenic mammary tumor xenografts inoculated into the mammary fat pad of Harlan athymic nude mice after dosing with: (1) Vehicle, po, qd×21 (2) T-DM1, 7.5 mg/kg, iv, q3wk×2, (3) T-DM1, 15 mg/kg, iv, q3wk×2 (4) lapatinib, 100 mg/kg, po, bid×21, (5) T-DM1, 7.5 mg/kg, iv, q3wk×2+lapatinib, 100 mg/kg, po, bid×21, (6) T-DM1, 15 mg/kg, iv, q3wk×2+lapatinib, 100 mg/kg, po, bid×21.

Animals dosed with T-DM1 at 15 mg/kg (3) alone gave 6 partial responses (PR) and 3 complete responses (CR). Animals dosed with the combination of T-DM1 at 7.5 mg/kg and lapatinib at 100 mg/kg (5) gave 4 PR and 5 CR. Animals dosed with the combination of T-DM1 at 15 mg/kg and lapatinib at 100 mg/kg (6) showed a dose response with 8 CR. All single agent groups were significantly different from vehicle (p<0.01) by both time to tumor doubling and time to endpoint. T-DM1 dosed at 7.5 mg/kg in combination with lapatinib was significantly better than either lapatinib or T-DM1 at 7.5 mg/kg as a single agent (p<0.01). T-DM1 dosed at 15 mg/kg in combination with lapatinib was significantly better than lapatinib single agent (p<0.01). This combination was not different than 15 mg/kg of T-DM1 dosed as a single agent.

The time to tumor doubling was measured by Kaplan-Meier statistical analysis as 2× Vo. Time to tumor doubling and survival analysis were quantified by Log-rank-p values. Time to progression is measured as the elapsed time for tumor volume to reach 1000 mm$^3$, or the survival time if 1000 mm$^3$ tumor volume is not reached. T-DM1 combined with lapatinib resulted in greatly enhanced anti-tumor efficacy compared to single agent treatment.

Figure 34:
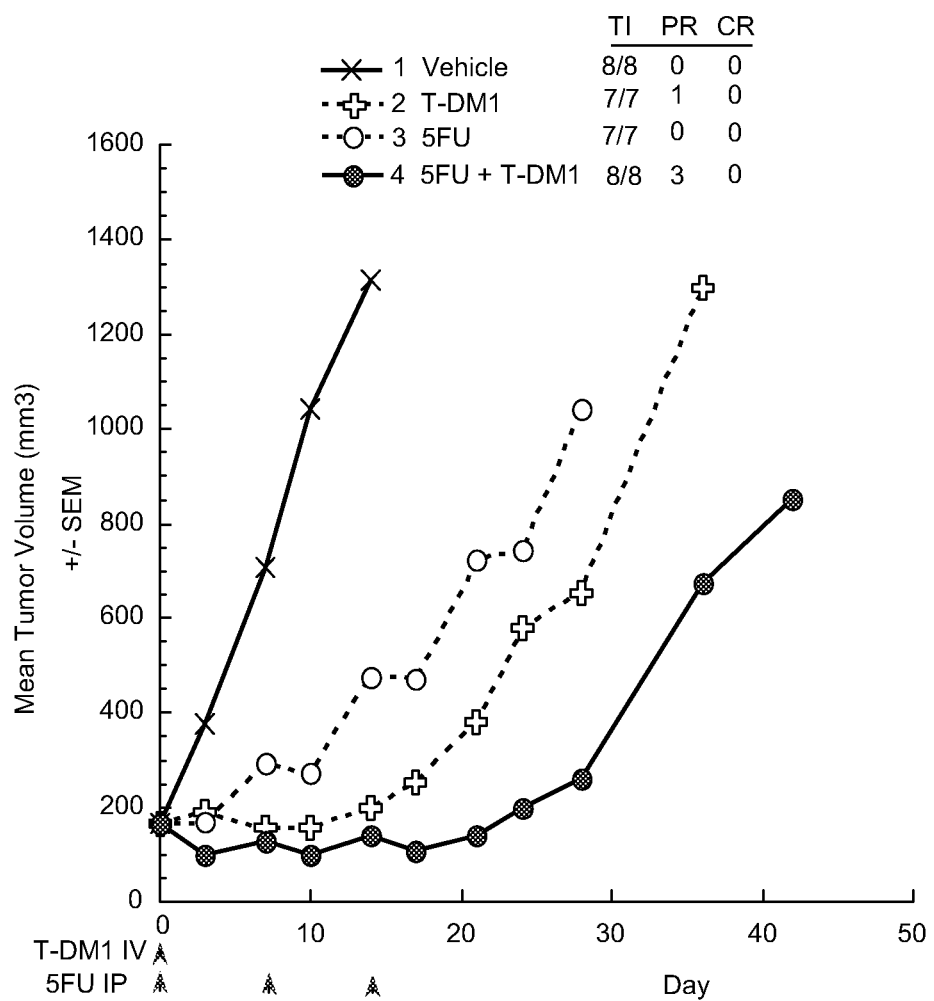
FIG. 34 shows a plot of the in vivo mean tumor volume change over time on MMTV-Her2 Fo5 transgenic mammary tumor inoculated into CRL nu/nu mice after dosing with: (1) Vehicle, po, qd×21 (2) T-DM1, 10 mg/kg, iv, q3wk, (3) 5-FU, 100 mg/kg, po, qwk×2, (4) T-DM1, 5 mg/kg, iv, q3wk+5-FU, 100 mg/kg, po, qwk×2

FIG. 34 shows a plot of the in vivo mean tumor volume change over time on MMTV-Her2 Fo5 transgenic mammary tumor inoculated into CRL nu/nu mice after dosing with: (1) Vehicle, po, qd×21 (2) T-DM1, 10 mg/kg, iv, q3wk, (3) 5-FU, 100 mg/kg, po, qwk×2, (4) (5) T-DM1, 5 mg/kg, iv, q3wk+ 5-FU, 100 mg/kg, po, qwk×2. Animals dosed with Vehicle gave 0 partial responses (PR) and 0 complete responses (CR). Animals dosed with T-DM1 gave 1 PR and 0 CR. Animals dosed with 5-FU gave 0 PR and 0 CR. Animals dosed with the combination of T-DM1 and 5-FU gave 3 PR and 0 CR at the 42 day time point. Treatment with T-DM1 and 5-FU results in enhanced anti-tumor activity compared to either agent alone.

Figure 35:
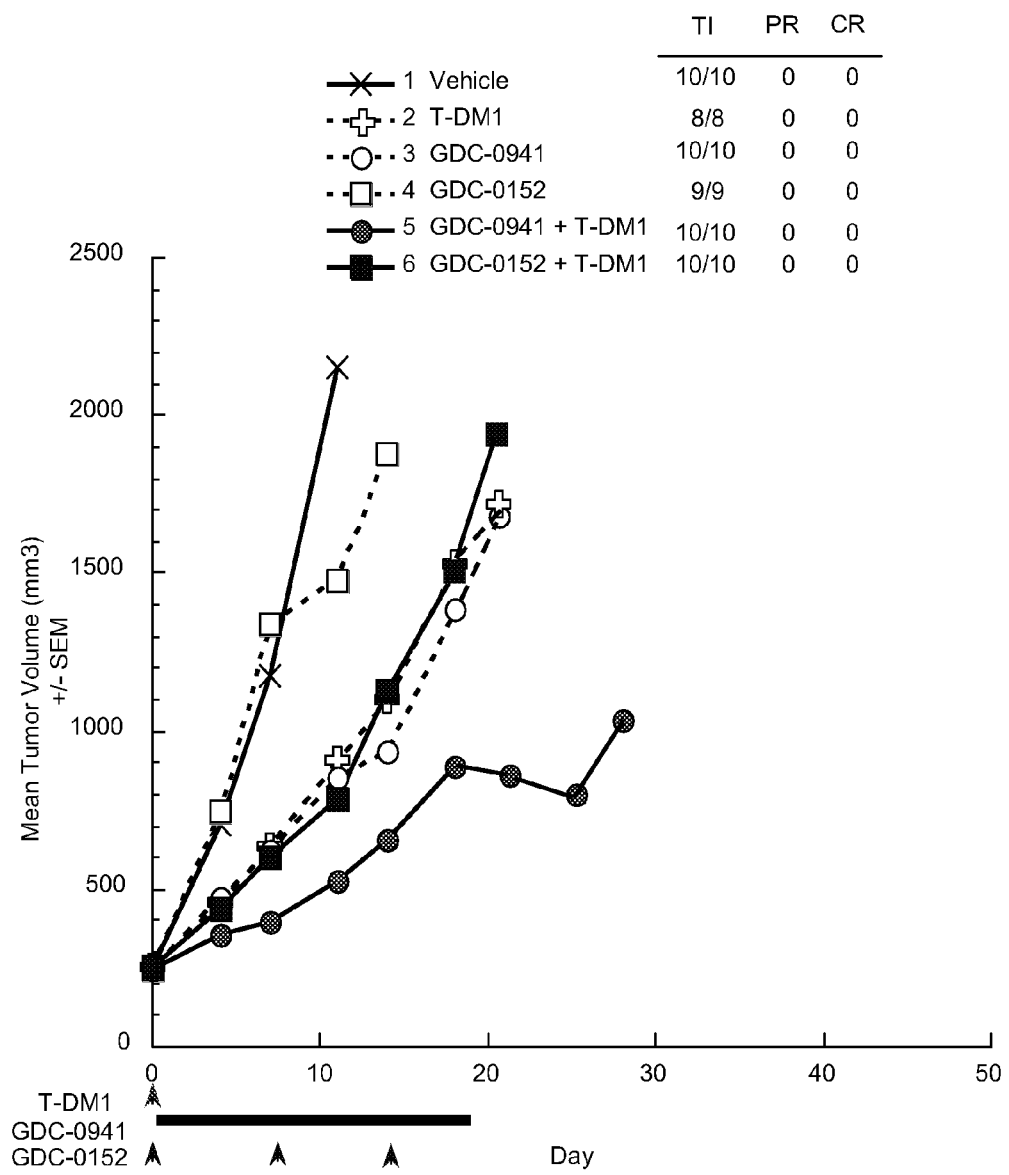
FIG. 35 shows a plot of the in vivo mean tumor volume change over time on MMTV-Her2 Fo5 transgenic mammary tumor inoculated into CRL nu/nu mice after dosing with: (1) Vehicle, po, qd×21 (2) T-DM1, 5 mg/kg, iv, qd×1, (3) GDC-0941, 100 mg/kg, po, qd×21, (4) GDC-0152, 50 mg/kg, po, qwk×3, (5) T-DM1, 5 mg/kg, iv, qd×1+GDC-0941, 100 mg/kg, po, qd×21, (6) T-DM1, 5 mg/kg, iv, qd×1+GDC-0152, 50 mg/kg, po, qwk×3

FIG. 35 shows a plot of the in vivo mean tumor volume change over time on MMTV-Her2 Fo5 transgenic mammary tumor inoculated into CRL nu/nu mice after dosing with: (1) Vehicle, po, qd×21 (2) T-DM1, 5 mg/kg, iv, q3wk, (3) GDC-0941, 100 mg/kg, po, bid×21, (4) GDC-0152, 50 mg/kg, po, qwk×2, (5) T-DM1, 5 mg/kg, iv, q3wk+GDC-0941, 100 mg/kg, po, bid×21, (6) T-DM1, 5 mg/kg, iv, q3wk+GDC-0152, 50 mg/kg, po, qwk×2. Treatment with T-DM1 and GDC-0941 results in enhanced anti-tumor activity compared to single agent treatment, while the combination of T-DM1 and GDC-0152 was not more efficacious than T-DM1 alone.

GDC-0152 is an inhibitor of caspases which are inhibitors of apoptosis proteins (Call et al (2008) The Lancet Oncology, 9(10):1002-1011; Deveraux et al (1999) J Clin Immunol 19:388-398).

Figure 36:
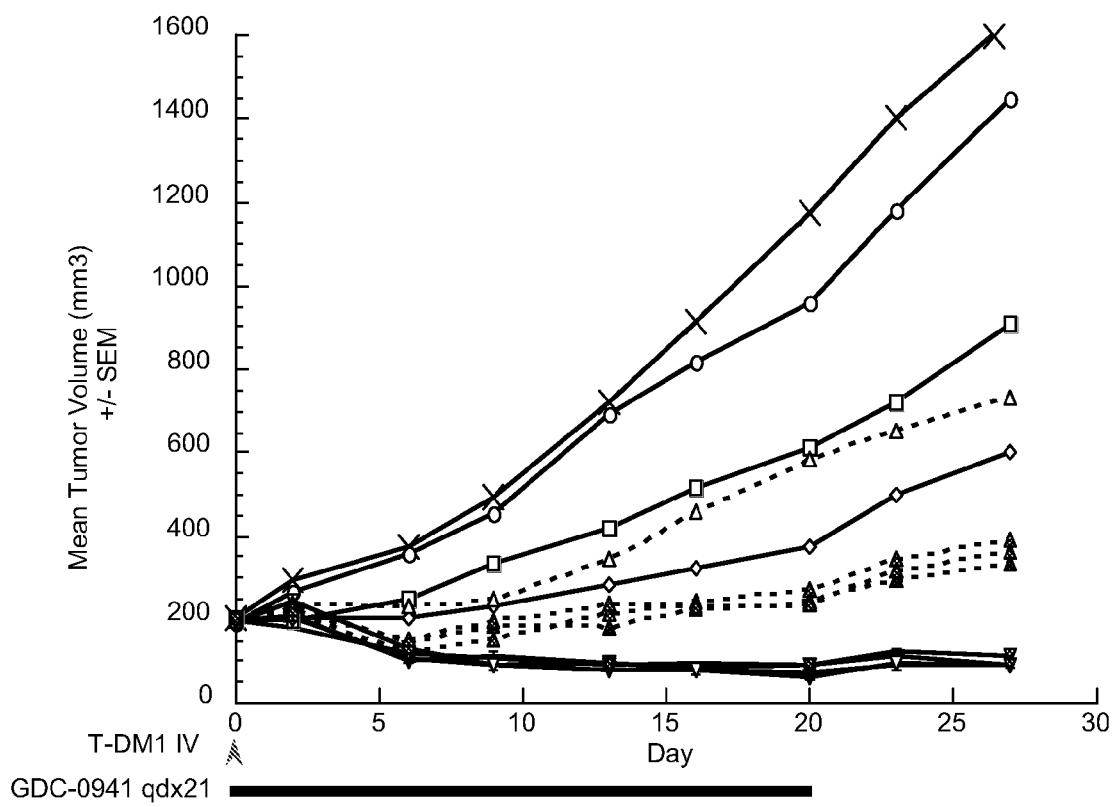
FIG. 36 shows a plot of the in vivo mean tumor volume change over time on MDA-MB-361.1 mammary tumor inoculated into CRL nu/nu mice after dosing with: (1) Vehicle, po, qd×21 (2) GDC-0941, 25 mg/kg, po, qd×21, (3) GDC-0941, 50 mg/kg, po, qd×21, (4) GDC-0941, 100 mg/kg, po, qd×21, (5) T-DM1, 3 mg/kg, iv, qd×1, (6) T-DM1, 10 mg/kg, iv, qd×1, (7) GDC-0941, 25 mg/kg, po, qd×21+T-DM1, 3 mg/kg, iv, qd×1, (8) GDC-0941, 50 mg/kg, po, qd×21+T-DM1, 3 mg/kg, iv, qd×1, (9) GDC-0941, 100 mg/kg, po, qd×21+T-DM1, 3 mg/kg, iv, qd×1, (10) GDC-0941, 25 mg/kg, po, qd×21+T-DM1, 10 mg/kg, iv, qd×1, (11) GDC-0941, 50 mg/kg, po, qd×21+T-DM1, 10 mg/kg, iv, qd×1, (12) GDC-0941, 100 mg/kg, po, qd×21+T-DM1, 10 mg/kg, iv, qd×1

FIG. 36 shows a plot of the in vivo mean tumor volume change over time on MDA-MB-361.1 mammary tumor inoculated into CRL nu/nu mice after dosing with: (1) Vehicle, po, qd×21, (2) GDC-0941, 25 mg/kg, po, qd×21, (3) GDC-0941, 50 mg/kg, po, qd×21, (4) GDC-0941, 100 mg/kg, po, qd×21, (5) T-DM1, 3 mg/kg, iv, q3wk, (6) T-DM1, 10 mg/kg, iv, q3wk, (7) GDC-0941, 25 mg/kg, po, qd×21+T-DM1, 3 mg/kg, iv, q3wk, (8) GDC-0941, 50 mg/kg, po, qd×21+T-DM1, 3 mg/kg, iv, q3wk, (9) GDC-0941, 100 mg/kg, po, qd×21+T-DM1, 3 mg/kg, iv, q3wk, (10) GDC-0941, 25 mg/kg, po, qd×21+T-DM1, 10 mg/kg, iv, q3wk, (11) GDC-0941, 50 mg/kg, po, qd×21+T-DM1, 10 mg/kg, iv, q3wk, (12) GDC-0941, 100 mg/kg, po, qd×21+T-DM1, 10 mg/kg, iv, q3wk.

Animals dosed with Vehicle (1) gave 0 partial responses (PR) and 0 complete response (CR). Animals dosed with GDC-0941 at 25 mg/kg alone (2) gave 0 PR and 0 CR. Animals dosed with GDC-0941 at 50 mg/kg alone (3) gave 1 PR and 0 CR. Animals dosed with GDC-0941 at 100 mg/kg alone (4) gave 0 PR and 0 CR. Animals dosed with T-DM1 at 3 mg/kg (5) alone gave 1 (PR) and 1 CR). Animals dosed with T-DM1 at 10 mg/kg (6) alone gave 8 (PR) and 1 CR). Animals dosed with the combination of T-DM1 at 3 mg/kg and GDC-0941 at 25 mg/kg (7) gave 5 PR and 0 CR. Animals dosed with the combination of T-DM1 at 3 mg/kg and GDC-0941 at 50 mg/kg (8) gave 3 PR and 0 CR. Animals dosed with the combination of T-DM1 at 3 mg/kg and GDC-0941 at 100 mg/kg (9) gave 3 PR and 1 CR. Animals dosed with the combination of T-DM1 at 10 mg/kg and GDC-0941 at 50 mg/kg (10) gave 9 PR and 0 CR. Animals dosed with the combination of T-DM1 at 10 mg/kg and GDC-0941 at 50 mg/kg (11) gave 7 PR and 2 CR. Animals dosed with the combination of T-DM1 at 10 mg/kg and GDC-0941 at 100 mg/kg (12) gave 9 PR and 1 CR.

Figure 37:
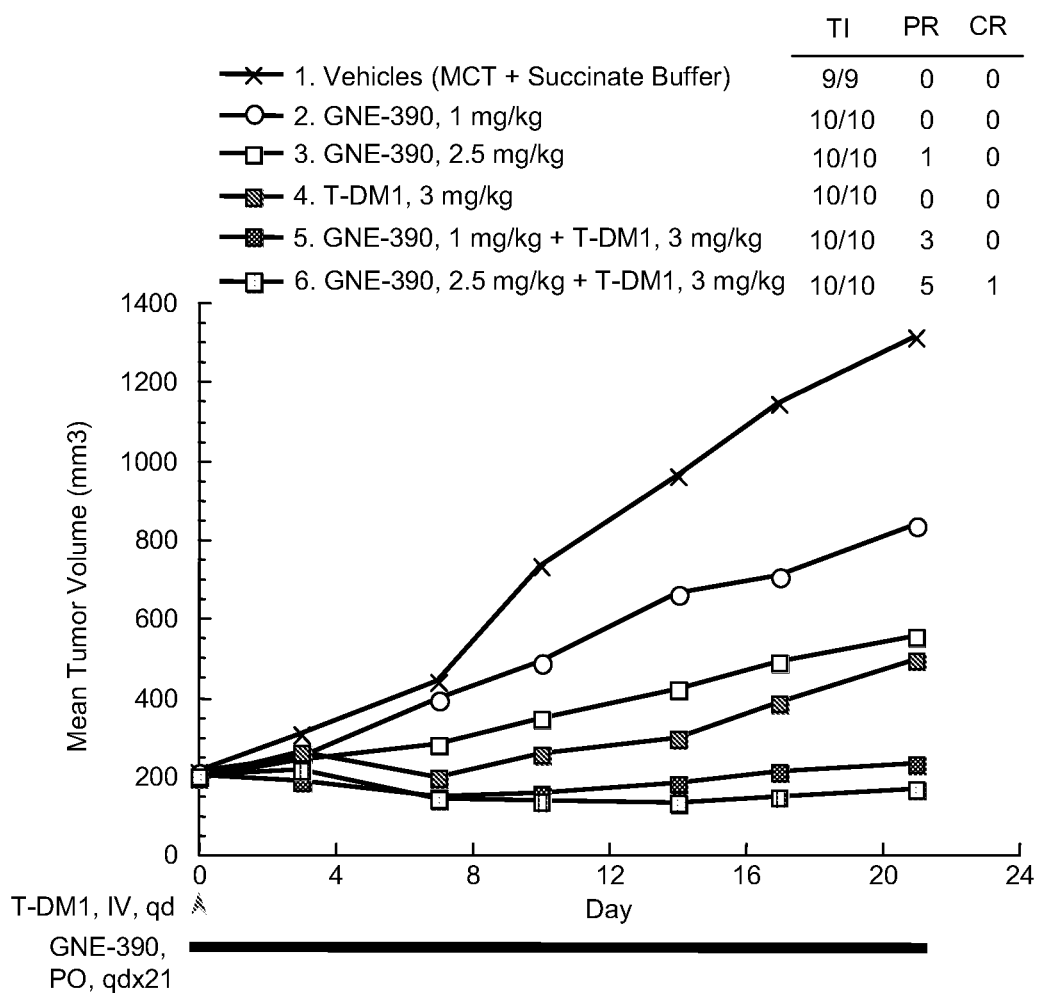
FIG. 37 shows a plot of the in vivo mean tumor volume change over time on MDA-MB-361.1 mammary tumor inoculated into CRL nu/nu mice after dosing with: (1) Vehicles [MCT (0.5% methylcellulose/0.2% TWEEN 80™)+succinate buffer (100 mM sodium succinate, 100 mg/ml trehalose, 0.1% TWEEN 80, pH 5.0)], po+IV, qd×21 and qd (2) GNE-390, 1.0 mg/kg, po, qd×21, (3) GNE-390, 2.5 mg/kg, po, qd×21, (4) T-DM1, 3 mg/kg, iv, qd, (5) GNE-390, 1.0 mg/kg, po, qd×21+T-DM1, 3 mg/kg, iv, qd, (6) GNE-390, 2.5 mg/kg, po, qd×21+T-DM1, 3 mg/kg, iv, qd

FIG. 37 shows a plot of the in vivo mean tumor volume change over time on MDA-MB-361.1 mammary tumor inoculated into CRL nu/nu mice after dosing with: (1) Vehicles [MCT (0.5% methylcellulose/0.2% TWEEN 80)+ succinate buffer (100 mM sodium succinate, 100 mg/ml trehalose, 0.1% TWEEN 80, pH 5.0)], po+IV, qd×21 and qd (2) GNE-390, 1.0 mg/kg, po, qd×21, (3) GNE-390, 2.5 mg/kg, po, qd×21, (4) T-DM1, 3 mg/kg, iv, qd, (5) GNE-390, 1.0 mg/kg, po, qd×21+T-DM1, 3 mg/kg, iv, qd, (6) GNE-390, 2.5 mg/kg, po, qd×21+T-DM1, 3 mg/kg, iv, qd Animals dosed with Vehicle (1) gave 0 partial responses (PR) and 0 complete response (CR). Animals dosed with GNE-390 at 1.0 mg/kg alone (2) gave 0 PR and 0 CR. Animals dosed with GNE-390 at 2.5 mg/kg alone (3) gave 1 PR and 0 CR. Animals dosed with T-DM1 at 3 mg/kg (5) alone gave 1 (PR) and 1 CR). Animals dosed with T-DM1 at 3 mg/kg (4) alone gave 0 PR and 0 CR. Animals dosed with the combination of T-DM1 at 3 mg/kg and GNE-390 at 25 mg/kg (5) gave 3 PR and 0 CR. Animals dosed with the combination of T-DM1 at 3 mg/kg and GNE-390 at 2.5 mg/kg (6) gave 5 PR and 1 CR. Combination of GNE-390 with T-DM1 significantly increased the number of partial and complete anti-tumor responses when compared to GNE-390 or T-DM1 alone in the MDA-MB-361.1 breast cancer xenograft model.

Pharmaceutical Compositions

Pharmaceutical compositions or formulations of the present invention include combinations of trastuzumab- MCC-DM1, a chemotherapeutic agent, and one or more pharmaceutically acceptable carrier, glidant, diluent, or excipient.

Trastuzumab-MCC-DM1 and chemotherapeutic agents of the present invention may exist in unsolvated as well as solvated forms with pharmaceutically acceptable solvents such as water, ethanol, and the like, and it is intended that the invention embrace both solvated and unsolvated forms.

Trastuzumab-MCC-DM1 and chemotherapeutic agents of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Pharmaceutical compositions encompass both the bulk composition and individual dosage units comprised of more than one (e.g., two) pharmaceutically active agents including trastuzumab-MCC-DM1 and a chemotherapeutic agent selected from the lists of the additional agents described herein, along with any pharmaceutically inactive excipients, diluents, carriers, or glidants. The bulk composition and each individual dosage unit can contain fixed amounts of the aforesaid pharmaceutically active agents. The bulk composition is material that has not yet been formed into individual dosage units. An illustrative dosage unit is an oral dosage unit such as tablets, pills, capsules, and the like. Similarly, the herein-described method of treating a patient by administering a pharmaceutical composition of the present invention is also intended to encompass the administration of the bulk composition and individual dosage units.

Pharmaceutical compositions also embrace isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I, and $^{125}$I. Certain isotopically-labeled compounds of the present invention (e.g., those labeled with $^3$H and $^{14}$C) are useful in compound and/or substrate tissue distribution assays. Tritiated ($^3$H) and carbon-14 ($^{14}$C) isotopes are useful for their ease of preparation and detectability. Further, substitution with heavier isotopes such as deuterium ($^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C and $^{18}$F are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Trastuzumab-MCC-DM1 and chemotherapeutic agents may be formulated in accordance with standard pharmaceutical practice for use in a therapeutic combination for therapeutic treatment (including prophylactic treatment) of hyperproliferative disorders in mammals including humans. The invention provides a pharmaceutical composition comprising trastuzumab-MCC-DM1 in association with one or more pharmaceutically acceptable carrier, glidant, diluent, or excipient.

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration with pharmaceutically acceptable diluents, carriers, excipients or stabilizers (Remington's Pharmaceutical Sciences (1995) 18th edition, Mack Publ. Co., Easton, Pa.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8.

The pharmaceutical formulation is preferably sterile. In particular, formulations to be used for in vivo administration must be sterile. Such sterilization is readily accomplished by filtration through sterile filtration membranes.

The pharmaceutical formulation ordinarily can be stored as a solid composition, a lyophilized formulation or as an aqueous solution.

The pharmaceutical formulations of the invention will be dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

As a general proposition, the initial pharmaceutically effective amount of trastuzumab-MCC-DM1 administered per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl, ethanol, or benzylalcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, including Tween 80, PLURONICS™ or polyethylene glycol (PEG), including PEG400. The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 18th edition, (1995) Mack Publ. Co., Easton, Pa.

The pharmaceutical formulations include those suitable for the administration routes detailed herein. The formulations may conveniently be presented in unit dosage form and may be prepared by any of the methods well known in the art of pharmacy. Techniques and formulations generally are found in Remington's Pharmaceutical Sciences $18^{th}$ Ed. (1995) Mack Publishing Co., Easton, Pa. Such methods include the step of bringing into association the active ingredient with the carrier which constitutes one or more accessory ingredients.

In general the formulations are prepared by uniformly and intimately bringing into association the active ingredient with liquid carriers or finely divided solid carriers or both, and then, if necessary, shaping the product.

Formulations of a chemotherapeutic agent suitable for oral administration may be prepared as discrete units such as pills, hard or soft e.g., gelatin capsules, cachets, troches, lozenges, aqueous or oil suspensions, dispersible powders or granules, emulsions, syrups or elixirs each containing a predetermined amount of a compound of trastuzumab-MCC-DM1 and/or a chemotherapeutic agent. Such formulations may be prepared according to any method known to the art for the manufacture of pharmaceutical compositions and such compositions may contain one or more agents including sweetening agents, flavoring agents, coloring agents and preserving agents, in order to provide a palatable preparation. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablet excipients of a pharmaceutical formulation of the invention may include: Filler (or diluent) to increase the bulk volume of the powdered drug making up the tablet; Disintegrants to encourage the tablet to break down into small fragments, ideally individual drug particles, when it is ingested and promote the rapid dissolution and absorption of drug; Binder to ensure that granules and tablets can be formed with the required mechanical strength and hold a tablet together after it has been compressed, preventing it from breaking down into its component powders during packaging, shipping and routine handling; Glidant to improve the flowability of the powder making up the tablet during production; Lubricant to ensure that the tableting powder does not adhere to the equipment used to press the tablet during manufacture. They improve the flow of the powder mixes through the presses and minimize friction and breakage as the finished tablets are ejected from the equipment; Antiadherent with function similar to that of the glidant, reducing adhesion between the powder making up the tablet and the machine that is used to punch out the shape of the tablet during manufacture; Flavor incorporated into tablets to give them a more pleasant taste or to mask an unpleasant one, and Colorant to aid identification and patient compliance.

Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner, including a mixture of at least one emulsifier with a fat or an oil, or with both a fat and an oil. Preferably, a hydrophilic emulsifier is included together with a lipophilic emulsifier which acts as a stabilizer. Together, the emulsifier(s) with or without stabilizer(s) make up an emulsifying wax, and the wax together with the oil and fat comprise an emulsifying ointment base which forms the oily dispersed phase of cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of the pharmaceutical formulations of the invention contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may be a solution or a suspension in a non-toxic parenterally acceptable diluent or solvent, such as a solution in 1,3-butanediol or prepared from a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

Trastuzumab-MCC-DM1 may be employed in combination with other chemotherapeutic agents for the treatment of a hyperproliferative disease or disorder, including tumors, cancers, and neoplastic tissue, along with pre-malignant and non-neoplastic or non-malignant hyperproliferative disorders. In certain embodiments, trastuzumab-MCC-DM1 is combined in a pharmaceutical combination formulation, or dosing regimen as combination therapy, with a second compound that has anti-hyperproliferative properties or that is useful for treating the hyperproliferative disorder. The second compound of the pharmaceutical combination formulation or dosing regimen preferably has complementary activities to trastuzumab-MCC-DM1, and such that they do not adversely affect each other. Such compounds are suitably present in combination in amounts that are effective for the purpose intended. In one embodiment, a composition of this invention comprises trastuzumab-MCC-DM1 in combination with a chemotherapeutic agent such as described herein. Examples 4 and 5 are clinical protocols for T-DM1+pertuzumab, and T-DM1+GDC-0941, respectively.

Therapeutic combinations of the invention include a formulation, dosing regimen, or other course of treatment comprising the administration of trastuzumab-MCC-DM1, and a chemotherapeutic agent selected from a HER2 dimerization inhibitor antibody, an anti-VEGF antibody, 5-FU, carboplatin, lapatinib, ABT-869, and docetaxel, as a combined preparation for separate, simultaneous or sequential use in the treatment of a hyperproliferative disorder.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

In a particular embodiment of anti-cancer therapy, trastuzumab-MCC-DM1 may be combined with a chemotherapeutic agent, including hormonal or antibody agents such as those described herein, as well as combined with surgical therapy and radiotherapy. The amounts of trastuzumab-MCC-DM1 and the other pharmaceutically active chemotherapeutic agent(s) and the relative timings of administration will be selected in order to achieve the desired combined therapeutic effect.

Administration of Pharmaceutical Compositions

The compounds of the invention may be administered by any route appropriate to the condition to be treated. Suitable routes include oral, parenteral (including subcutaneous, intramuscular, intravenous, intraarterial, inhalation, intradermal, intrathecal, epidural, and infusion techniques), transdermal, rectal, nasal, topical (including buccal and sublingual), vaginal, intraperitoneal, intrapulmonary and intranasal. Topical administration can also involve the use of transdermal administration such as transdermal patches or iontophoresis devices. Formulation of drugs is discussed in Remington's Pharmaceutical Sciences, 18$^{th}$ Ed., (1995) Mack Publishing Co., Easton, Pa. Other examples of drug formulations can be found in Liberman, H. A. and Lachman, L., Eds., Pharmaceutical Dosage Forms, Marcel Decker, Vol 3, 2$^{nd}$ Ed., New York, N.Y. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier, glidant, or excipient. Where the compound is administered parenterally, it may be formulated with a pharmaceutically acceptable parenteral vehicle or diluent, and in a unit dosage injectable form, as detailed below.

A dose of trastuzumab-MCC-DM1 to treat human patients may range from about 100 mg to about 500 mg. The dose of trastuzumab-MCC-DM1 may be administered once every six weeks, once every three weeks, weekly, or more frequently, depending on the pharmacokinetic (PK) and pharmacodynamic (PD) properties, including absorption, distribution, metabolism, and excretion. A dose of the chemotherapeutic agent, used in combination with trastuzumab-MCC-DM1, may range from about 10 mg to about 1000 mg. The chemotherapeutic agent may be administered once every six weeks, once every three weeks, weekly, or more frequently, such as once or twice per day. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment

Therapeutic combinations of: (1) trastuzumab-MCC-DM1 and (2) a chemotherapeutic agent are useful for treating diseases, conditions and/or disorders including, but not limited to, those characterized by activation of the HER2 pathway. Accordingly, another aspect of this invention includes methods of treating diseases or conditions that can be treated by targeting HER2 or the VEGFR receptor 1. Therapeutic combinations of: (1) trastuzumab-MCC-DM1 and (2) a chemotherapeutic agent may be employed for the treatment of a hyperproliferative disease or disorder, including tumors, cancers, and neoplastic tissue, along with pre-malignant and non-neoplastic or non-malignant hyperproliferative disorders.

Cancers which can be treated according to the methods of this invention include, but are not limited to, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

Another aspect of this invention provides a pharmaceutical composition or therapeutic combination for use in the treatment of the diseases or conditions described herein in a mammal, for example, a human, suffering from such disease or condition. Also provided is the use of a pharmaceutical composition in the preparation of a medicament for the treatment of the diseases and conditions described herein in a warm-blooded animal, such as a mammal, for example a human, suffering from such disorder.

Articles of Manufacture

In another embodiment of the invention, an article of manufacture, or "kit", containing trastuzumab-MCC-DM1 useful for the treatment of the diseases and disorders described above is provided. In one embodiment, the kit comprises a container comprising trastuzumab-MCC-DM1. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold trastuzumab-MCC-DM1 or a formulation thereof which is effective for treating the condition and may have a sterile access port (for example, the container may be an intravenous solution bag or a vial having a stopper pierceable by a hypodermic injection needle). At least one active agent in the composition is trastuzumab-MCC-DM1. The label or package insert indicates that the composition is used for treating the condition of choice, such as cancer. In one embodiment, the label or package inserts indicates that the composition comprising trastuzumab-MCC-DM1 can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of trastuzumab-MCC-DM1 and, if present, the second pharmaceutical formulation. For example, if the kit comprises a first composition comprising trastuzumab-MCC-DM1 and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of trastuzumab-MCC-DM1, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with trastuzumab-MCC-DM1 contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Where the kit comprises a composition of trastuzumab-MCC-DM1 and a second therapeutic agent, i.e. the chemotherapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

EXAMPLES

In order to illustrate the invention, the following examples are included. However, it is to be understood that these examples do not limit the invention and are only meant to suggest a method of practicing the invention.

Example 1

Preparation of Trastuzumab-MCC-DM1

Trastuzumab was purified from HERCEPTIN® by buffer-exchange at 20 mg/mL in 50 mM potassium phosphate/50 mM sodium chloride/2 mM EDTA, pH 6.5 and treated with 7.5 to 10 molar equivalents of succinimidyl 4-(N-maleimidomethyl) cyclohexane-1-carboxylate (SMCC, Pierce Biotechnology, Inc), 20 mM in DMSO or DMA (dimethylacetamide), 6.7 mg/mL (US 2005/0169933; US 2005/0276812). After stirring for 2 to 4 hours under argon at ambient temperature, the reaction mixture was filtered through a Sephadex G25 column equilibrated with 50 mM potassium phosphate/50 mM sodium chloride/2 mM EDTA, pH 6.5. Alternatively, the reaction mixture was gel filtered with 30 mM citrate and 150 mM sodium chloride at pH 6. Antibody containing fractions were pooled and assayed. Recovery of trastuzumab-SMCC was 88%.

The drug-linker intermediate, trastuzumab-MCC from above, was diluted with 50 mM potassium phosphate/50 mM sodium chloride/2 mM EDTA, pH 6.5, to a final concentration of 10 mg/ml, and reacted with a 10 mM solution of DM1 (1.7 equivalents assuming 5 SMCC/trastuzumab, 7.37 mg/ml) in dimethylacetamide. DM1 may be prepared from ansamitocin fermentation products (U.S. Pat. No. 6,790,954; U.S. Pat. No. 7,432,088) and derivatized for conjugation (U.S. Pat. No. 6,333,410; RE 39151). The reaction was stirred at ambient temperature under argon for 4 to about 16 hours. The conjugation reaction mixture was filtered through a Sephadex G25 gel filtration column (1.5×4.9 cm) with 1×PBS at pH 6.5. Alternatively, the reaction mixture was gel filtered with 10 mM succinate and 150 mM sodium chloride at pH 5. The DM1/trastuzumab ratio (p) was 3.1, as measured by the absorbance at 252 nm and at 280 nm. The drug to antibody ratio (p) may also be measured by mass spectrometry. Conjugation may also be monitored by SDS polyacrylamide gel electrophoresis. Aggregation may be assessed by laser light scattering analysis.

Alternatively, trastuzumab-MCC-DM1 may be prepared by forming an MCC-DM1 linker-drug reagent and then reacting with trastuzumab.

Typically a conjugation reaction of trastuzumab-MCC with DM1 results in a heterogeneous mixture comprising antibodies different numbers of attached, conjugated DM1 drugs, i.e. drug loading where p is a distribution from 1 to about 8. An additional dimension of heterogeneity exists with different attachment sites of SMCC to trastuzumab where many different nucleophiles on trastuzumab, e.g. terminal lysine amino groups, can react with SMCC. Thus, trastuzumab-MCC-DM1 includes isolated, purified species molecules as well as mixtures of average drug loading from 1 to 8 and where MCC-DM1 is attached through any site of the trastuzumab antibody.

The average number of DM1 drug moieties per trastuzumab antibody in preparations of trastuzumab-MCC-DM1 from conjugation reactions may be characterized by conventional means such as mass spectroscopy, ELISA assay, electrophoresis, and HPLC. The quantitative distribution of trastuzumab-MCC-DM1 in terms of p may also be determined. By ELISA, the averaged value of p in a particular preparation of ADC may be determined (Hamblett et al (2004) Clinical Cancer Res. 10:7063-7070; Sanderson et al (2005) Clinical Cancer Res. 11:843-852). However, the distribution of p (drug) values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues. In some instances, separation, purification, and characterization of homogeneous trastuzumab-MCC-DM1 where p is a certain value from trastuzumab-MCC-DM1 with other drug loadings may be achieved by means such as reverse phase HPLC or electrophoresis.

Example 2

In Vitro Cell Proliferation Assay

Efficacy of the combinations of the invention was measured by a cell proliferation assay employing the following protocol (Promega Corp. Technical Bulletin TB288; Mendoza et al (2002) Cancer Res. 62:5485-5488). The Cell-Titer Glo assay reagents and protocol are commercially available (Promega). The assay assesses the ability of compounds to get into cells and affect cell proliferation. The assay principle is the determination of the number of viable cells present by quantitating the cellular ATP. Cell-Titer Glo is the reagent used for this quantitation. It is a homogenous assay where addition of the Cell-Titer Glo results in cell lysis and generation of a luminescent signal through the luciferase reaction. The luminescent signal is proportional to the amount of ATP present.

DMSO and Media Plates: 96-well conical bottom polypropylene plates from Nunc (cat. #249946)

Cell Plates: 384-well black, clear bottom (microclear), TC plates with lid from Falcon (353962)

Cell Culture Medium: RPMI or DMEM high glucose; Ham's F-12 (50:50), 10% Fetal Bovine Serum, 2 mM L-Glutamine Cell Titer-Glo: Promega (cat. #G7572)

Procedure:

Day 1—Seed Cell Plates, Harvest cells, Seed cells at 1000-2000 cells per 54 µl per well into 384 well Cell Plates for 3 days assay. Incubate overnight (approx. 16 hr) at 37 C, 5% CO2.

Day 2—Add Drug to Cells, Compound Dilution, DMSO Plates (serial 1:2 for 9 points). Add 20 ul compounds (10 mM stock solution for small molecule drugs) in the 2nd column of 96 well plate. Perform serial 1:2 across the plate (10 µl+10 µl 100% DMSO) for a total of 9 points using Precision Media Plates (1:50 dilution). Add 147 µl of Media into all wells of separate 96-well media plate. Transfer 3 µl of DMSO+compound from each well in the DMSO Plate to each corresponding well on Media Plate using Rapidplate. For 2 drug combo studies, transfer one drug 1.5 µl of DMSO+compound from each well in the DMSO Plate to each corresponding well on Media Plate using Rapidplate. Then, transfer another drug 1.5 ul to the medium plate.

Drug Addition to Cells, Cell Plate (1:10 dilution), Add 6 µl of media+compound directly to cells (54 µl of media on the cells already). Incubate 3 days at 37 C, 5% CO2 in an incubator that will not be opened often.

Day 5—Develop Plates, Thaw Cell Titer Glo Buffer at room temperature. Remove Cell Plates from 37° C. and equilibrate to room temperature. for about 30 minutes. Add Cell Titer Glo Buffer to Cell Titer Glo Substrate (bottle to bottle). Add 30 µA Cell Titer Glo Reagent to each well of cells. Place on plate shaker for about 30 minutes. Read luminescence on PerkinElmer Envision (0.1 second per well) or Analyst HT Plate Reader (half second per well).

Cell viability assays and combination assays: Cells were seeded at 1000-2000 cells/well in 384-well plates for 16 h. On day two, nine serial 1:2 compound dilutions were made in DMSO in a 96 well plate. The compounds were further diluted into growth media using a Rapidplate robot (Zymark Corp., Hopkinton, Mass.). The diluted compounds were then added to quadruplicate wells in 384-well cell plates and incubated at 37 C and 5% CO2. After 4 days, relative numbers of viable cells were measured by luminescence using Cell-Titer Glo (Promega) according to the manufacturer's instructions and read on an Envision or a Wallac Multilabel Reader (PerkinElmer, Foster City). EC50 values were calculated using Kaleidagraph 4.0 (Synergy Software) or Prism 4.0 software (GraphPad, San Diego). Drugs in combination assays were dosed starting at 8×EC50 concentrations. In cases where the EC50 of the drug was >2.5 µM, the highest concentration used was 10 µM. Trastuzumab-MCC-DM1 and chemotherapeutic agents were added simultaneously or separated by 4 hours (one before the other) in all assays.

An additional exemplary in vitro cell proliferation assay includes the following steps:

1. An aliquot of 100 µl of cell culture containing about $10^4$ cells (see FIG. 1 for cell lines and tumor type) in medium was deposited in each well of a 384-well, opaque-walled plate.

2. Control wells were prepared containing medium and without cells.

3. The compound was added to the experimental wells and incubated for 3-5 days.

4. The plates were equilibrated to room temperature for approximately 30 minutes.

5. A volume of CellTiter-Glo Reagent equal to the volume of cell culture medium present in each well was added.

6. The contents were mixed for 2 minutes on an orbital shaker to induce cell lysis.

7. The plate was incubated at room temperature for 10 minutes to stabilize the luminescence signal.

8. Luminescence was recorded and reported in graphs as RLU=relative luminescence units.

Alternatively, cells were seeded at optimal density in a 96 well plate and incubated for 4 days in the presence of test compound. Alamar Blue™ was subsequently added to the assay medium, and cells were incubated for 6 h before reading at 544 nm excitation, 590 nm emission. $EC_{50}$ values were calculated using a sigmoidal dose response curve fit.

Example 3

In Vivo Tumor Xenograft

Animals suitable for transgenic experiments can be obtained from standard commercial sources. Groups of female CB-17 SCID beige mice (Charles River Laboratory) were implanted with 3 million KPL-4 (Her2 overexpressing) breast cancer cells with matrigel in the mammary fat pad. Groups of female athymic nude mice (Charles River Laboratory or Harlan) were implanted with 2×2 mm3 fragments of MMTV-Her2 Fo5 transgenic breast tumors in the mammary fat pad. Mouse xenografts were dosed at day 0 with drug, drug combination, or vehicle according to the schedule specified for each tumor model. 5-FU, gemcitabine, carboplatin and B20-4.1 were administered intraperitoneal, pertuzumab was given either intravenously or intraperitoneal as indicated, trastuzumab-MCC-DM1 and docetaxel were administered intravenously, lapatinib, GDC-0941 and ABT-869 were given periorally by gavage. Tumor sizes were recorded twice weekly over the course of the study. Mouse body weights were also recorded twice weekly, and the mice were observed regularly. Tumor volume was measured in two dimensions (length and width) using Ultra Cal IV calipers (Model 54-10-111; Fred V. Fowler Co., Inc.; Newton, Mass.) and analyzed using Excel v.11.2 (Microsoft Corporation; Redmond, Wash.). Tumor inhibition graphs were plotted using KaleidaGraph, Version 3.6 (Synergy Software; Reading, Pa.). The tumor volume was calculated with formula: Tumor size $(mm^3)$=(longer measurement×shorter measurement)×0.5

Animal body weights were measured using an Adventurera Pro AV812 scale (Ohaus Corporation; Pine Brook, N.J.). Graphs were generated using KaleidaGraph Version 3.6. Percent weight change was calculated using formula: Group percent weight change=(1−(initial weight/new weight))×100.

Mice whose tumor volume exceeded 2000 mm³ or whose body weight loss was more than 20% of their starting weight were promptly euthanized according to regulatory guidance. The percent tumor growth delay (% TGD) at the end of study (EOS) was calculated using formula: % TGD=100× (Median time to endpoint for the treatment group−median time to endpoint for the control group)/Median time to endpoint for the control group.

Tumor incidence (TI) was determined based on the number of measurable tumors remaining in each group at the end of the study. A partial response (PR) was defined as more than 50% but less than 100% reduction in tumor volume, compared with the starting tumor volume, observed for three consecutive measurements. A complete response (CR) was defined as a 100% reduction in tumor volume, compared with the initial tumor volume, observed for three consecutive measurements. Data were analyzed and p-values were determined using the Dunnett's t-test with JMP statistical software, version 5.1.2 (SAS Institute; Cary, N.C.). Individual tumor volumes at end of study and mean tumor volume±SEM values were calculated using JMP statistical software, version 5.1.2. Body weight data were graphed based on the mean percentage of change from initial body weights±SEM.

Example 4

Clinical Study of Trastuzumab-MCC-DM1 (T-DM1) in Combination with Pertuzumab

A Phase 1b/II, open-label study of the safety, tolerability, and efficacy of trastuzumab-MCC-DM1 (T-DM1) in combination with pertuzumab administered intravenously to patients with HER2-positive locally advanced or metastatic breast cancer who have progressed while receiving prior therapy was designed to characterize the safety and tolerability of the combination. The combination is administered every 3 weeks to patients with HER2-positive locally advanced or metastatic breast cancer who have previously received trastuzumab in any line of therapy, have received chemotherapy combined with HER2-targeted therapy for advanced disease, or have progressed while receiving their most recent therapy. Another objective is to evaluate the pharmacokinetics of T-DM1 when the combination of T-DM1 and pertuzumab is administered on this schedule. Another objective is to make a preliminary assessment of the efficacy of the combination of T-DM1 and pertuzumab administered on this schedule, as measured by objective response rate based on investigator assessment using modified Response Evaluation Criteria in Solid Tumors (RECIST), Version 1.0. Secondary objectives for this study are as follows: (1) To estimate the progression-free survival (PFS) of patients who receive the combination of T-DM1 and pertuzumab administered on this schedule; (2) To assess the duration of response of the combination of T-DM1 and pertuzumab administered on this schedule; and (3) To assess the development of anti-therapeutic antibodies to T-DM1.

T-DM1 will be administered by intravenous (IV) infusion in combination with pertuzumab, also administered by intravenous (IV) infusion, in patients with HER2-positive locally advanced or metastatic breast cancer that have previously received trastuzumab and have progressed following or while receiving their last therapy. Patients will receive a combination of T-DM1 and pertuzumab, in repeated cycles, at a minimum interval of 3 weeks.

Patients at a given dose level will be observed for DLT (Dose-Limiting Toxicity) during the DLT Observation Period (defined as 21 days from the time of the first dose of T-DM1) after receiving their first doses of study drugs prior to treatment of any patient at a higher dose level. If no DLTs are observed in these patients during the DLT Observation Period, dose escalation to the next dose level may proceed.

A DLT is defined as any of the following treatment-related toxicities occurring within the DLT Observation Period: (1) Grade ≥3 non-hematologic adverse event that is not due to disease progression or another clearly identifiable cause, except for alopecia of any grade; (2) Grade 3 diarrhea that responds to standard of care therapy: (3) Grade 3 nausea or vomiting in the absence of premedication that responds to standard of care therapy; (4) Grade ≥3 elevation of serum bilirubin, hepatic transaminases (ALT or AST), or alkaline phosphatase (ALP) lasting 72 hours, with the exception of patients with Grade 2 hepatic transaminase or ALP levels at baseline, (≤5 the upper limit of normal [ULN]) as a result of liver or bone metastases. A hepatic transaminase or ALP level ≥10 ULN will be considered a DLT; (5) Grade ≥4 thrombocytopenia lasting 24 hours; (6) Grade ≥4 neutropenia (absolute neutrophil count <500/cells/mm³) lasting 4 days or accompanied by a fever (oral or tympanic temperature 100.4° F. or 38° C.); (7) Any subjectively intolerable toxicity felt by the investigator to be related to either test compound; (8) Any treatment-related toxicity prohibiting the start of the second cycle of treatment.

Once a decision has been made to proceed to the next highest dose level, an intra-patient dose escalation will also be allowed; patients enrolled in the study will initially receive a reduced dose of T-DM1 (3.0 mg/kg) along with full-dose pertuzumab. These patients will be allowed to escalate to full doses of both drugs for subsequent cycles once their cohort has cleared the DLT Observation Period. However, the safety of the 3.6 mg/kg dose level will be based on the assessment of DLT. Patients (including those who are enrolled in the study during the dose-escalation phase of the study) will be considered evaluable for efficacy if they remain on study through the first follow-up tumor assessment. Echocardiogram (ECHO) or multigated acquisition (MUGA) scans should be performed at the end of Cycle 1, and then every three cycles throughout the treatment period.

T-DM1 Formulation

T-DM1 may be provided as a single-use lyophilized formulation in a 20-mL Type I USP/European Pharmacopeia glass vial fitted with a 20-mm fluoro resin-laminated stopper and aluminum seal with a dark gray flip-off plastic cap. Following reconstitution with 8.0 mL Sterile Water for Injection (SWFI), the resulting product contains 20 mg/mL T-DM1 in 10 mM sodium succinate, pH 5.0, 6% (w/v) sucrose, and 0.02% (w/v) polysorbate 20. Each 20-mL vial contains approximately 172 mg T-DM1 to allow delivery of 160 mg T-DM1. The indicated volume of T-DM1 solution is removed from the vial(s) and added to the IV bag. Reconstituted T-DM1 is diluted into PVC or latex-free PVC-free polyolefin bags (PO) containing 0.45% or 0.9% Sodium Chloride Injection (minimum volume of 250 mL). The use of PVC or PO bags containing 0.45% Sodium Chloride is preferred. In cases wherein PVC or PO bags containing 0.9% Sodium Chloride are used, the use of 0.22 µm in-line filters is recommended. The bag is gently inverted to mix the solution. The solution of T-DM1 for infusion diluted in polyvinyl chloride (PVC) or latex-free PVC-free polyolefin (PO) bags containing 0.9% or 0.45% Sodium Chloride Injection, USP, may be stored at 2° C.-8° C. (36° F.-46° F.) for a short period of time.

Pertuzumab Formulation

Pertuzumab is provided as a single-use formulation containing 30 mg/mL pertuzumab formulated in 20 mM L-histidine (pH 6.0), 120 mM sucrose, and 0.02% polysorbate 20. Each 20-cc vial contains approximately 420 mg of pertuzumab (14.0 mL/vial). The indicated volume of pertuzumab solution is withdrawn from vials and added to a 250-cc IV bag of 0.9% sodium chloride solution for injection. The bag is gently inverted the bag to mix the solution, and visually inspected for particulates and discoloration prior to administration. The solution of pertuzumab for infusion diluted in polyethylene or non-PVC polyolefin bags containing 0.9% sodium chloride solution may be stored at 2° C.-8° C. (36° F.-46° F.) for a short period of time.

Safety Outcome Measures

The safety and tolerability of T-DM1 and pertuzumab will be assessed using the following primary safety outcome measures: (1) Incidence, nature, and severity of adverse events; (2) Adverse events or changes in physical findings and clinical laboratory results during and following study drug administration that result in dose modification, dose delay, or discontinuation of T-DM1 and/or pertuzumab; and (3) Change in cardiac function (i.e., left ventricular ejection fraction [LVEF], segmental wall abnormalities), including ECHO or MUGA scans Pharmacokinetic and Pharmacodynamic Outcome Measures The following pharmacokinetic parameters of T-DM1 and pertuzumab will be determined in all patients who receive study treatment using either non-compartmental and/or population methods, when appropriate, as data allow: (1) Serum concentrations of T-DM1 (conjugate), total trastuzumab (free and conjugated to DM1); (2) Plasma concentrations of free DM1; (3) Total exposure (area under the concentration-time curve [AUC]); (4) Maximum serum concentration (Cmax); (5) Minimum concentration (Cmin); (6) Clearance; (7) Volume of distribution; (8) Terminal half-life; (9) Anti-therapeutic antibodies to T-DM1

Efficacy Outcome Measures

The objective response rate using modified RECIST, v1.0 will be assessed as the efficacy outcome measure. The secondary efficacy outcome measures of this study are the following: (1) PFS, defined as the time from the study treatment initiation to the first occurrence of disease progression or death on study (within 30 days of the last dose of study treatment) from any cause, as determined by investigator review of tumor assessments using modified RECIST, v1.0; and (2) Duration of response, defined as the first occurrence of a documented objective response until the time of disease progression, as determined by investigator review of tumor assessments using modified RECIST (v1.0), or death on study (within 30 days of the last dose of study treatment) from any cause.

Study Treatment

T-DM1 will be administered no more frequently than every 3 weeks at a dose of 2.4, 3.0, or 3.6 mg/kg IV. Any patient may be de-escalated to a T-DM1 dose as low as 2.4 mg/kg. Depending on the toxicity encountered in the cohort of patients that begin therapy at 3.0 mg/kg, and if 3.0 mg/kg T-DM1 is confirmed to be tolerable, patients may be escalated to a dose of 3.6 mg/kg IV every 3 weeks in subsequent cycles. Pertuzumab will be administered at a loading dose of 840 mg IV on Day 1, Cycle 1, followed by 420 mg IV every 3 weeks in subsequent cycles.

Statistical Methods

The primary efficacy endpoint of this study is investigator-assessed objective response, defined as a complete or partial response determined on two consecutive occasions ≥4 weeks apart. An estimate of the objective response rate will be computed as well as the corresponding 95% confidence interval. For objective response, patients without a valid post-baseline tumor assessment will be counted as non-responders. For duration of response and PFS, data from patients who are lost to follow-up will be treated as censored on the last date the patient was known to be progression-free. Data for patients without post-treatment tumor assessment or death will be censored at the date of the treatment initiation plus 1 day.

Example 5

Clinical Study of Trastuzumab-MCC-DM1 (T-DM1) in Combination with GDC-0941

A phase Ib, open-label study of the combination of T-DM1 administered intravenously and GDC-0941 administered orally to patients with HER2-positive metastatic breast cancer who have progressed on previous trastuzumab-based therapy was designed to characterize the safety, tolerability, pharmacokinetics, and activity of the combination. The primary objectives of this study are: To evaluate the safety and tolerability of GDC-0941 administered with T-DM1; To estimate the MTD of GDC-0941 when administered with T-DM1; identify a recommended Phase II dose for GDC-0941 administered in combination with T-DM1; and To characterize any observed anti-tumor activity of GDC-0941 when administered in combination with T-DM1 The pharmacokinetic objectives are: To characterize the pharmacokinetics of GDC-0941 in the absence and presence of T-DM1; and To characterize the pharmacokinetics of T-DM1 in the relative absence and presence of GDC-0941.

GDC-0941 Formulation

GDC-0941 is a dry powder intended for PO administration. The formulated drug product will be provided in hard gelatin capsules of two strengths (15 and 50 mg) that are encapsulated with size 0 shells and differentiated by color. Excipients included in the capsule formulations are microcrystalline cellulose NF/EP, sodium lauryl sulfate NF/DP (in the 50 mg strength only), citric acid anhydrous USP/EP, croscarmellose sodium NF/EP, colloidal silicon dioxide NF/EP, and magnesium stearate (non-bovine) NF/EP. GDC-0941 capsules should be stored at refrigerated temperature between 36° F. and 46° F. (2° C. and 8° C.). Patients will be instructed to store study drug at refrigerated temperature between 36° F. and 46° F. (2° C. and 8° C.).

Outcome Measures

Outcome measures for safety, pharmacokinetics, pharmacodynamic, and efficacy will be determined and assessed, including Statistical Methods, as in Example 4.

Study Treatment

Study treatments will be administered in 3-week cycles. Patients receiving clinical benefit from study treatment may have the possibility of treatment for more cycles which may occur in a separate study, depending on the development status, drug availability, and other factors.

In the dose escalation phase of the study, patients enrolled will receive a single dose of GDC-0941 on Day 1 of Cycle 1 on an empty stomach, to allow pre- and post-dose GDC-0941 PK sample collection and to observe intra-patient variability. The starting dose of GDC-0941 will be 60 mg qd, which is a dose that has been determined to be safe as a single agent without any dose limiting toxicities in a phase I study. On Day 2 of Cycle 1, full-dose T-DM1 will be administered at 3.6 mg/kg IV over 90 minutes without a loading dose. This will be followed by a dose of GDC-0941. Patients will be monitored for 90 minutes after the first T-DM1 infusion. GDC-0941 will then be given once daily, for a total of 14 doses followed by 1 week off for the first cycle.

Dose escalation of GDC-0941 in subsequent patients will continue until progression or intolerability. Subsequent study treatment cycles will be 3 weeks in length, with T-DM1 3.6 mg/kg IV administered over 30 minutes first on Day 1 of each cycle and GDC-0941 administered after the T-DM1 infusion, and continuing for a total of 2 weeks on and 1 week off. Dosing will continue until progression or intolerability. T-DM1 will be administered as a 30 to 90 minute (±10) IV infusion, depending on how T-DM1 was tolerated in the parent study. If the 90 minute infusion is well tolerated, subsequent infusions may be delivered over 30 (±10) minutes.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

We claim:

1. A method for the treatment of a cancer expressing human epidermal growth factor receptor 2 protein (HER2), comprising administering to a human having said cancer a therapeutic combination comprising a therapeutically effective amount of trastuzumab-MCC-DM1 and a therapeutically effective amount of a chemotherapeutic agent selected from GDC-0941 and GNE-390, as a combined formulation or by alternation.

2. The method of claim 1 wherein the chemotherapeutic agent is GDC-0941.

3. The method of claim 1 wherein the chemotherapeutic agent is GNE-390.

4. The method of claim 1 wherein the therapeutically effective amount of trastuzumab-MCC-DM1 and the therapeutically effective amount of the chemotherapeutic agent are administered as a combined formulation.

5. The method of claim 1 wherein the therapeutically effective amount of trastuzumab-MCC-DM1 and the therapeutically effective amount of the chemotherapeutic agent are administered by alternation.

6. The method of claim 5 wherein the chemotherapeutic agent is administered and then trastuzumab-MCC-DM1 is subsequently administered.

7. The method of claim 4 wherein the therapeutic combination is administered at about three week intervals.

8. The method of claim 5 wherein trastuzumab-MCC-DM1 is administered at intervals from about one week to three weeks.

9. The method of claim 1 wherein administration of the therapeutic combination results in a synergistic effect.

10. The method of claim 1 wherein the cancer expressing HER2 is breast, ovary, or stomach cancer.

11. The method of claim 1 wherein the amount of trastuzumab-MCC-DM1 and the amount of chemotherapeutic agent are each from about 1 mg to about 1000 mg.

12. The method of claim 1 wherein the amount of trastuzumab-MCC-DM1 and the amount of chemotherapeutic agent are in a ratio of about 1:10 to about 10:1 by weight.

13. The method of claim 1 wherein the human having said cancer has received trastuzumab or lapatinib therapy.

14. The method of claim 1, wherein trastuzumab-MCC-DM1 is administered at about one week to about three week intervals to the human.

15. The method of claim 14, wherein the trastuzumab-MCC-DM1 is administered once every three weeks to the human.

16. The method of claim 15, wherein the trastuzumab-MCC-DM1 is administered at a dose of 2.4, 3.0 or 3.6 mg/kg intravenously.

17. The method of claim 16, wherein the trastuzumab-MCC-DM1 is administered at a dose of 3.6 mg/kg intravenously.

18. The method of claim 14, wherein the cancer expressing HER2 is breast cancer.

19. The method of claim 18, wherein the breast cancer is metastatic breast cancer.

20. The method of claim 14, wherein the human has received trastuzumab or lapatinib therapy.

21. The method of claim 14, wherein the human has received trastuzumab and lapatinib therapy.

22. The method of claim 8, wherein the trastuzumab-MCC-DM1 is administered once every three weeks to the human.

23. The method of claim 22, wherein the trastuzumab-MCC-DM1 is administered at a dose of 2.4, 3.0 or 3.6 mg/kg intravenously.

24. The method of claim 23, wherein the trastuzumab-MCC-DM1 is administered at a dose of 3.6 mg/kg intravenously.

25. The method of claim 8, wherein the cancer expressing HER2 is breast cancer.

26. The method of claim 25, wherein the breast cancer is metastatic breast cancer.

27. The method of claim 8, wherein the human has received trastuzumab or lapatinib therapy.

28. The method of claim 8, wherein the human has received trastuzumab and lapatinib therapy.

* * * * *

UNITED STATES PATENT AND TRADEMARK OFFICE
CERTIFICATE OF CORRECTION

| | | |
|---|---|---|
| PATENT NO. | : 8,663,643 B2 | Page 1 of 1 |
| APPLICATION NO. | : 12/400988 | |
| DATED | : March 4, 2014 | |
| INVENTOR(S) | : Berry et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 815 days.

Signed and Sealed this
Fifteenth Day of September, 2015

Michelle K. Lee
*Director of the United States Patent and Trademark Office*